US012747246B2

(12) United States Patent
Xie et al.

(10) Patent No.: US 12,747,246 B2
(45) Date of Patent: Sep. 29, 2026

(54) FUSED CYCLIC COMPOUND AS WEE-1 INHIBITOR, PREPARATION METHOD THEREFOR AND USE THEREOF

(71) Applicant: WIGEN BIOMEDICINE TECHNOLOGY (SHANGHAI) CO., LTD., Shanghai (CN)

(72) Inventors: Yuli Xie, Shanghai (CN); Houxing Fan, Shanghai (CN); Lihui Qian, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 413 days.

(21) Appl. No.: 18/281,862

(22) PCT Filed: Apr. 28, 2022

(86) PCT No.: PCT/CN2022/089861

§ 371 (c)(1),
(2) Date: Sep. 13, 2023

(87) PCT Pub. No.: WO2022/228511

PCT Pub. Date: Nov. 3, 2022

(65) Prior Publication Data

US 2024/0182482 A1 Jun. 6, 2024

(30) Foreign Application Priority Data

Apr. 30, 2021 (CN) ......................... 202110485597.3

(51) Int. Cl.

| | |
|---|---|
| ***C07D 487/06*** | (2006.01) |
| ***A61K 31/519*** | (2006.01) |
| ***A61P 35/00*** | (2006.01) |
| ***C07D 519/00*** | (2006.01) |

(52) U.S. Cl.

CPC .......... *C07D 487/06* (2013.01); *A61K 31/519* (2013.01); *A61P 35/00* (2018.01); *C07D 519/00* (2013.01)

(58) Field of Classification Search

None

See application file for complete search history.

(56) References Cited

U.S. PATENT DOCUMENTS

| | | | | |
|---|---|---|---|---|
| 2020/0157112 A1 | 5/2020 | Huang et al. | | |
| 2022/0194960 A1* | 6/2022 | Zhu | ...................... | C07D 519/00 |

FOREIGN PATENT DOCUMENTS

| | | | | |
|---|---|---|---|---|
| CN | 101784551 A | 7/2010 | | |
| CN | 102066338 A | 5/2011 | | |
| CN | 103703005 A | 4/2014 | | |
| CN | 105188704 A | 12/2015 | | |
| CN | 109422754 A | 3/2019 | | |
| CN | 109810111 A | 5/2019 | | |
| CN | 110467615 A | 11/2019 | | |
| WO | WO-2020192581 A1 * | 10/2020 | ........... | C07D 487/04 |
| WO | 2021074251 A1 | 4/2021 | | |
| WO | 2022171126 A1 | 8/2022 | | |
| WO | 2022174765 A1 | 8/2022 | | |
| WO | 2023280180 A1 | 1/2023 | | |

* cited by examiner

*Primary Examiner* — Clinton A Brooks
*Assistant Examiner* — Kyle Nottingham
(74) *Attorney, Agent, or Firm* — SZDC Law PC

(57) ABSTRACT

Disclosed in the present invention are a fused cyclic compound as a Wee-1 inhibitor, a preparation method therefor and use thereof. Specifically, the present invention relates to a compound of general formula (1), a preparation method therefor, and use of the compound of general formula (1) or an isomer, a crystalline form, a pharmaceutically acceptable salt, a hydrate or a solvate thereof as a Wee-1 inhibitor in the preparation of an anti-tumor drug.

(1)

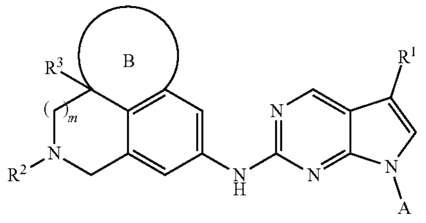

12 Claims, No Drawings

FUSED CYCLIC COMPOUND AS WEE-1 INHIBITOR, PREPARATION METHOD THEREFOR AND USE THEREOF

The present application is the National Stage Application of PCT/CN2022/089861, filed on Apr. 28, 2022, which claims priority to Chinese Application CN 202110485597.3 filed on Apr. 30, 2021, which is incorporated herein by reference in its entirety.

TECHNICAL FIELD

The present invention relates to the field of pharmaceutical chemistry, and particularly to a compound with an inhibitory effect on Wee-1 kinase, a preparation method therefor and use of such compounds in the preparation of an anti-tumor drug.

BACKGROUND

Wee-1 protein kinase is an important negative regulatory protein in cell cycle checkpoints. The cell cycle checkpoints include a G1 checkpoint for the transition from G1 phase (gap 1 phase) to S phase (DNA synthesis phase), a G2 checkpoint for the transition from G2 phase (gap 2 phase) to M phase (mitotic phase), and a spindle checkpoint for the transition from metaphase to anaphase of the M phase. The Wee-1 protein kinase plays an important role at the G2 phase checkpoint. The start of M phase depends on CDK1 kinase activity, and Wee-1 inhibits the activity of CDK1 by phosphorylating Tyr 15 of CDK1 protein, preventing cells from entering M phase. In contrast, polo kinase phosphorylates Wee-1 and activates the degradation of Wee-1 protein, promoting cells to enter M phase. Thus, Wee-1 kinase activity determines the activity of the G2 checkpoint, thereby regulating the transition from G2 to M phase of cells.

The cell cycle checkpoints are activated primarily following DNA damage and play an important role in the repair of DNA in cells. The normal activation of the cell cycle checkpoints blocks the cell cycle and promotes DNA repair. If the functions of the checkpoints are inhibited, the DNA damage cannot be repaired, and the cells undergo apoptosis. Compared with normal cells, various tumor cells repair DNA damage and avoid apoptosis mainly depending on the activation of the G2 phase checkpoint due to the impaired function of the important protein p53 protein at the G1 phase checkpoint. Therefore, tumor cells can be selectively killed by inhibiting the G2 phase checkpoint. The important role of Wee-1 kinase activity in the G2 phase checkpoint suggests that Wee-1 kinase determines the repair or death of tumor cells after DNA damage, and inhibition of Wee-1 activity can promote unrepaired tumor cells after DNA damage to enter M phase and induce apoptosis.

Studies have shown that in addition to its role in the G2 checkpoint, Wee-1 is involved in DNA synthesis, DNA homologous repair, post-translational modification of chromosomal histones, and other functions closely related to the development and progression of tumors. The expression of Wee-1 is greatly increased in a large number of tumors including liver cancer, breast cancer, cervical cancer, melanoma, lung cancer and the like. The high expression of Wee-1 is in a positive correlation with the progression and poor prognosis of tumors, suggesting that Wee-1 kinase may be involved in the development and progression of tumors. Studies on in vitro cell models and in vivo animal models have shown that inhibiting Wee-1 activity while inducing DNA damage can significantly inhibit the growth of a variety of tumors.

Therefore, the development of specific and highly active micromolecule inhibitors against Wee-1 kinase would be of important clinical value for tumor treatment, especially those targeting tumors with impaired G1 checkpoints such as P53 deletion.

At present, the Wee-1 inhibitor AZD1775 (MK-1775, Adavosertib) of AstraZeneca has entered the clinical phase II stage, and more than 30 clinical trials are under development. Patents related to AZD1775 include US20070254892, WO2007126122, EP2213673, WO2008133866, WO2011034743 and the like. Abbott and Abbvie also have conducted research on Wee-1 inhibitors. The related patents include mainly US2012220572, WO2013126656, WO2013012681, WO2013059485, WO2013013031 and the like. Patents related to Wee-1 inhibitors of Almac include WO2014167347, WO2015019037, WO2015092431, WO2018011570, WO2018062932, WO2019138227 and the like. Patents related to Wee-1 of Girafpharma include WO2019074979 and WO2019074981. Patents related to Wee-1 research of Zeno include WO2018028008 and WO2019173082.

The Wee-1 inhibitors in the research still have some problems that the inhibitor used alone has a poor therapeutic effect, the cell activity of the inhibitor used in combination with other chemotherapeutic drugs is not strong enough, and thus the combined effect in clinic is not ideal. The drug resistance is usually generated in the later stage of a targeted therapy, and chemotherapy becomes a common means for treating advanced tumors. The treatment by using chemotherapeutic drugs alone often generates great side effects and the drug tolerance in patients is poor, so it is of great significance to invent a Wee-1 inhibitor having a good combined effect with chemotherapeutic drugs.

SUMMARY

The present invention provides a compound of general formula (1) or an isomer, a crystalline form, a pharmaceutically acceptable salt, a hydrate or a solvate thereof:

(1)

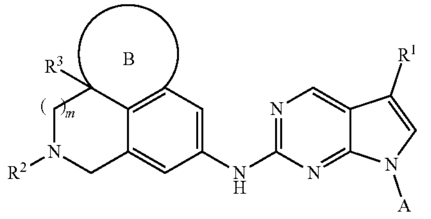

wherein in general formula (1):

m is 0 or 1;

$R^1$ is H or halogen;

$R^2$ is H, C1-C6 alkyl, C3-C6 cycloalkyl, deuterated C1-C6 alkyl, halogenated C1-C6 alkyl, C1-C6 alkyl substituted with CN, C1-C6 alkyl substituted with OH, C1-C6 alkyl substituted with C1-C3 alkoxy, C1-C6 alkyl substituted with C3-C6 cycloalkyl or 4- to 7-membered heterocycloalkyl;

$R^3$ is H or C1-C3 alkyl;

A is aryl or heteroaryl, wherein the aryl and heteroaryl are optionally substituted with 1 to 3 $R^6$, each $R^6$ is independently H, halogen, CN, C1-C6 alkyl, C1-C6 alkoxy, C3-C6 cycloalkyl, halogenated C1-C6 alkyl, halogenated C1-C6 alkoxy, C1-C6 alkyl substituted with OH, C1-C6 alkyl substituted with cyano, halogenated C3-C6 cycloalkyl, C3-C6 cycloalkyl substituted with hydroxy, C3-C6 cycloalkyl substituted with cyano, C3-C6 cycloalkyl substituted with $CF_3$, $—NR^{7a}R^{7b}$, $—N{=}S(O)R^{7a}R^{7b}$, $—P(O)R^{7a}R^{7b}$, $—S(O)_2R^{7a}$, $—S(O)_2NR^{7a}R^{7b}$, $—NR^8P(O)R^{7a}R^{7b}$, $—NR^8S(O)_2R^{7a}$, $—NRSC(O)R^{7a}$, $—N{=}S({=}NR^8)R^{7a}R^{7b}$ or pyridonyl, wherein $R^{7a}$ and $R^{7b}$ are independently C1-C3 alkyl, deuterated C1-C3 alkyl, C2-C6 alkenyl, C2-C6 alkynyl or C3-C6 cycloalkyl, or $R^{7a}$ and $R^{7b}$, together with the nitrogen, sulfur or phosphorus atom attached thereto, form 3- to 10-membered heterocycloalkyl, $R^8$ is H or C1-C3 alkyl, or $R^8$ and $R^{7a}$, together with the nitrogen and sulfur atoms or nitrogen and carbon atoms attached thereto, form 3- to 10-membered heterocycloalkyl;

B is partially unsaturated C5-C7 cycloalkyl or partially unsaturated 5- to 7-membered heterocycloalkyl.

In some embodiments of the present invention, in general formula (1),

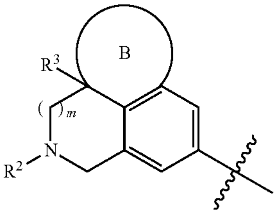

is

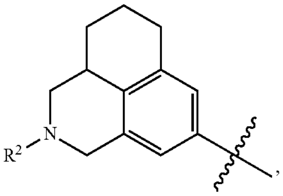,
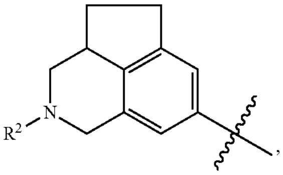,
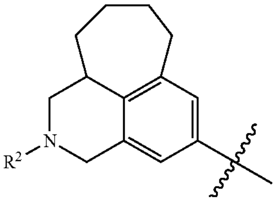,
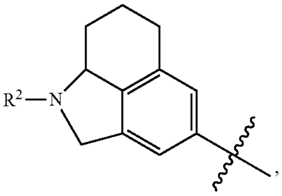,
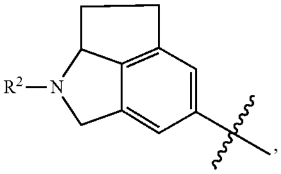,
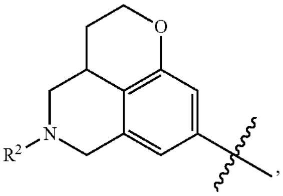,
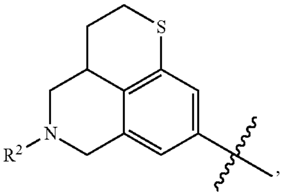,
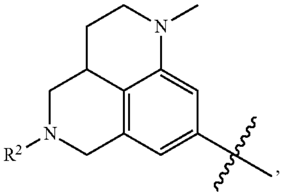, -continued

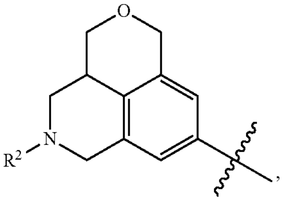,
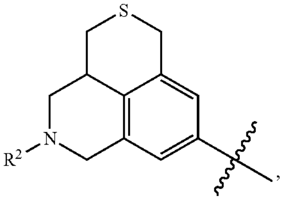,
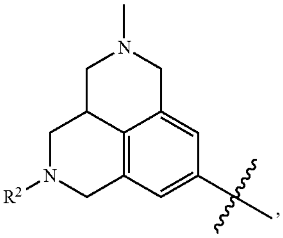,
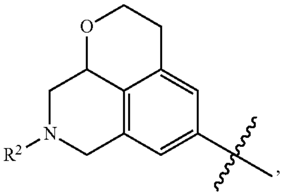,
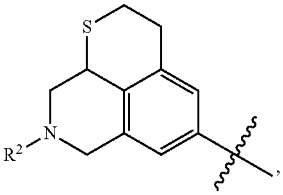,
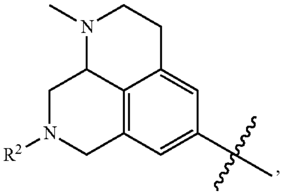,
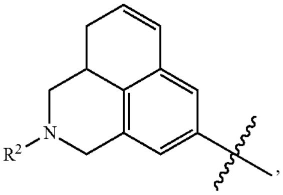,
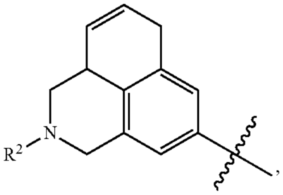,
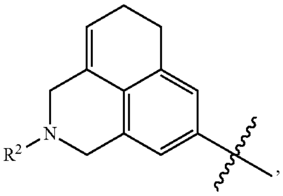,
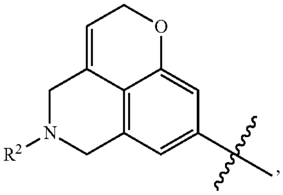,
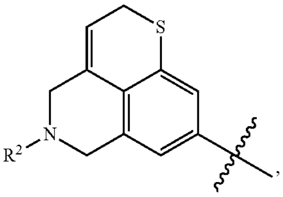,
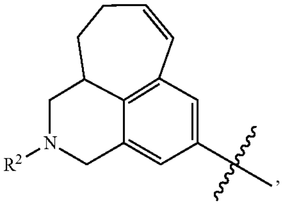,
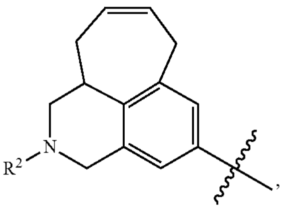,
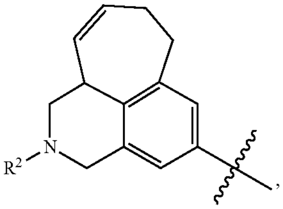,
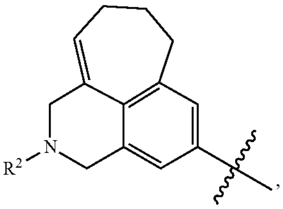,
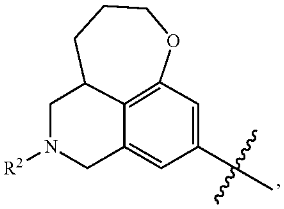, -continued
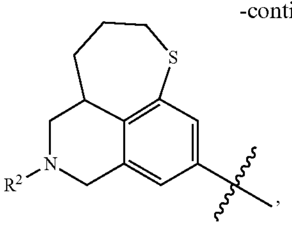, 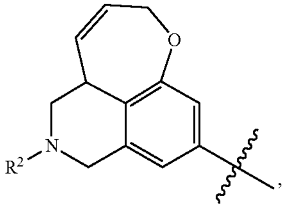,
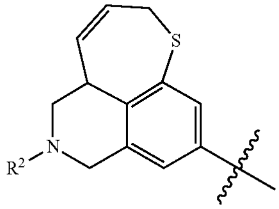, 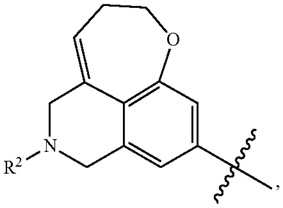,
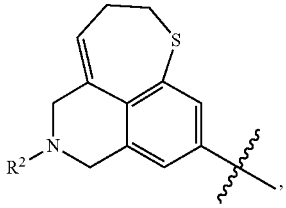, 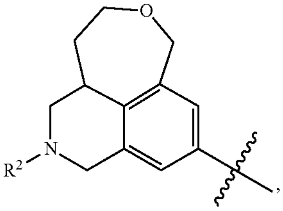,
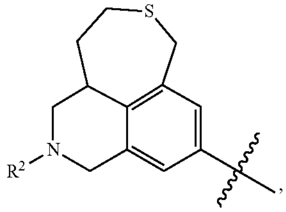,
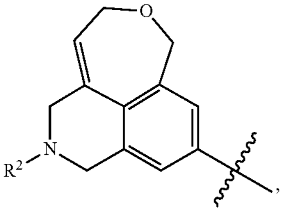, or
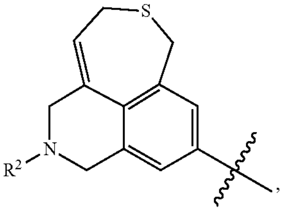,
wherein $R^2$ is H, Me, Et, $CD_3$,
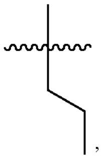, 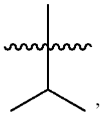, 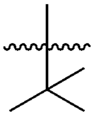, 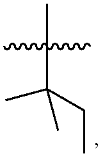,
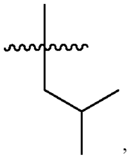, 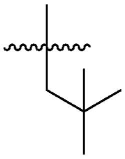, 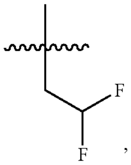, 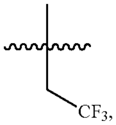
-continued
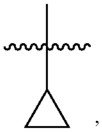, 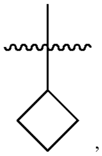, 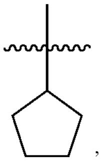, 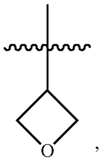, 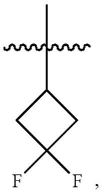,
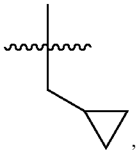, 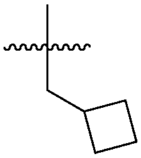, or 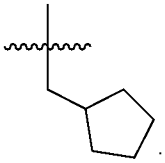.
In some embodiments of the present invention, in general formula (1),
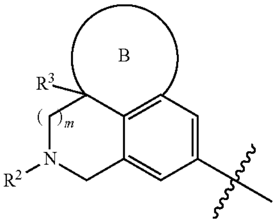 is
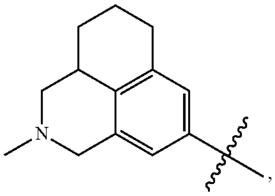, 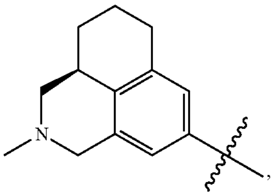,
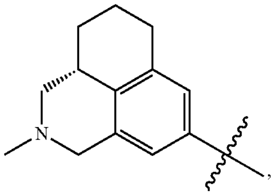, 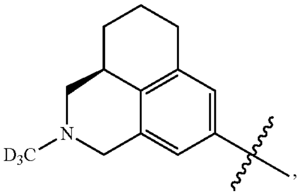,
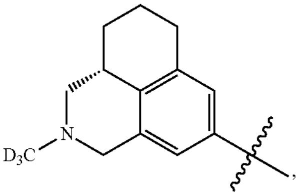, 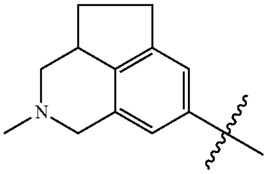,
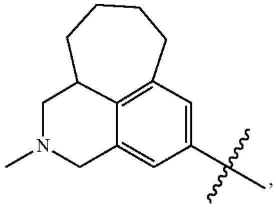, 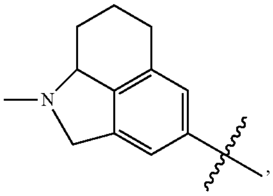,
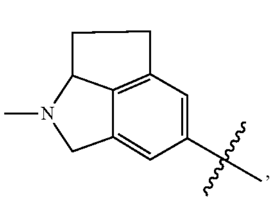, 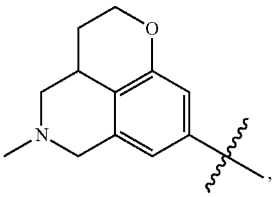, -continued
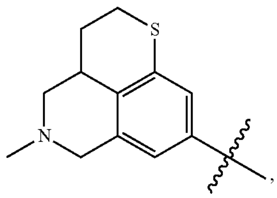,
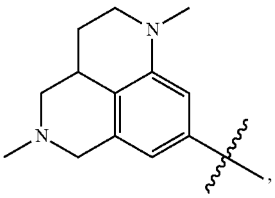,
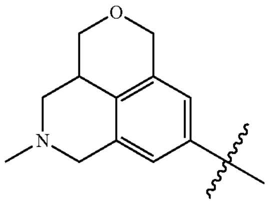,
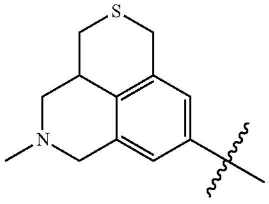,
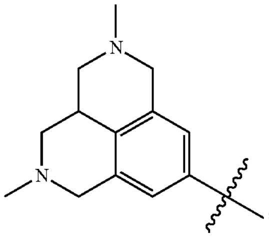,
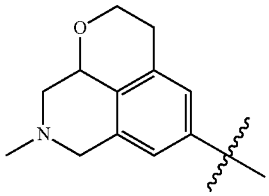,
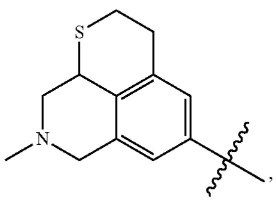,
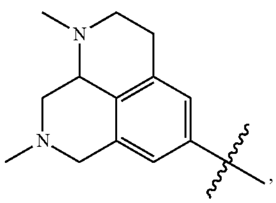,
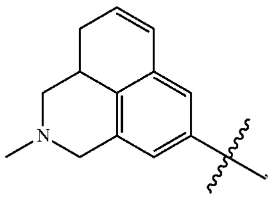,
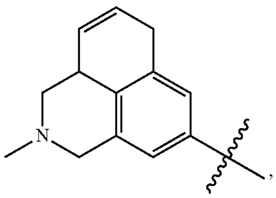,
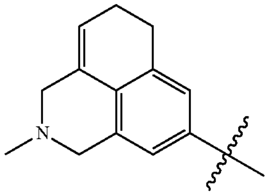,
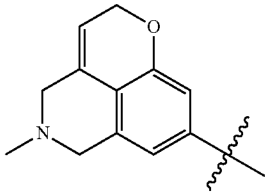,
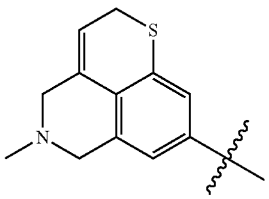,
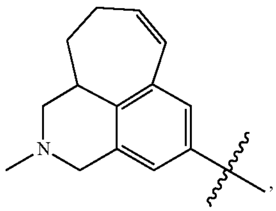,
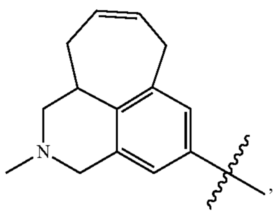,
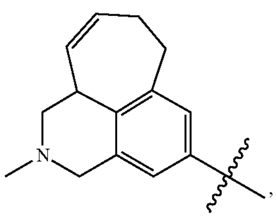,
-continued
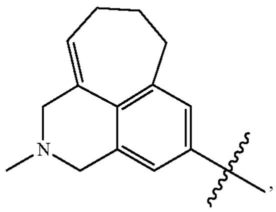,
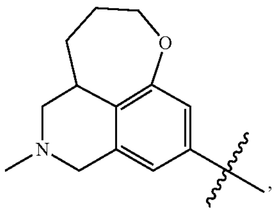,
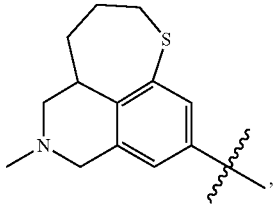,
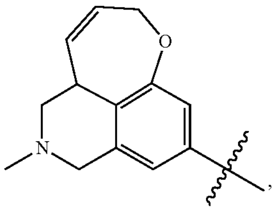,
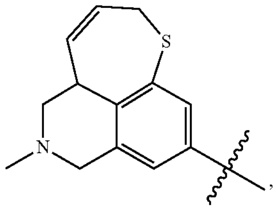,
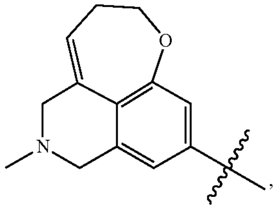,
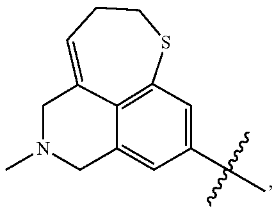,
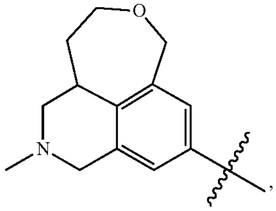,
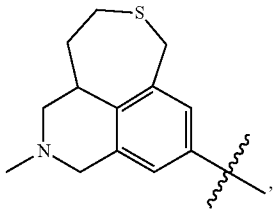,
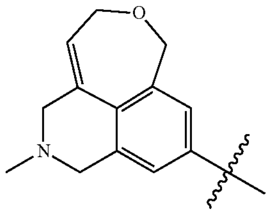
or
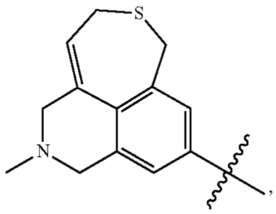, preferably
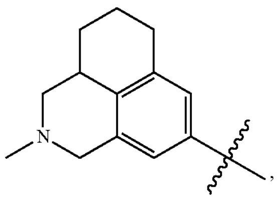, -continued

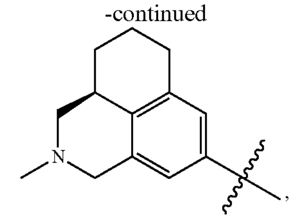

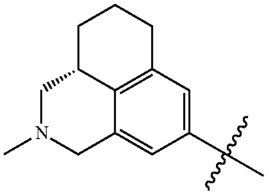

or

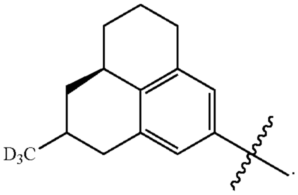

In some embodiments of the present invention, general formula (1) has a structure of general formula (1A):

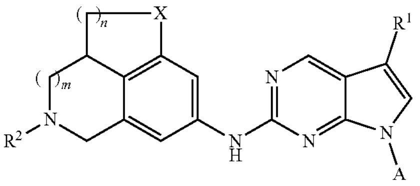

(1A)

wherein in general formula (1A):

n is 1, 2 or 3;

X is $CH_2$, O or S;

m, A, $R^1$ and $R^2$ are as defined above.

In some embodiments of the present invention, in general formula (1) or general formula (1A), A is phenyl, pyridinyl, pyrimidinyl or pyrazinyl, wherein the phenyl, pyridinyl, pyrimidinyl and pyrazinyl may be optionally substituted with 1 to 3 $R^6$, each $R^6$ is independently H, halogen, CN, C1-C6 alkyl, C1-C6 alkoxy, C3-C6 cycloalkyl, halogenated C1-C6 alkyl, halogenated C1-C6 alkoxy, C1-C6 alkyl substituted with hydroxy, C1-C6 alkyl substituted with cyano, halogenated C3-C6 cycloalkyl, C3-C6 cycloalkyl substituted with OH, C3-C6 cycloalkyl substituted with cyano, C3-C6 cycloalkyl substituted with $CF_3$, $—NR^{7a}R^{7b}$, $—N{=}S(O)R^{7a}R^{7b}$, $—P(O)R^{7a}R^{7b}$, $—S(O)_2R^{7a}$, $—S(O)_2NR^{7a}R^{7b}$, $—NR^8P(O)R^{7a}R^{7b}$, $—NR^8S(O)_2R^{7a}$, $—NR^8C(O)R^{7a}$, $—N{=}S({=}NR^8)R^{7a}R^{7b}$ or pyridonyl, wherein $R^{7a}$ and $R^{7b}$ are independently C1-C3 alkyl, deuterated C1-C3 alkyl, C2-C6 alkenyl, C2-C6 alkynyl or C3-C6 cycloalkyl, or $R^{7a}$ and $R^{7b}$, together with the nitrogen, sulfur or phosphorus atom attached thereto, form 3- to 10-membered heterocycloalkyl, $R^8$ is H or C1-C3 alkyl, or $R^8$ and $R^{7a}$, together with the nitrogen and sulfur atoms or nitrogen and carbon atoms attached thereto, form 3- to 10-membered heterocycloalkyl.

In some embodiments of the present invention, in general formula (1) or general formula (1A), A is

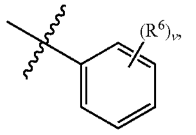

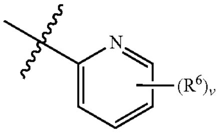

,

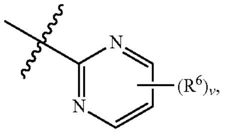

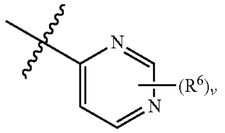

or

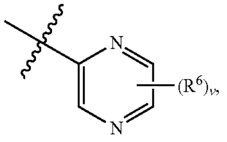

wherein v is 1, 2 or 3, and each $R^6$ is independently H, F, Cl, Br, I, Me, Et,

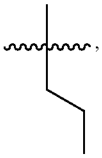

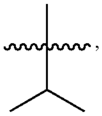

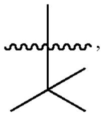

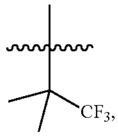

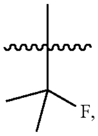

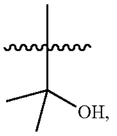

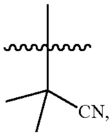

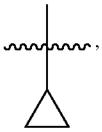

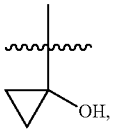

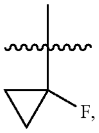

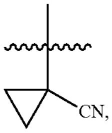

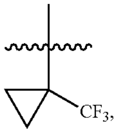

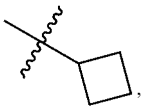

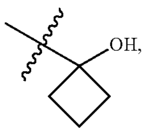

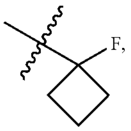

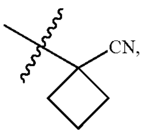

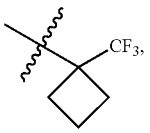

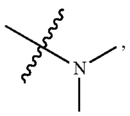

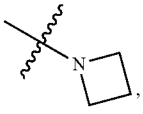

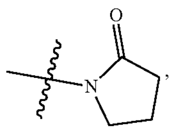

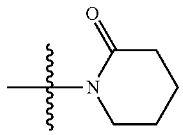

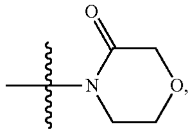

-continued
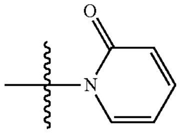,
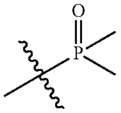,
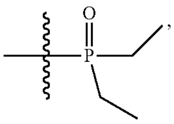,
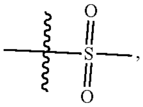,
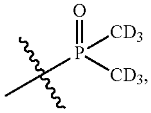,
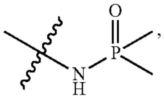,
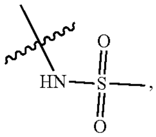,
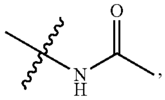,
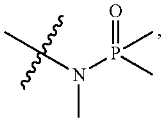,
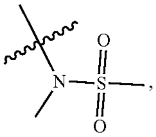,
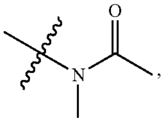,
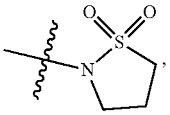,
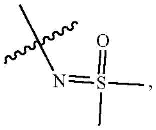,
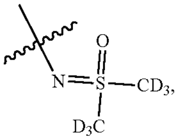,
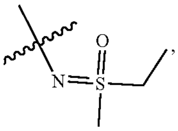,
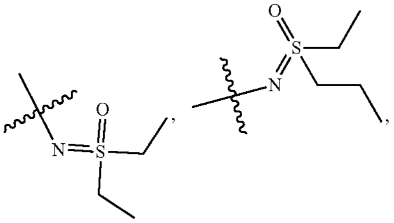,
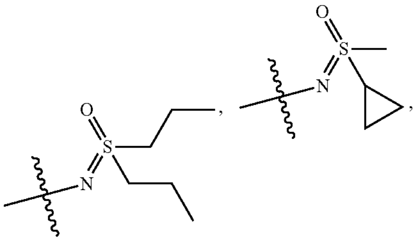,
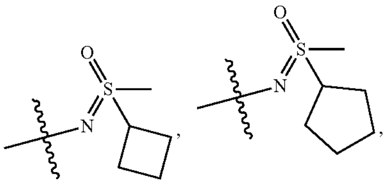,
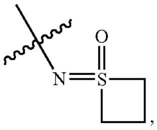,
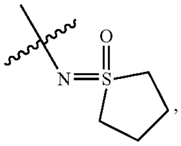,
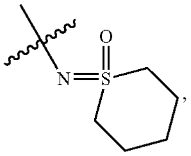,
-continued
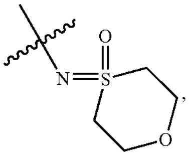,
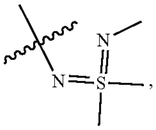,
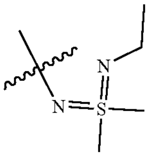 or
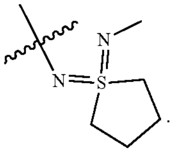.
In some embodiments of the present invention, in general formula (1) or general formula (1A), A is
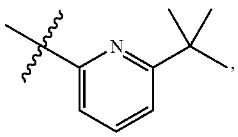,
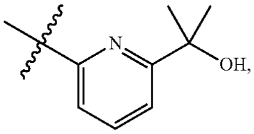,
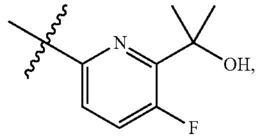,
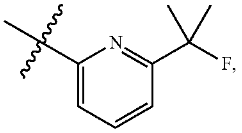,
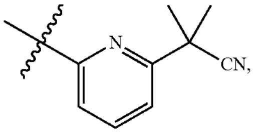,
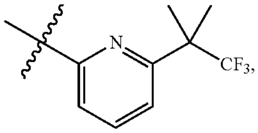,
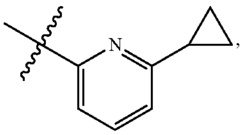,
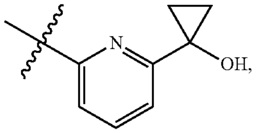,
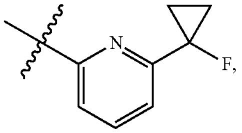,
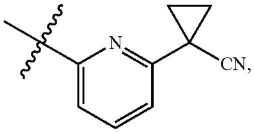,
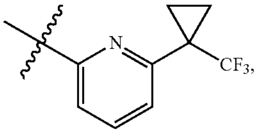,
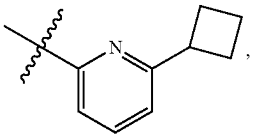,
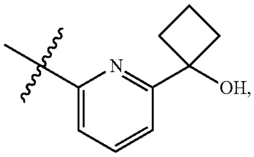,
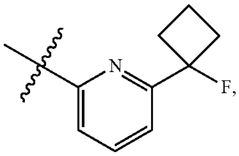,
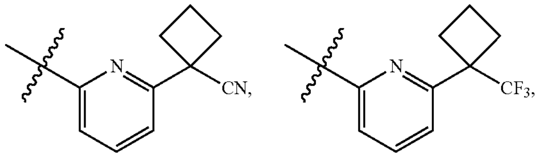, -continued
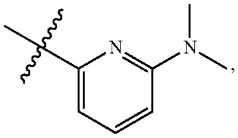,
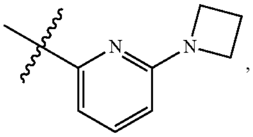,
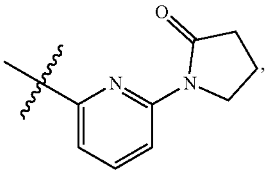,
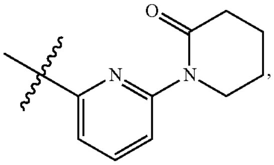,
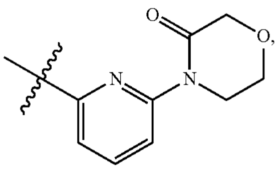,
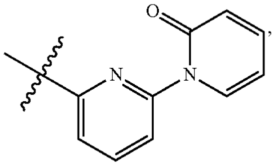,
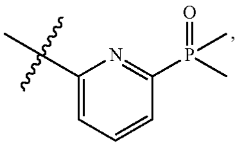,
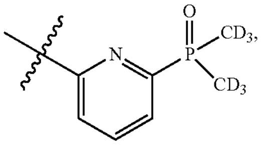,
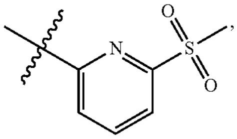,
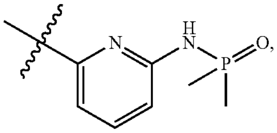,
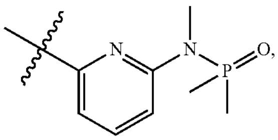,
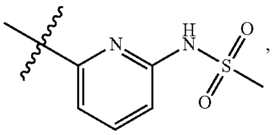,
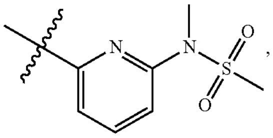,
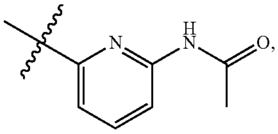,
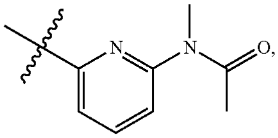,
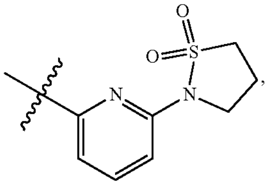,
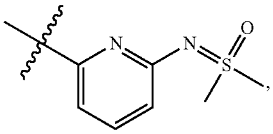,
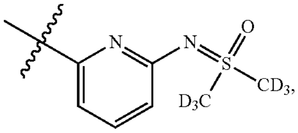,
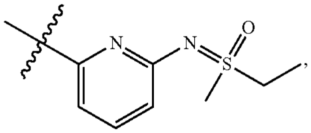,
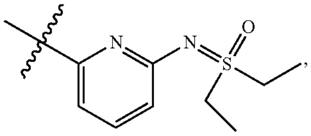,
-continued
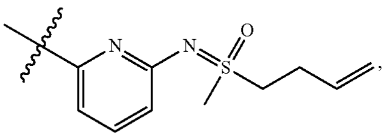,
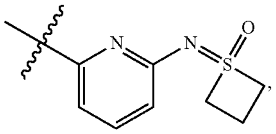,
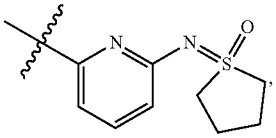,
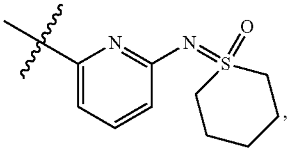,
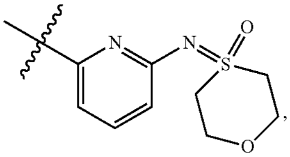,
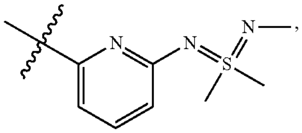,
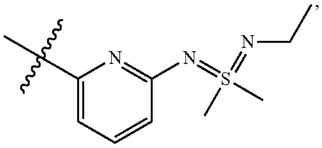,
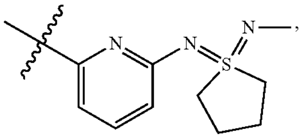,
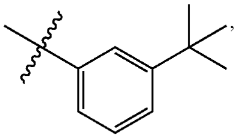,
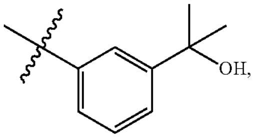,
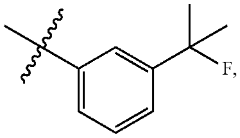,
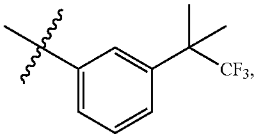,
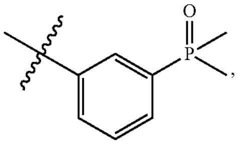,
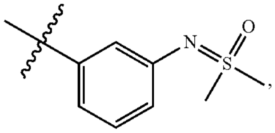,
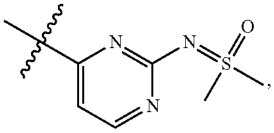,
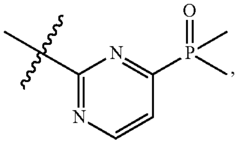,
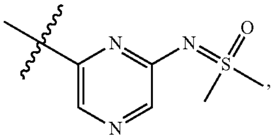, -continued
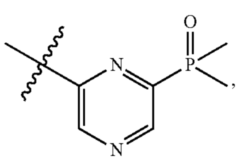
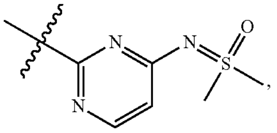
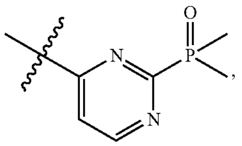
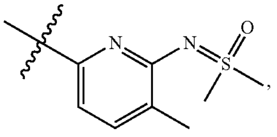
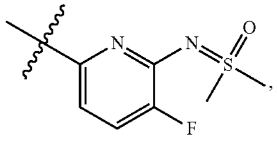
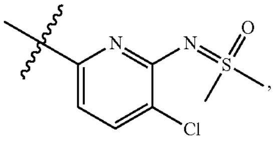
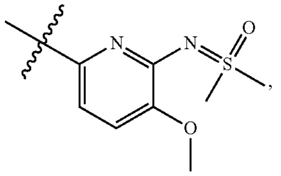
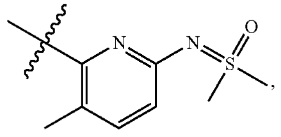
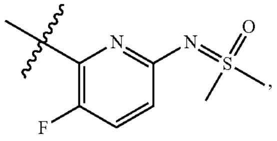
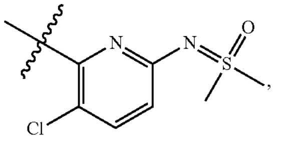
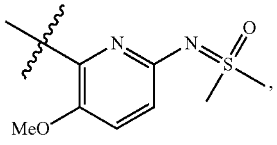
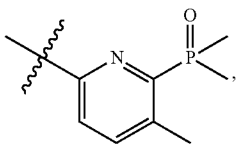
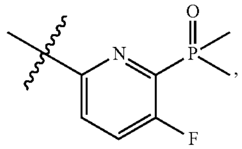
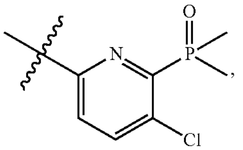
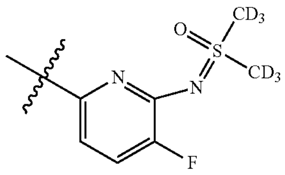
or
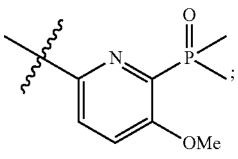
A is preferably 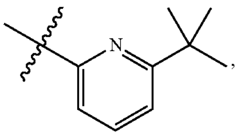
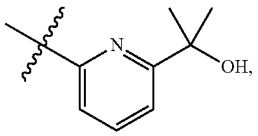
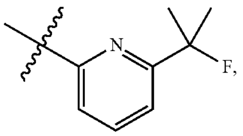
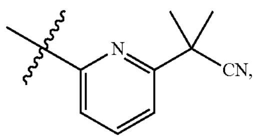
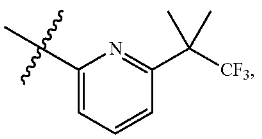
-continued
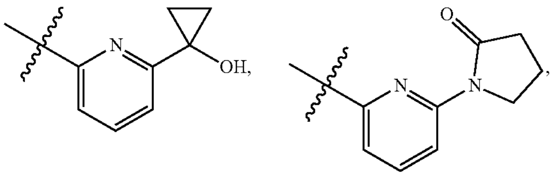
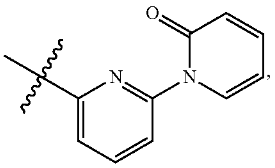
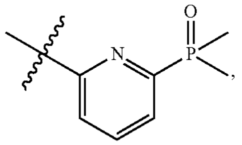
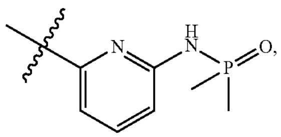
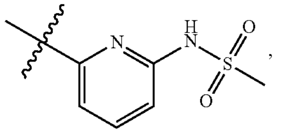
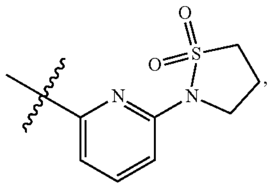
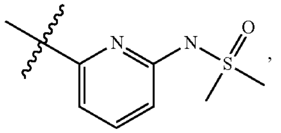
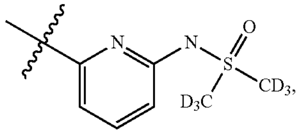
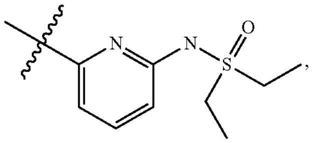
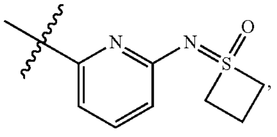
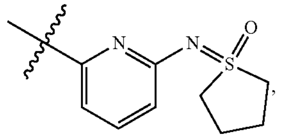
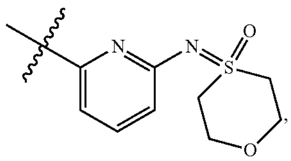
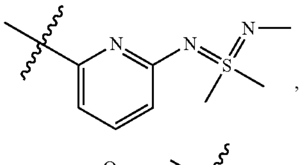
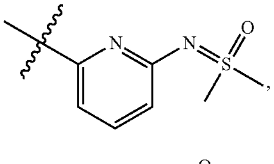
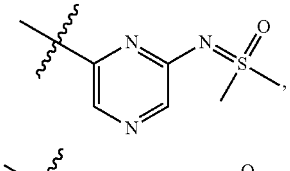
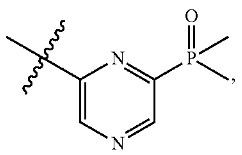
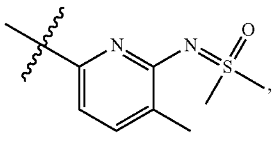

-continued
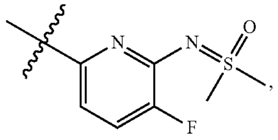
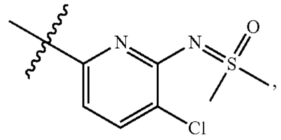
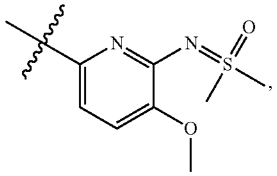
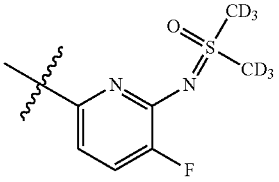
or
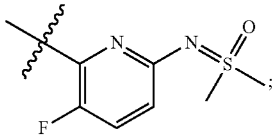
A is more preferably
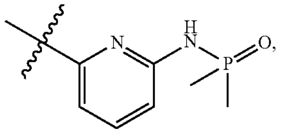
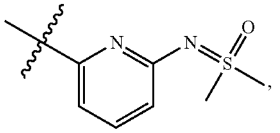
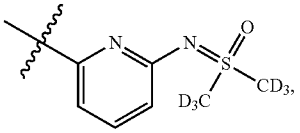
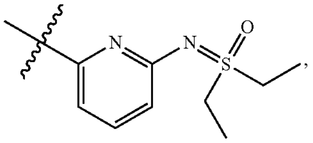
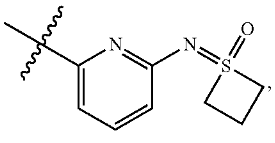
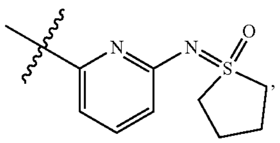
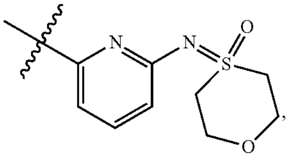
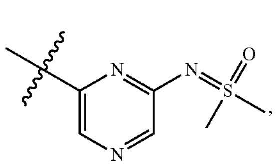
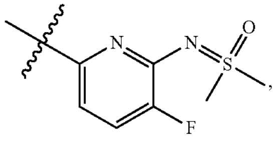
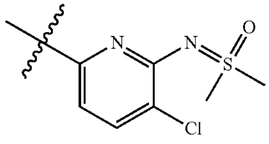
or
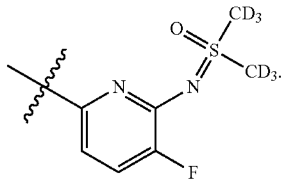
In another specific embodiment of the present invention, the compound of the present invention has one of the following structures:
1
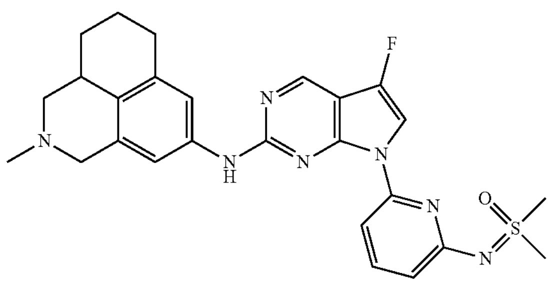
2
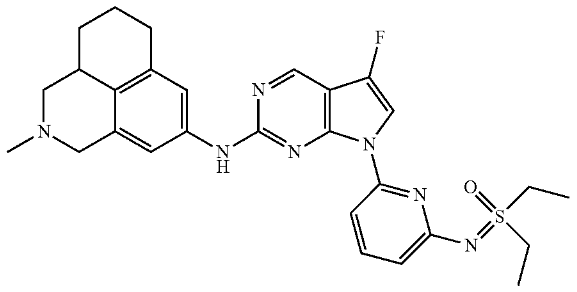
3
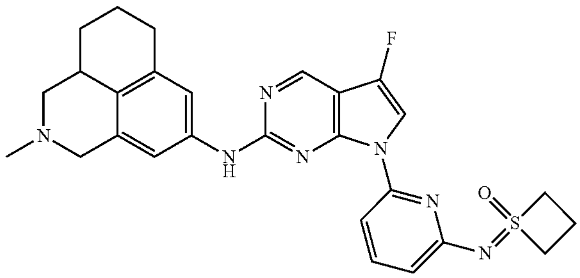
4
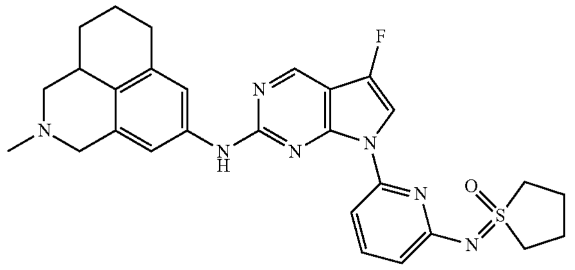
5
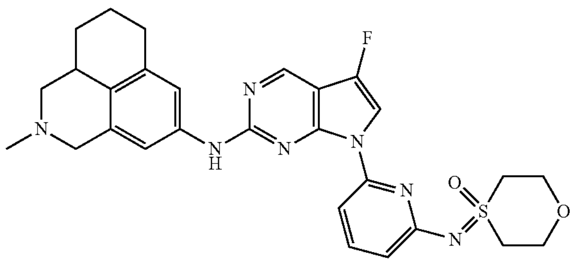

-continued
6
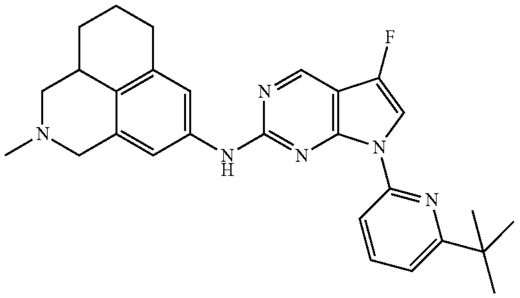
7
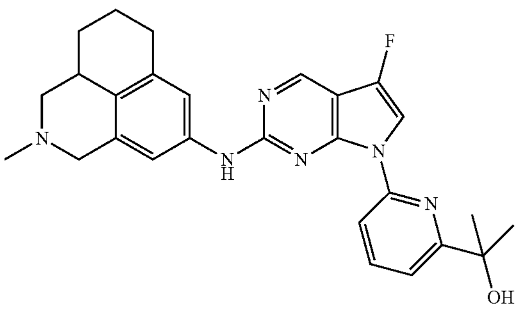
8
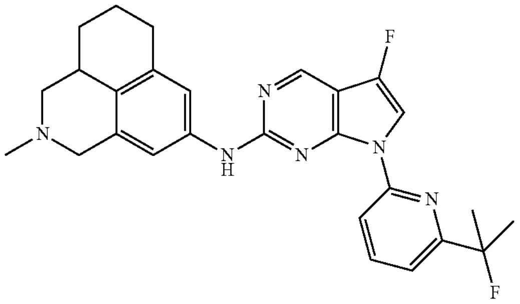
9
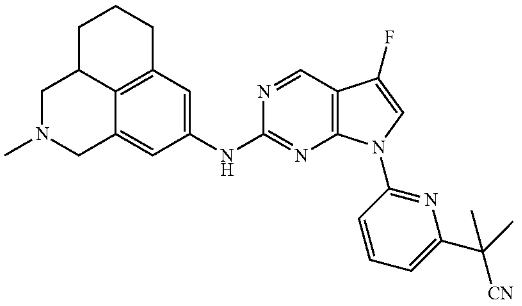
10
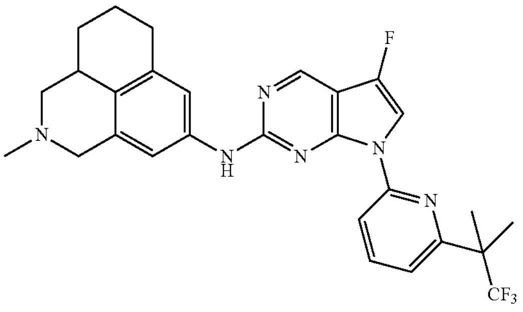
-continued
11
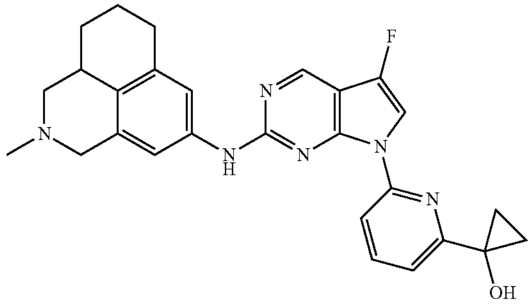
12
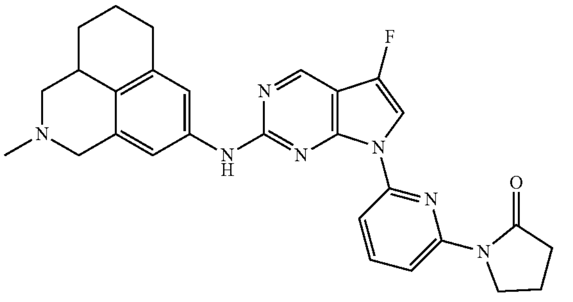
13
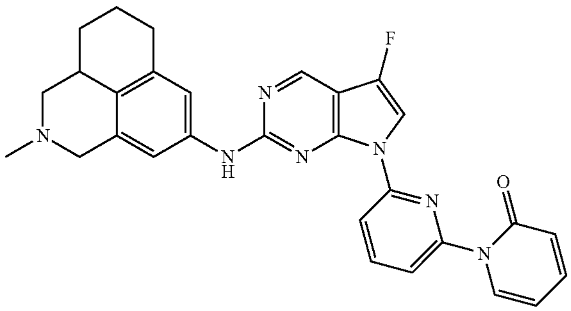
14
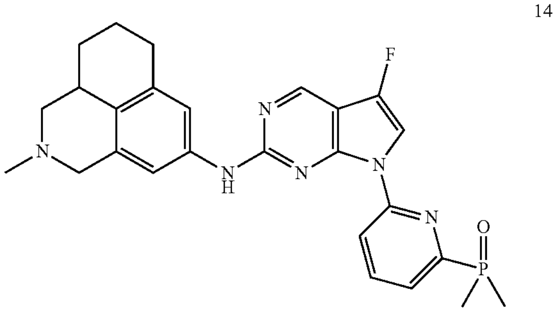
15
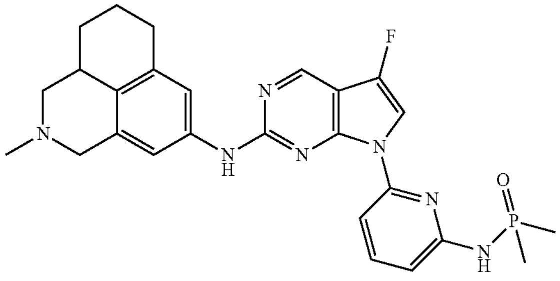

-continued
16
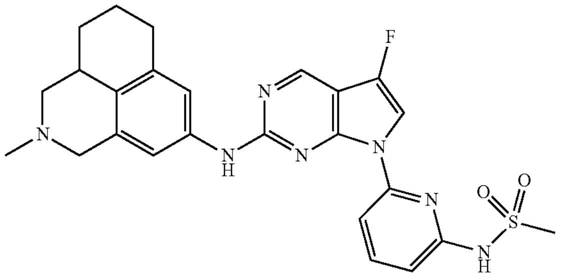
17
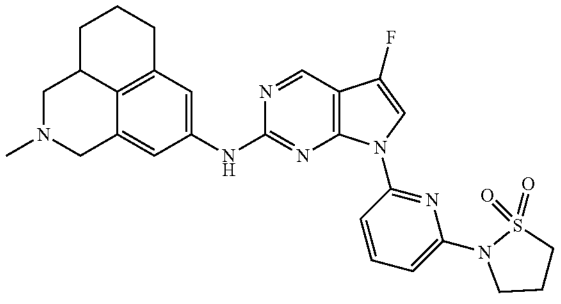
18
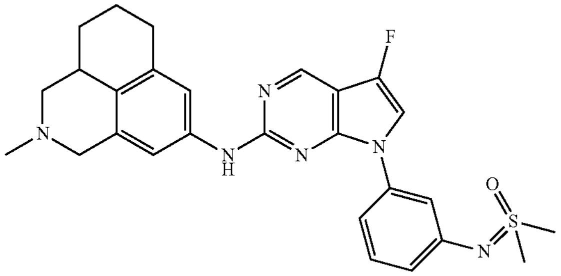
19
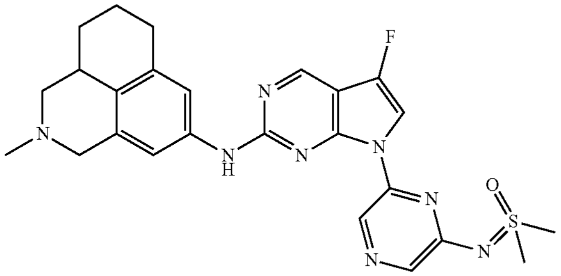
20
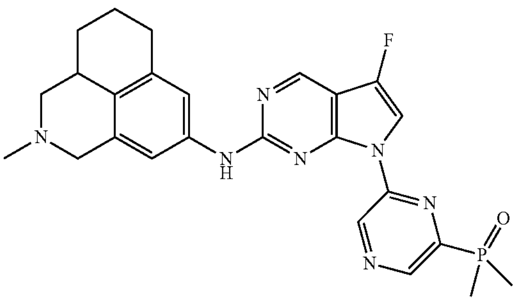
-continued
21
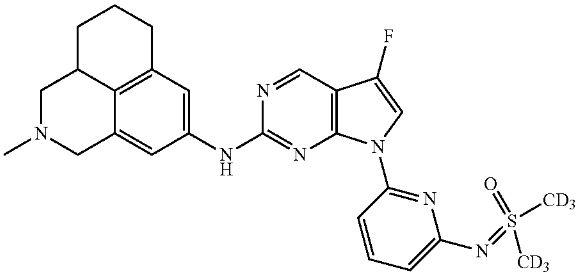
22
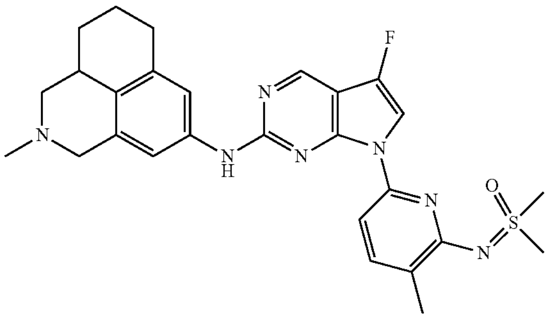
23
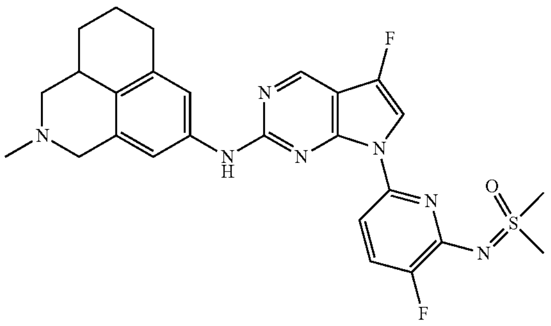
24
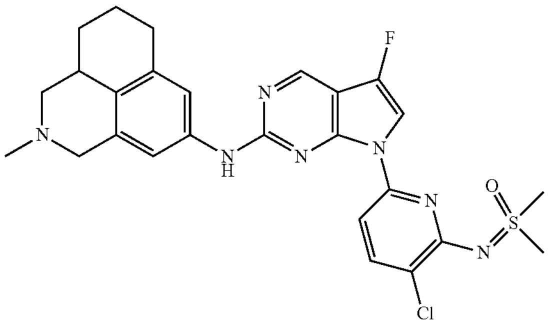

-continued
25
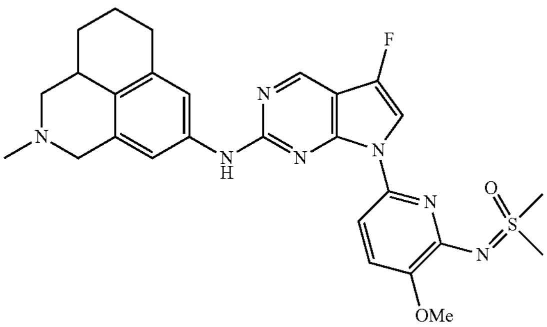
26
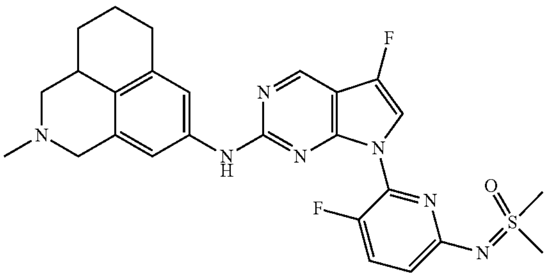
27
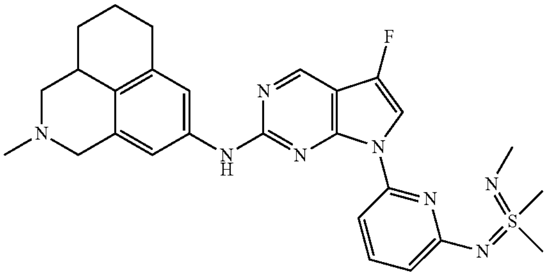
28
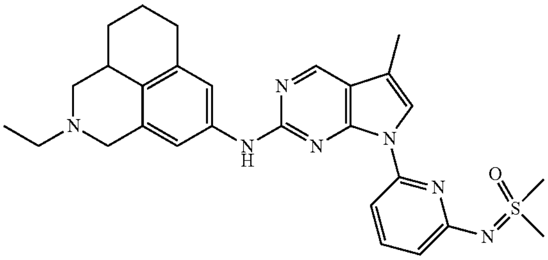
29
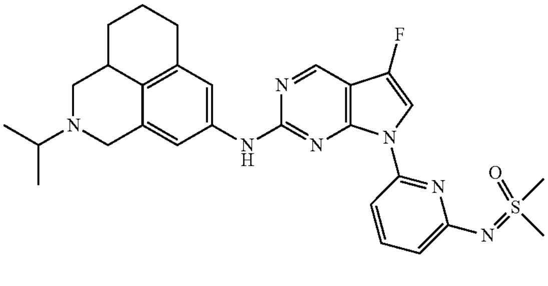
-continued
30
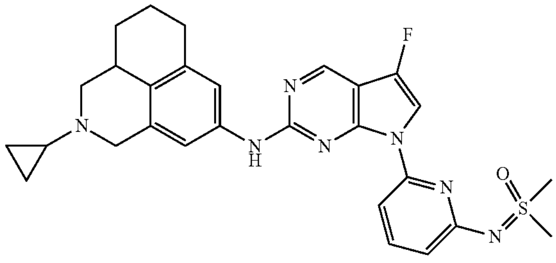
31
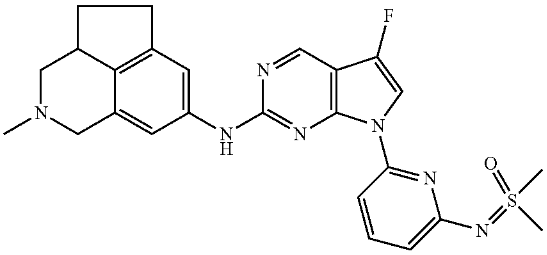
32
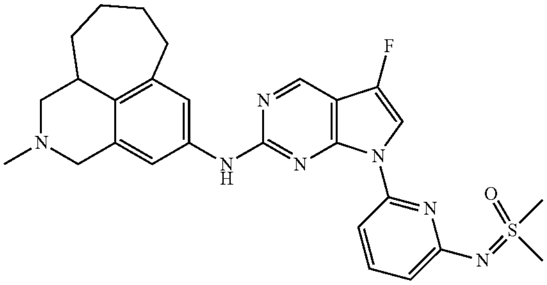
33
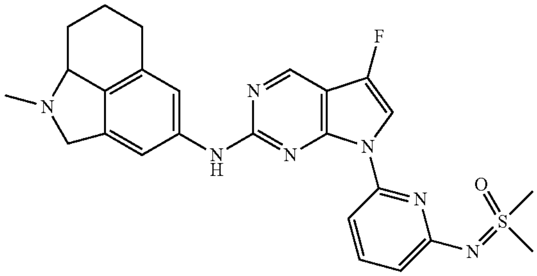
34
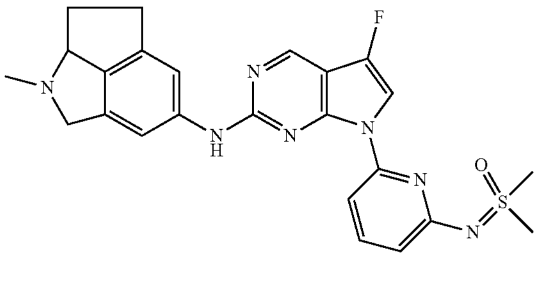

-continued
35
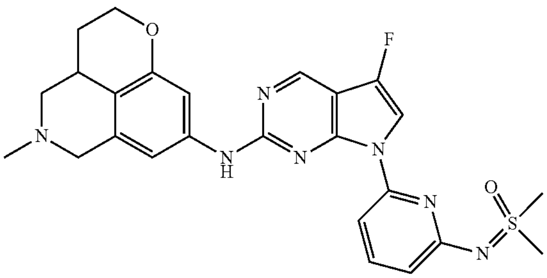
36
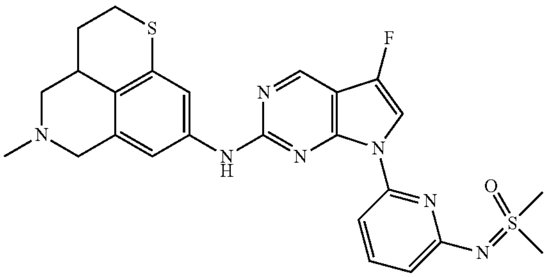
37
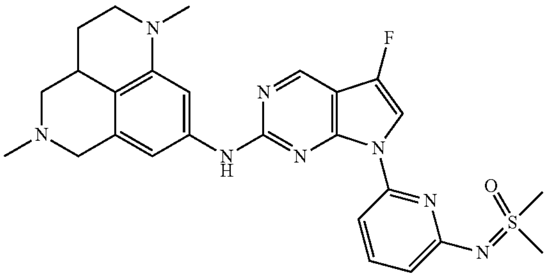
38
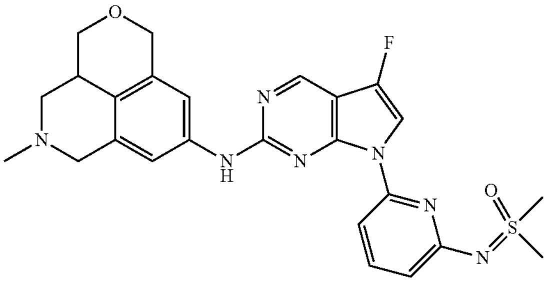
39
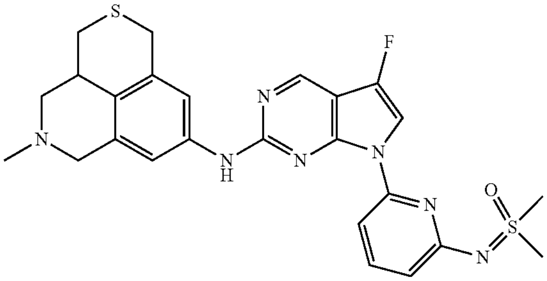
-continued
40
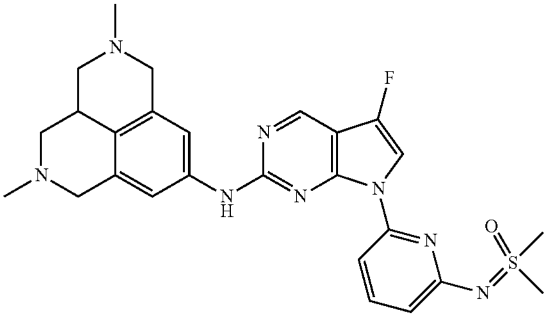
41
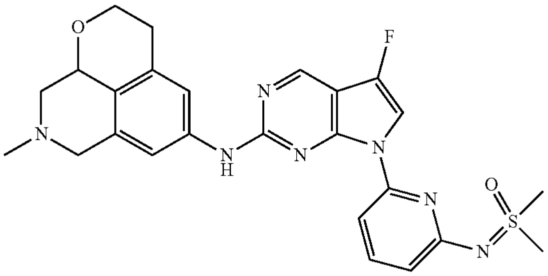
42
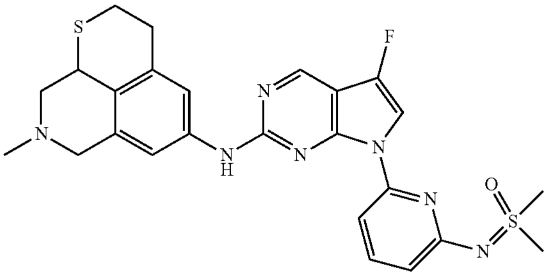
43
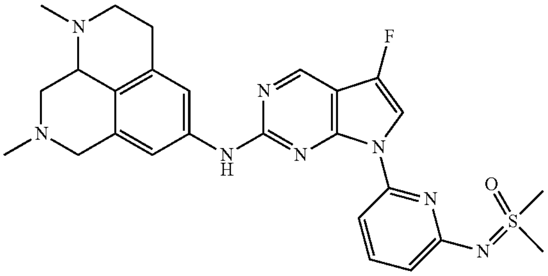
44
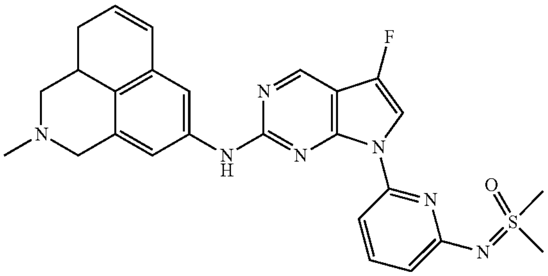

-continued
45
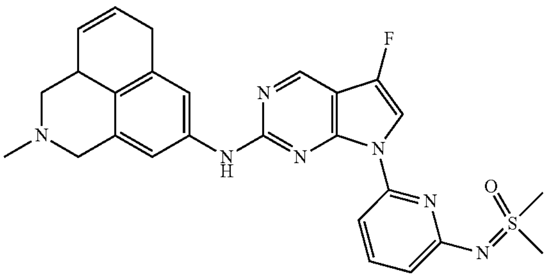
46
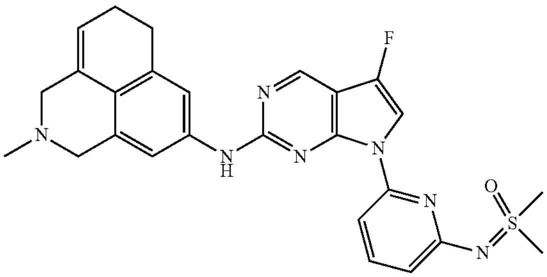
47
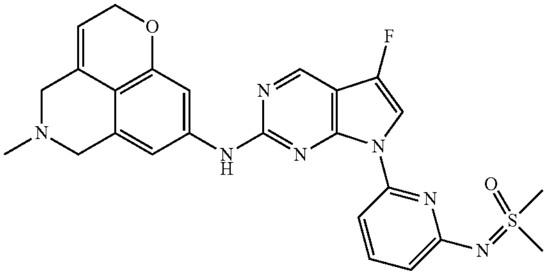
48
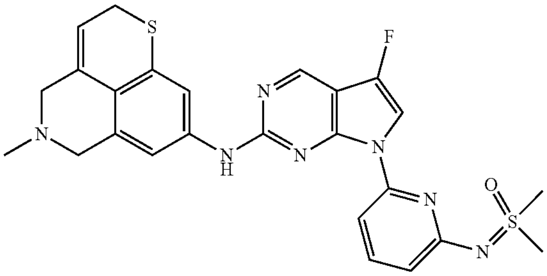
49
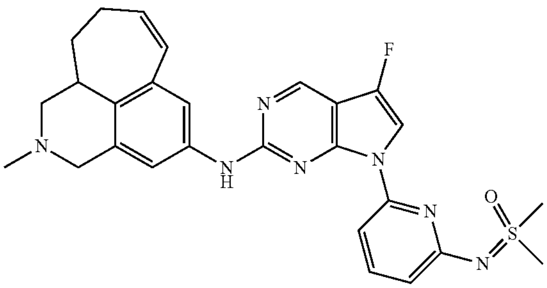
-continued
50
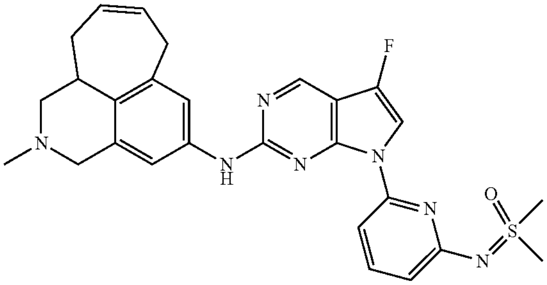
51
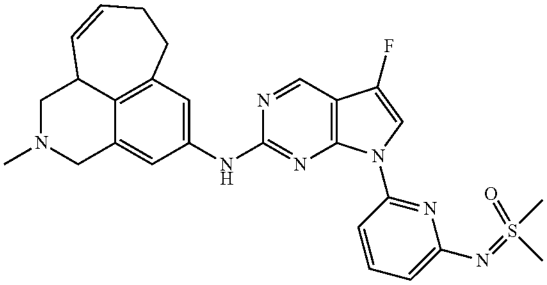
52
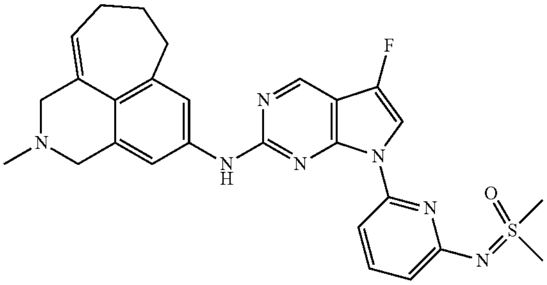
53
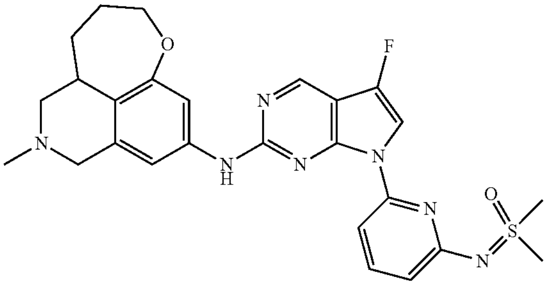
54
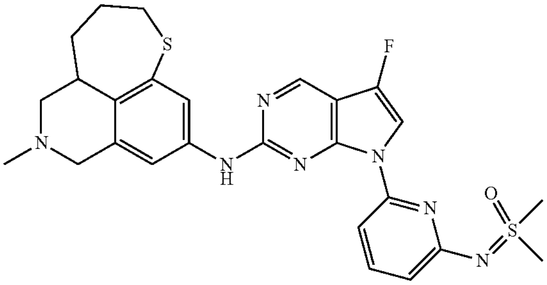

-continued
55
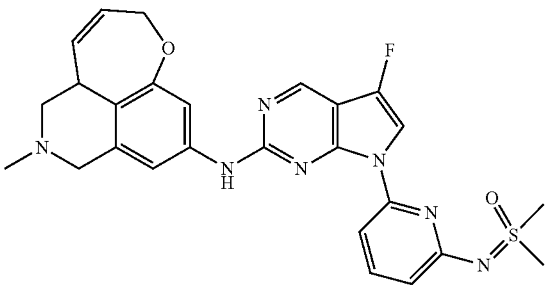
56
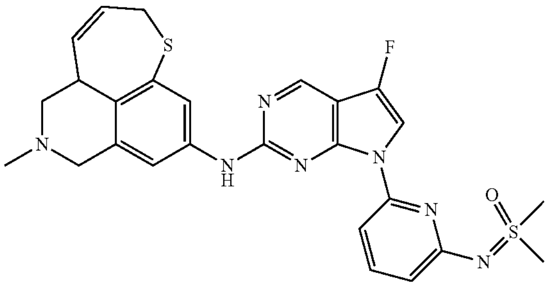
57
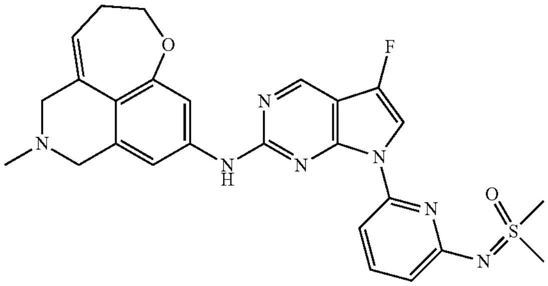
58
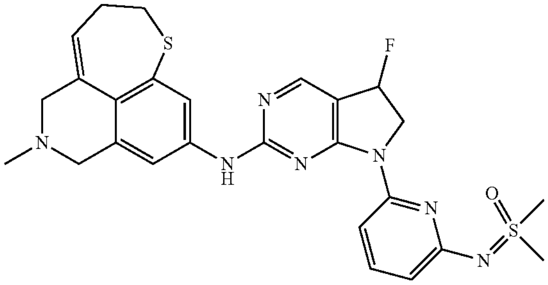
59
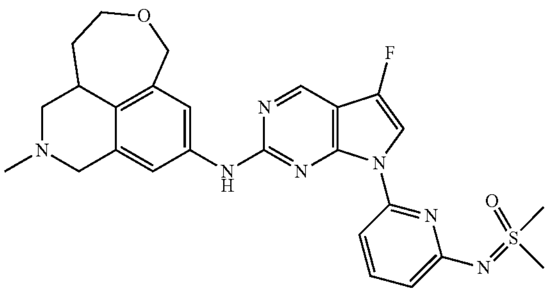
-continued
60
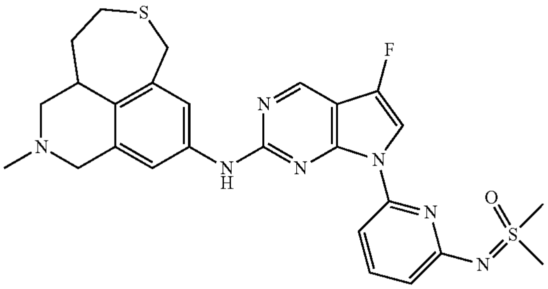
61
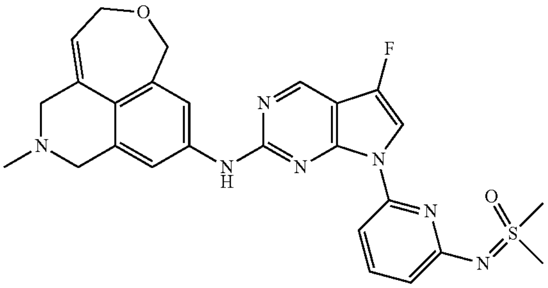
62
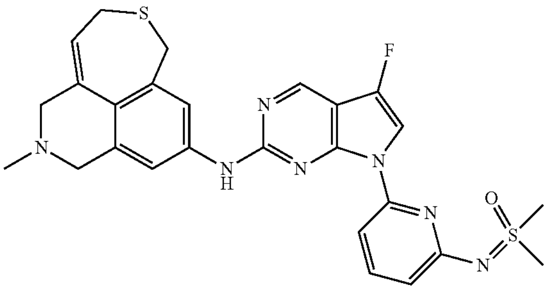
63
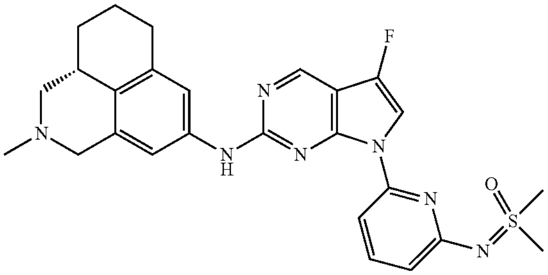
64
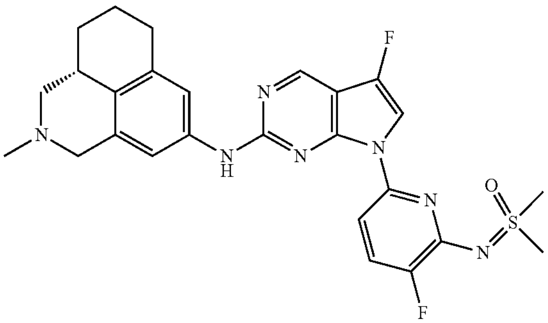

-continued

65

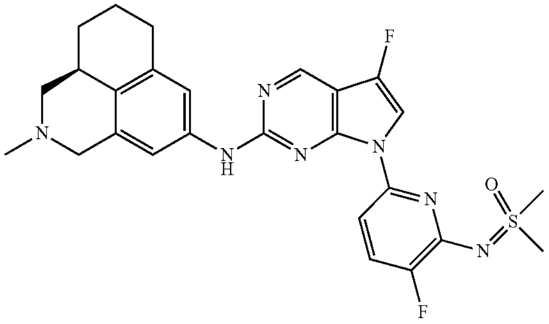

66

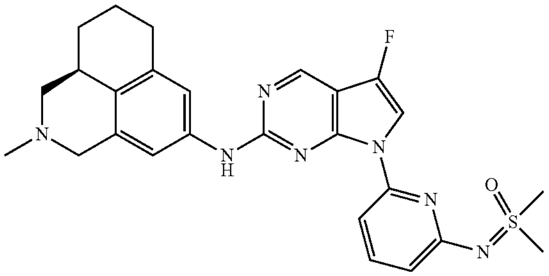

67

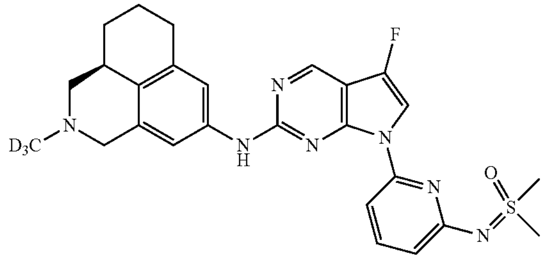

68

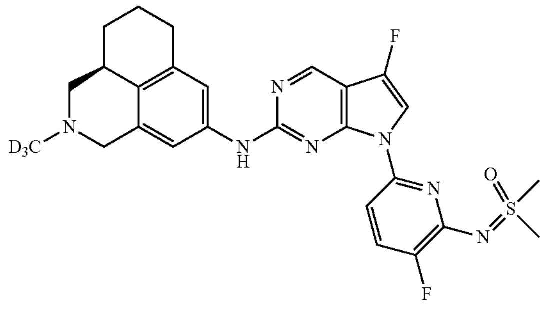

69

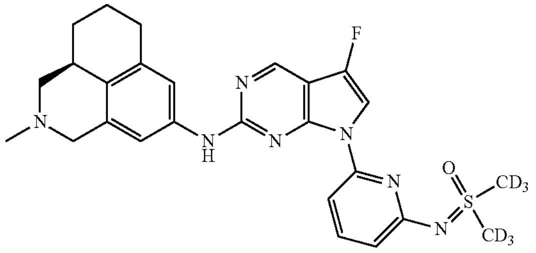

or

-continued

70

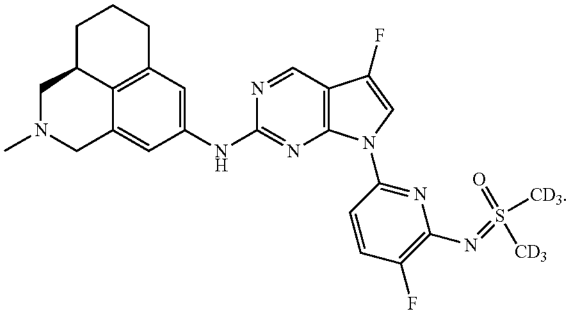

Another object of the present invention is to provide a pharmaceutical composition comprising a pharmaceutically acceptable carrier, diluent and/or excipient, and the compound of general formula (1) or general formula (1A) or the isomer, the crystalline form, the pharmaceutically acceptable salt, the hydrate or the solvate thereof of the present invention as an active ingredient. Yet another object of the present invention is to provide use of the compound of general formula (1) or the isomer, the crystalline form, the pharmaceutically acceptable salt, the hydrate or the solvate thereof of the present invention or the pharmaceutical composition described above in the preparation of a medicament for treating, regulating or preventing diseases mediated by Wee-Yet another object of the present invention is to provide a method for treating, regulating or preventing related diseases mediated by Wee-1, comprising administering to a subject a therapeutically effective amount of the compound of general formula (1) or the isomer, the crystalline form, the pharmaceutically acceptable salt, the hydrate or the solvate thereof of the present invention or the pharmaceutical composition described above.

Through sufficient research, the inventor discovered that a fused cyclic compound with the structure of formula (1) has strong inhibitory activity on Wee-1 and combined administration activity with a chemotherapeutic drug, gemcitabine (GMC), and the results show that the compound of the present invention can have a better effect when being in combination with chemotherapeutic drugs clinically.

It should be understood that both the above-mentioned general description and the following detailed description of the present invention are exemplary and explanatory, and are intended to provide further explanation of the present invention claimed.

Synthesis of Compounds

Methods for preparing the compounds of general formula (1) of the present invention are specifically described below, but these specific methods do not limit the present invention in any way.

The compounds of general formula (1) described above can be synthesized using standard synthetic techniques or well-known techniques in combination with the methods described herein. In addition, solvents, temperatures and other reaction conditions mentioned herein may vary. Starting materials for the synthesis of the compounds can be obtained synthetically or commercially. The compounds described herein and other related compounds with different substituents can be synthesized by using well-known techniques and starting materials, including the methods found in March, Advanced Organic Chemistry, $4^{th}$ Ed., (Wiley 1992); Carey and Sundberg, Advanced Organic Chemistry, $4^{th}$ Ed., Vols. A and B (Plenum 2000, 2001); and Green and Wuts, Protective Groups in Organic Synthesis, $3^{rd}$ Ed., (Wiley 1999). General methods for preparing the compounds can be modified by using appropriate reagents and conditions for introducing different groups into the molecular formulas provided herein.

In one aspect, the compounds described herein are prepared according to methods well known in the art. However, the conditions of the methods, such as reactants, solvents, bases, the amount of the compounds used, reaction temperature and time required for the reaction are not limited to the following explanation. The compounds of the present invention can also be conveniently prepared by optionally combining various synthetic methods described herein or known in the art, and such combinations can be easily carried out by those skilled in the art to which the present invention pertains. In one aspect, the present invention further provides a method for preparing the compound of general formula (1), wherein the compound of general formula (1) can be prepared using method A below:

Method A comprises the following steps: firstly, subjecting a compound A1 to a coupling reaction with a compound A2 to generate a compound A3, and further subjecting the compound A3 to a reaction with a compound B7 to generate a target compound A5.

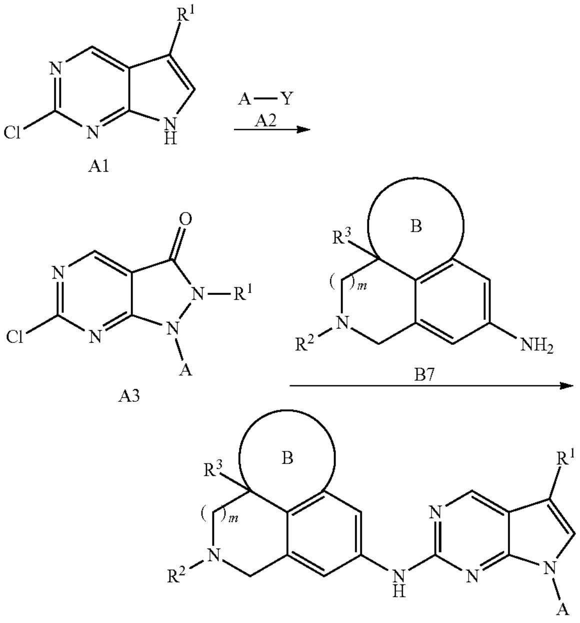

A1

A3

(1)

In the reaction equation described above, A, B, $R^1$, $R^2$, $R^3$ and m are as defined above, and Y is Br, I or —$B(OH)_2$.

Further Forms of Compounds

"Pharmaceutically acceptable" herein means a substance, such as a carrier or a diluent, which will not lead to loss of biological activity or properties of a compound and is relatively non-toxic. For example, when an individual is given a substance, the substance will not cause undesired biological effects or interact with any component contained therein in a deleterious manner.

The term "pharmaceutically acceptable salt" means an existing form of a compound, that does not cause significant irritation to the organism receiving the administration or eliminate the biological activity and properties of the compound. In certain specific aspects, the pharmaceutically acceptable salt is obtained by subjecting the compound of general formula (1) to a reaction with acids, e.g., inorganic acids such as hydrochloric acid, hydrobromic acid, hydrofluoric acid, sulfuric acid, phosphoric acid, nitric acid, carbonic acid and the like, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid, p-toluenesulfonic acid and the like, and acidic amino acids such as aspartic acid, glutamic acid and the like.

It should be understood that references to pharmaceutically acceptable salts include solvent addition forms or crystalline forms, especially solvates or polymorphs. A solvate contains either stoichiometric or non-stoichiometric amount of solvent and is selectively formed during crystallization in a pharmaceutically acceptable solvent such as water and ethanol. Hydrates are formed when the solvent is water, or alcoholates are formed when the solvent is ethanol. The solvates of the compound of general formula (1) are conveniently prepared or formed according to the methods described herein. For example, hydrates of the compound of general formula (1) are conveniently prepared by recrystallization in a mixed solvent of water/organic solvent, wherein the organic solvent used includes, but is not limited to, tetrahydrofuran, acetone, ethanol, or methanol. In addition, the compounds described herein may be present in either a non-solvated form or a solvated form. In general, the solvated forms are considered equivalent to the non-solvated forms for purposes of the compounds and methods provided herein.

In other specific examples, the compound of general formula (1) is prepared in different forms including, but not limited to, amorphous, pulverized, and nanoparticle forms. In addition, the compound of general formula (1) includes crystalline forms, but may also be polymorphs. Polymorphs include different lattice arrangements of the same elements of a compound. The polymorphs generally have different X-ray diffraction spectra, infrared spectra, melting points, density, hardness, crystalline forms, optical and electrical properties, stability and solubility. Different factors such as a recrystallization solvent, crystallization rate and storage temperature may lead to a single dominant crystalline form.

In another aspect, the compound of general formula (1) may have a chiral center and/or axial chirality, and thus may be present in the form of a racemate, a racemic mixture, a single enantiomer, a diastereomeric compound, a single diastereomer, and a cis-trans isomer. Each chiral center or axial chirality will independently produce two optical isomers, and all possible optical isomers, diastereomeric mixtures and pure or partially pure compounds are included within the scope of the present invention. The present invention is meant to include all such isomeric forms of these compounds.

The compound of the present invention may contain unnatural proportions of atomic isotopes at one or more of the atoms that constitute the compound. For example, the compound may be labeled with radioactive isotopes, such as tritium ($^3H$), iodine-125 ($^{121}I$) and C-14 ($^{14}C$). For another example, deuterium can be used to substitute a hydrogen atom to form a deuterated compound. The bond formed by deuterium and carbon is stronger than that formed by ordinary hydrogen and carbon. Compared with an undeuterated medicament, the deuterated medicament generally has the advantages of reduced adverse effects, increased medicament stability, enhanced efficacy, prolonged in vivo half-life and the like. All isotopic variations of the compound of the present invention, whether radioactive or not, are contained within the scope of the present invention.

Terminology

Unless otherwise stated, the terms used in the present invention, including those in the specification and claims, are defined as follows. It must be noted that in the specification and the appended claims, the singular forms "a" and "an" include plural meanings unless clearly indicated otherwise. Unless otherwise stated, conventional methods for mass, spectrometry, nuclear magnetic resonance spectroscopy, HPLC, protein chemistry, biochemistry, recombinant DNA technology and pharmacology are used. As used herein, "or" or "and" used refers to "and/or" unless otherwise stated.

Unless otherwise specified, "alkyl" refers to a saturated aliphatic hydrocarbon group, including linear and branched groups containing 1 to 6 carbon atoms. Lower alkyl groups containing 1 to 4 carbon atoms, such as methyl, ethyl, propyl, 2-propyl, n-butyl, isobutyl or tert-butyl, are preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH_2$, $CF_3(CH_3)CH$, $^{i}$Pr, $^{n}$Pr, $^{i}$Bu, $^{n}$Bu or $^{t}$Bu.

Unless otherwise specified, "alkylene" refers to a divalent alkyl as defined above. Examples of alkylene include, but are not limited to, methylene and ethylene.

Unless otherwise specified, "alkenyl" refers to an unsaturated aliphatic hydrocarbon group containing carbon-carbon double bonds, including linear or branched groups containing 1 to 14 carbon atoms. Lower alkenyl groups containing 1 to 4 carbon atoms, such as vinyl, 1-propenyl, 1-butenyl, or 2-methylpropenyl, are preferred.

Unless otherwise specified, "alkynyl" refers to an unsaturated aliphatic hydrocarbon group containing carbon-carbon triple bonds, including linear and branched groups containing 1 to 14 carbon atoms. Lower alkynyl groups containing 1 to 4 carbon atoms, such as ethynyl, 1-propynyl, or 1-butynyl, are preferred.

Unless otherwise specified, "cycloalkyl" refers to a non-aromatic hydrocarbon ring system (monocyclic, bicyclic or polycyclic), and partially unsaturated cycloalkyl may be referred to as "cycloalkenyl" if the carbocyclic ring contains at least one double bond, or "cycloalkynyl" if the carbocyclic ring contains at least one triple bond. The cycloalkyl may include monocyclic or polycyclic groups and spiro rings (e.g., having 2, 3 or 4 fused rings). In some embodiments, the cycloalkyl is monocyclic. In some embodiments, the cycloalkyl is monocyclic or bicyclic. The ring carbon atoms of the cycloalkyl may optionally be oxidized to form an oxo or sulfido group. The cycloalkyl further includes cycloalkylene. In some embodiments, the cycloalkyl contains 0, 1 or 2 double bonds. In some embodiments, the cycloalkyl contains 1 or 2 double bonds (partially unsaturated cycloalkyl). In some embodiments, the cycloalkyl may be fused to aryl, heteroaryl, cycloalkyl and heterocycloalkyl. In some embodiments, the cycloalkyl may be fused to aryl, cycloalkyl and heterocycloalkyl. In some embodiments, the cycloalkyl may be fused to aryl and heterocycloalkyl. In some embodiments, the cycloalkyl may be fused to aryl and cycloalkyl. Examples of the cycloalkyl include cyclopropyl, cyclobutyl, cyclopentyl, cyclohexyl, cycloheptyl, cyclopentenyl, cyclohexenyl, cyclohexadienyl, cycloheptatrienyl, norcamphanyl, norpinanyl, norcarnyl, bicyclo[1.1.1]pentyl, bicyclo[2.1.1]hexyl and the like.

Unless otherwise specified, "alkoxy" refers to an alkyl group that bonds to the rest of the molecule through an ether oxygen atom. Representative alkoxy groups are those having 1-6 carbon atoms, such as methoxy, ethoxy, propoxy, isopropoxy, butoxy, isobutoxy, sec-butoxy and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^{i-}$PrO, $^{n-}$PrO, $^{i-}$BuO, $^{n-}$fBuO or $^{t-}$BuO.

Unless otherwise specified, "heterocycloalkyl" refers to a non-aromatic ring or ring system, which may optionally contain one or more alkenylene as part of the ring structure, having at least one heteroatom ring member independently selected from boron, phosphorus, nitrogen, sulfur, oxygen, and phosphorus. Partially unsaturated heterocycloalkyl may be referred to as "heterocycloalkenyl" if heterocycloalkyl contains at least one double bond, or "heterocycloalkynyl" if the heterocycloalkyl contains at least one triple bond. Heterocycloalkyl may include monocyclic, bicyclic, spiro ring, or polycyclic systems (e.g., having two fused or bridged rings). In some embodiments, heterocycloalkyl is a monocyclic group having 1, 2, or 3 heteroatoms independently selected from nitrogen, sulfur, and oxygen. The ring carbon atoms and heteroatoms of heterocycloalkyl may optionally be oxidized to form oxo or sulfido groups or other oxidized bonds (e.g., C(O), S(O), C(S) or S(O)2, N-oxides, etc.), or the nitrogen atoms may be quaternized. Heterocycloalkyl may be attached via a ring carbon atom or a ring heteroatom. In some embodiments, heterocycloalkyl contains 0 to 3 double bonds. In some embodiments, heterocycloalkyl contains 0 to 2 double bonds. The definition of heterocycloalkyl further includes moieties having one or more aromatic rings fused to (i.e., sharing a bond with) the heterocycloalkyl ring, for example, benzo-derivatives of piperidine, morpholine, azepin, thienyl, or the like. Heterocycloalkyl containing a fused aromatic ring may be attached via any ring atom, including ring atoms of the fused aromatic ring. Examples of heterocycloalkyl include, but are not limited to, azetidinyl, azepinyl, dihydrobenzofuranyl, dihydrofuranyl, dihydropyranyl, N-morpholinyl, 3-oxa-9-azaspiro[5.5]undecyl, 1-oxa-8-azaspiro[4.5]decyl, piperidinyl, piperazinyl, oxopiperazinyl, pyranyl, pyrrolidinyl, quininyl, tetrahydrofuranyl, tetrahydropyranyl, 1,2,3,4-tetrahydroquinolinyl, tropanyl, 4,5,6,7-tetrahydrothiazolo[5,4-c]pyridinyl, 4,5,6,7-tetrahydro-1H-imidazo[4,5-c]pyridine, N-methylpiperidinyl, tetrahydroimidazolyl, pyrazolidinyl, butyrolactam, valerolactam, imidazolidinonyl, hydantoinyl, dioxolanyl, phthalimidyl, pyrimidine-2,4(1H,3H)-dione, 1,4-dioxanyl, morpholinyl, thiomorpholinyl, thiomorpholinyl-S-oxide, thiomorpholinyl-S,S-oxide, piperazinyl, pyranyl, pyridonyl, 3-pyrrolinyl, thiopyranyl, pyronyl, tetrahydrothienyl, 2-azaspiro[3.3]heptanyl, indolinyl,

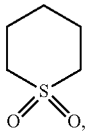,
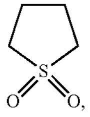,
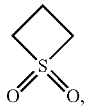,
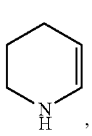,

-continued

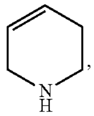, , and 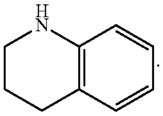.

Unless otherwise specified, "aryl" refers to an aromatic hydrocarbon group, which is monocyclic or polycyclic; for example, a monocyclic aryl ring may be fused to one or more carbocyclic aromatic groups. Examples of aryl include, but are not limited to, phenyl, naphthyl, and phenanthryl.

Unless otherwise specified, "aryloxy" refers to an aryl group that bonds to the rest of the molecule through an ether oxygen atom. Examples of aryloxy include, but are not limited to, phenoxy and naphthoxy.

Unless otherwise specified, "arylene" refers to a divalent aryl defined as above. Examples of arylene include, but are not limited to, phenylene, naphthylene, and phenanthrylene.

Unless otherwise specified, "heteroaryl" refers to an aromatic group containing one or more heteroatoms (O, S, or N), and the "heteroaryl" is monocyclic or polycyclic. For example, a monocyclic heteroaryl ring is fused to one or more carbocyclic aromatic groups or other monocyclic heterocycloalkyl groups. Examples of heteroaryl include, but are not limited to, pyridinyl, pyridazinyl, imidazolyl, pyrimidinyl, pyrazolyl, triazolyl, pyrazinyl, quinolinyl, isoquinolinyl, furanyl, thienyl, isoxazolyl, thiazolyl, oxazolyl, isothiazolyl, pyrrolyl, indolyl, benzimidazolyl, benzofuranyl, benzothiazolyl, benzothienyl, benzoxazolyl, benzopyridinyl, pyrrolopyrimidinyl, 1H-pyrrolo[3,2-b]pyridinyl, 1H-pyrrolo[2,3-c]pyridinyl, 1H-pyrrolo[3,2-c]pyridinyl, 1H-pyrrolo[2,3-b]pyridinyl,

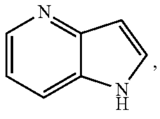, 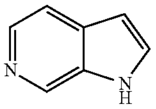, 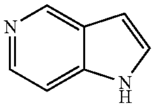, and

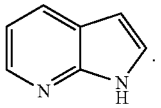.

Unless otherwise specified, "halogen" (or halo) refers to fluorine, chlorine, bromine or iodine. The term "halo" (or "halogenated") before a group name indicates that the group is partially or fully halogenated, that is, substituted in any combination with F, Cl, Br or I, preferably with F or Cl.

"Optional" or "optionally" means that the subsequently described event or circumstance may, but does not necessarily, occur, and the description includes instances where the event or circumstance occurs and instances where the event or the circumstance does not occur.

The substituent "$—O—CH_2—O—$" means that two oxygen atoms in the substituent are linked to two adjacent carbon atoms in the heterocycloalkyl, aryl or heteroaryl, for example:

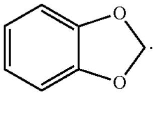.

When the number of a linker group is 0, such as $—(CH_2)_0—$, it means that the linker group is a single bond.

When one of the variables is selected from a chemical bond, it means that the two groups linked by this variable are linked directly. For example, when L in X-L-Y represents a chemical bond, it means that the structure is actually X-Y.

The term "membered ring" includes any cyclic structure. The term "membered" is intended to refer to the number of backbone atoms that form a ring. For example, cyclohexyl, pyridinyl, pyranyl and thiopyranyl are six-membered rings, and cyclopentyl, pyrrolyl, furanyl and thienyl are five-membered rings.

The term "moiety" refers to a specific portion or functional group of a molecule. A chemical moiety is generally considered to be a chemical entity contained in or attached to the molecule. Unless otherwise stated, a wedged solid bond ( ) and a wedged dashed bond ( ) represent the absolute configuration of a stereogenic center, and a straight solid bond ( ) and a straight dashed bond ( ) represent the relative configuration of the stereogenic center. A wavy line ( ) represents a wedged solid bond ( ) or a wedged dashed bond ( ), or a wavy line ( ) represents a straight solid bond ( ) or a straight dashed bond ( ).

Unless otherwise stated, a single bond or a double bond is represented by .

Specific Pharmaceutical and Medical Terminology

The term "acceptable", as used herein, means that a formulation component or an active ingredient does not unduly and adversely affect a general therapeutic target's health.

The terms "treatment," "treatment course" and "therapy", as used herein, include alleviating, inhibiting or improving a symptom or condition of a disease; inhibiting the development of complications; improving or preventing underlying metabolic syndrome; inhibiting the development of a disease or symptom, e.g., controlling the progression of a disease or condition; alleviating a disease or symptom; leading to disease or symptom regression; and alleviating a complication caused by a disease or symptom, or preventing or treating a sign caused by a disease or symptom. As used herein, a compound or pharmaceutical composition, when administered, can improve a disease, a symptom or a condition, which particularly means improving the severity, delaying the onset, slowing the progression, or reducing the duration of the disease. Fixed or temporary administration, or continuous or intermittent administration, may be attributed to or associated with the administration.

"Active ingredient" refers to the compound of general formula (1), and pharmaceutically acceptable inorganic or organic salts of the compound of general formula (1). The compound of the present invention may contain one or more asymmetric centers (chiral center or axial chirality) and thus occur in the form of a racemate, a racemic mixture, a single enantiomer, a diastereomeric compound and a single diastereomer. Asymmetric centers that may be present depend on the nature of the various substituents on the molecule. Each of such asymmetric centers will independently produce two optical isomers, and all possible optical isomers, diastereomeric mixtures and pure or partially pure compounds are included within the scope of the present invention. The present invention is meant to include all such isomeric forms of these compounds.

The terms such as "compound", "composition", "agent" or "medicine or medicament" are used interchangeably herein and all refer to a compound or composition that, when administered to an individual (human or animal), can induce a desired pharmacological and/or physiological response by local and/or systemic action.

The term "administered, administering or administration" herein means the direct administration of the compound or the composition, or the administration of a prodrug, a derivative, an analog or the like of the active compound.

Although the numerical ranges and parameters defining the broad scope of the present invention are approximations, the related numerical values set forth in the specific examples have been presented herein as precisely as possible. Any numerical value, however, inherently contains a standard deviation necessarily resulting from certain methods for testing. Herein, "about" generally means that the actual value is within a particular value or range ±10%, 5%, 1% or 0.5%. Alternatively, the term "about" indicates that the actual numerical value falls within the acceptable standard error of a mean, as considered by those skilled in the art. All ranges, quantities, numerical values and percentages used herein (e.g., to describe an amount of a material, a length of time, a temperature, an operating condition, a quantitative ratio and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At least, these numerical parameters should be understood as the significant digits indicated or the numerical values obtained using conventional rounding rules.

Unless otherwise defined in the specification, the scientific and technical terms used herein have the same meaning as commonly understood by those skilled in the art. In addition, nouns in their singular forms used in the specification encompass their plural forms, unless contradicted by context; and nouns in their plural forms used also encompass their singular forms.

Therapeutic Use

The compounds or compositions provided by the present invention are generally useful for inhibiting Wee-1 kinase, and thus may be useful for treating one or more disorders related to Wee-1 kinase activity. Therefore, in certain embodiments, the present invention provides a method for treating a disorder mediated by Wee-1 kinase, which comprises the step of administering to a patient in need thereof the compound of the present invention or the pharmaceutically acceptable composition thereof.

Cancers that can be treated with the compound of the present invention include, but are not limited to, hematological malignancies (leukemias, lymphomas, myelomas including multiple myeloma, myelodysplastic syndrome and myeloproliferative syndrome), solid tumors (carcinomas such as prostate, breast, lung, colon, pancreas, kidney, ovary and soft tissue carcinomas, osteosarcoma and interstitial tumors), and the like.

Route of Administration

The compound and the pharmaceutically acceptable salt thereof of the present invention can be made into various formulations including a safe and effective amount of the compound or the pharmaceutically acceptable salt thereof of the present invention, and a pharmaceutically acceptable excipient or carrier, wherein the "safe and effective amount" means that the amount of the compound is sufficient to significantly improve the condition without causing serious adverse effects. The safe and effective amount of the compound is determined according to the age, condition, course of treatment and other specific conditions of a treated subject. "Pharmaceutically acceptable excipient or carrier" refers to one or more compatible solid or liquid fillers or gel substances that are suitable for human use and must be of sufficient purity and sufficiently low toxicity. "Compatible" herein means that the components of the composition can intermix with the compound of the present invention and with each other, without significantly reducing the pharmaceutical efficacy of the compound. Examples of pharmaceutically acceptable excipients or carriers include cellulose and derivatives thereof (e.g., sodium carboxymethylcellulose, sodium ethylcellulose or cellulose acetate), gelatin, talc, solid lubricants (e.g., stearic acid or magnesium stearate), calcium sulfate, vegetable oil (e.g., soybean oil, sesame oil, peanut oil or olive oil), polyols (e.g., propylene glycol, glycerol, mannitol or sorbitol), emulsifiers (e.g., Tween®), wetting agents (e.g., sodium lauryl sulfate), colorants, flavoring agents, stabilizers, antioxidants, preservatives, pyrogen-free water and the like. When the compound of the present invention is administered, it may be administered orally, rectally, parenterally (intravenously, intramuscularly or subcutaneously) or topically.

Solid dosage forms for oral administration include capsules, tablets, pills, pulvises and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol and silicic acid; (b) binders, such as hydroxymethyl cellulose, alginate, gelatin, polyvinylpyrrolidone, sucrose and acacia; (c) humectants, such as glycerol; (d) disintegrants, such as agar, calcium carbonate, potato starch or tapioca starch, alginic acid, certain complex silicates and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets and pills, the dosage forms may further include buffers.

Solid dosage forms such as tablets, dragees, capsules, pills and granules may be prepared using coatings and shells such as enteric coatings and other materials well known in the art. They may include opacifying agents, and the active compound or compound in such composition may be released in a certain part of the digestive tract in a delayed manner. Examples of embedding components that can be used are polymeric substances and wax-based substances. If necessary, the active compound can also be in microcapsule form with one or more of the excipients described above.

Liquid dosage forms for oral administration include pharmaceutically acceptable emulsions, solutions, suspensions, syrups or elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil, or mixtures of these substances.

Besides such inert diluents, the composition may further comprise adjuvants, such as wetting agents, emulsifiers, suspending agents, sweeteners, flavoring agents and perfuming agents.

In addition to the active compound, the suspensions may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents or excipients include water, ethanol, polyols and suitable mixtures thereof.

Dosage forms for topical administration of the compound of the present invention include ointments, pulvises, patches, sprays and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds. When the pharmaceutical composition is used, a safe and effective amount of the compound of the present invention is administered to a mammal (such as a human) to be treated, wherein the dose of administration is a pharmaceutically effective dose. For a human of 60 kg, the daily dose of administration is usually 1-2000 mg, preferably 50-1000 mg. Certainly, in a specific dose, such factors as the route of administration, the health condition of the patient and the like will also be considered, which are well known to skilled physicians.

The features mentioned in the present invention or those mentioned in the examples may be combined arbitrarily. All the features disclosed in this specification may be used with any composition form and the various features disclosed in this specification may be replaced with any alternative features that provide the same, equivalent or similar purpose. Thus, unless otherwise specified, the features disclosed herein are merely general examples of equivalent or similar features.

DETAILED DESCRIPTION

Various specific aspects, features and advantages of the compounds, methods and pharmaceutical compositions described above will be set forth in detail in the following description, which will make the content of the present invention very clear. It should be understood that the detailed description and examples below describe specific examples for reference only. After reading the description of the present invention, those skilled in the art can make various changes or modifications to the present invention, and such equivalents also fall within the scope of the present application defined herein.

In all examples, melting points were measured using an X-4 melting point apparatus with the thermometer uncalibrated; $^{1}$H-NMR spectra were recorded with a Varian Mercury 400 nuclear magnetic resonance spectrometer, and chemical shifts are expressed in S (ppm); silica gel for separation was 200-300 mesh silica gel if not specified, and the ratio of the eluents was a volume ratio.

The following abbreviations are used in the present invention: $CDCl_3$ represents deuterated chloroform; CuI represents cuprous iodide; DCM represents dichloromethane; dioxane represents 1,4-dioxane; DMF represents N,N-dimethylformamide; EA represents ethyl acetate; EtOH represents ethanol; h represents hour; $H_2$ represents hydrogen; $H_2SO_4$ represents sulfuric acid; $K_2CO_3$ represents potassium carbonate; $KNO_3$ represents potassium nitrate; LC-MS represents liquid chromatography-mass spectrometry; $LiAlH_4$ represents lithium aluminum hydride; mL represents milliliter; MeOH represents methanol; min represents minute; MS represents mass spectrometry; $^{n}$BuLi represents n-butyllithium; NMR represents nuclear magnetic resonance; ° C. represents degree Celsius; $Pd_2(dba)_3$ represents tris(dibenzylideneacetone)dipalladium; PE represents petroleum ether; r.t. represents room temperature; Xantphos represents 4,5-bis(diphenylphosphino)-9,9-dimethylxanthene; TEA represents triethylamine; TFA represents trifluoroacetic acid; THE represents tetrahydrofuran; $T_3P$ represents propylphosphoric anhydride.

Preparation Example 1. Preparation of N-(6-(2-chloro-5-fluoro-7H-pyrrolo[2,3-d]pyrimidin-7-yl) pyridin-2-yl)methanesulfonamide

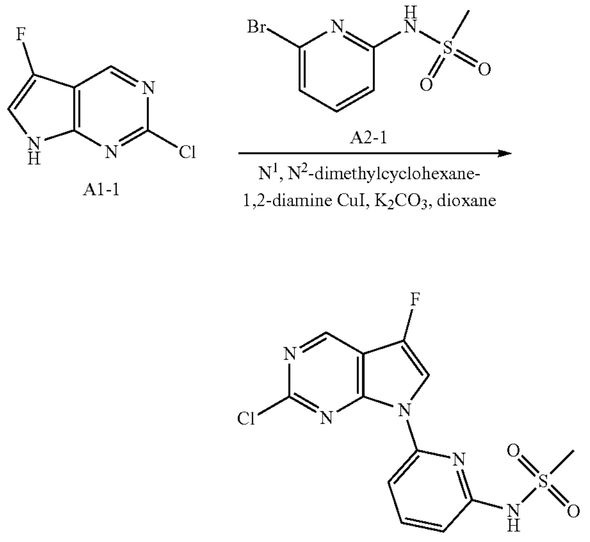

A3-1

2-Chloro-5-fluoro-7H-pyrrolo[2,3-d]pyrimidine (200 mg, 1.17 mmol), N-(6-bromopyridin-2-yl)methanesulfonamide (310 mg, 1.17 mmol), CuI (230 mg, 1.17 mmol), $K_2CO_3$ (240 mg, 1.75 mmol), 1,4-dioxane (12 mL), and $N^1$,$N^2$-dimethylcyclohexane-1,2-diamine (190 mg, 1.29 mmol) were added into a 100 mL round-bottom flask in sequence under Ar atmosphere. The mixture was reacted at 100° C. for 2 h. LC-MS monitoring showed that the reaction was complete. The reaction mixture was purified through a reversed-phase column to give a solid product (308 mg, 77% yield), LC-MS: 342.0 $[M+H]^+$.

Intermediates A3-2 to A3-27 could be obtained by using different starting materials according to the synthesis for the intermediate A3-1.

TABLE 1
| Structural formulas of intermediates A3-2 to A3-27 | | | | | |
|---|---|---|---|---|---|
| Intermediate | Structure | MS [M + H]+ | Intermediate | Structure | MS [M + H]+ |
| A3-2 | 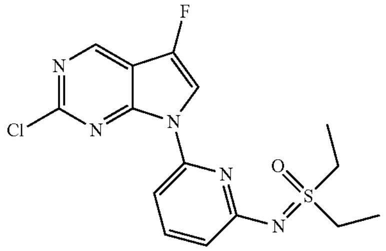 [SMILES: CCS(=O)(CC)=Nc1cccc(-n2cc(F)c3cnc(Cl)nc32)n1] | 380.1 | A3-3 | 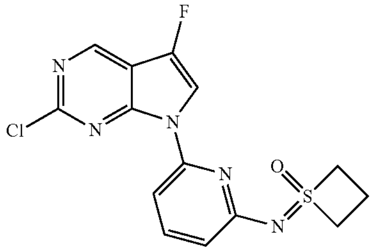 [SMILES: O=S1(=Nc2cccc(-n3cc(F)c4cnc(Cl)nc43)n2)CCC1] | 352.1 |
| A3-4 | 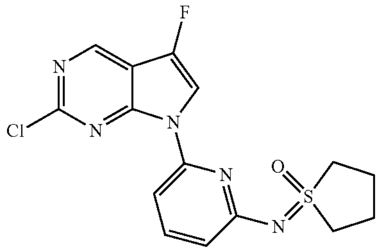 [SMILES: O=S1(=Nc2cccc(-n3cc(F)c4cnc(Cl)nc43)n2)CCCC1] | 366.1 | A3-5 | 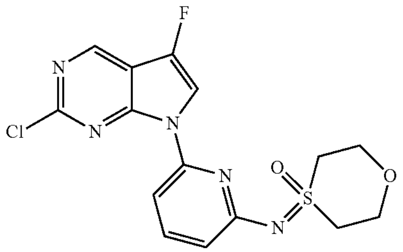 [SMILES: O=S1(=Nc2cccc(-n3cc(F)c4cnc(Cl)nc43)n2)CCOCC1] | 382.1 |
| A3-6 | 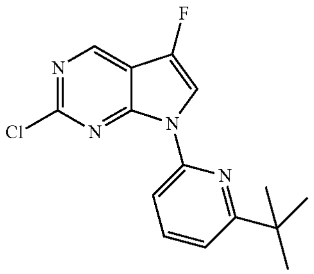 [SMILES: CC(C)(C)c1cccc(-n2cc(F)c3cnc(Cl)nc32)n1] | 305.1 | A3-7 | 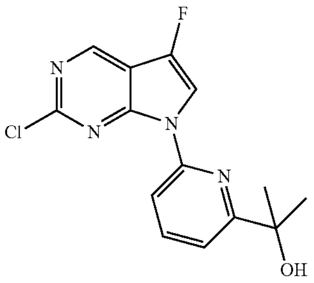 | 307.1 |
| A3-8 | 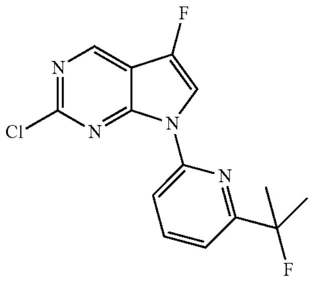 [SMILES: CC(C)(F)c1cccc(-n2cc(F)c3cnc(Cl)nc32)n1] | 309.1 | A3-9 | 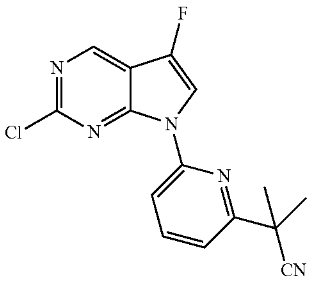 [SMILES: CC(C)(C#N)c1cccc(-n2cc(F)c3cnc(Cl)nc32)n1] | 316.1 |
| A3-10 | 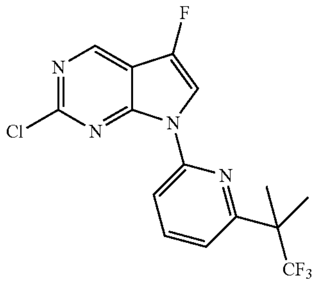 [SMILES: CC(C)(c1cccc(-n2cc(F)c3cnc(Cl)nc32)n1)C(F)(F)F] | 359.1 | A3-11 | 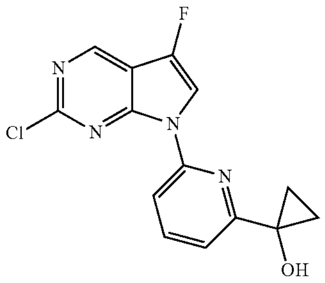 [SMILES: OC1(c2cccc(-n3cc(F)c4cnc(Cl)nc43)n2)CC1] | 305.1 |

TABLE 1-continued
| Structural formulas of intermediates A3-2 to A3-27 | | | | | |
|---|---|---|---|---|---|
| Inter-mediate | Structure | MS [M + H]$^+$ | Inter-mediate | Structure | MS [M + H]$^+$ |
| A3-12 | 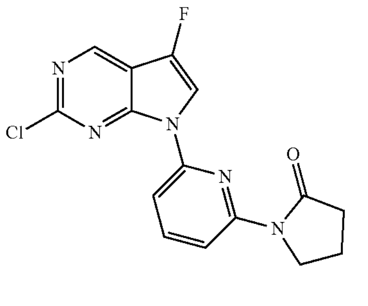 [SMILES: O=C1CCCN1c1cccc(-n2cc(F)c3cnc(Cl)nc32)n1] | 332.1 | A3-13 | 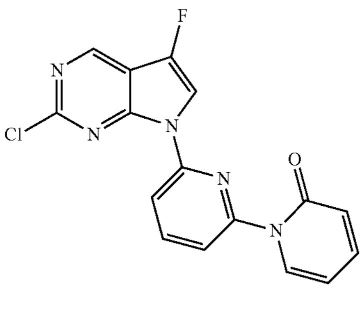 [SMILES: O=c1ccccn1-c1cccc(-n2cc(F)c3cnc(Cl)nc32)n1] | 342.1 |
| A3-14 | 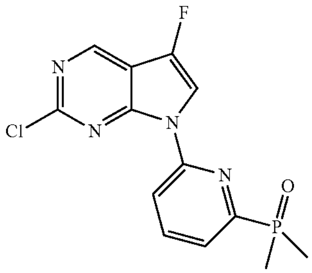 [SMILES: CP(C)(=O)c1cccc(-n2cc(F)c3cnc(Cl)nc32)n1] | 325.0 | A3-15 | 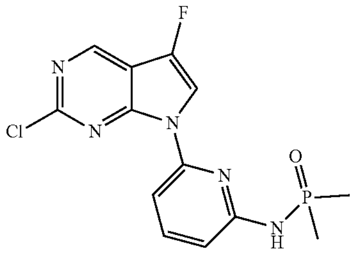 [SMILES: CP(C)(=O)Nc1cccc(-n2cc(F)c3cnc(Cl)nc32)n1] | 340.1 |
| A3-16 | 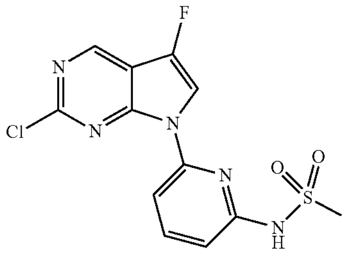 [SMILES: CS(=O)(=O)Nc1cccc(-n2cc(F)c3cnc(Cl)nc32)n1] | 342.0 | A3-17 | 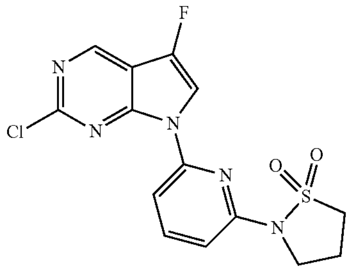 [SMILES: O=S1(=O)CCCN1c1cccc(-n2cc(F)c3cnc(Cl)nc32)n1] | 368.0 |
| A3-18 | 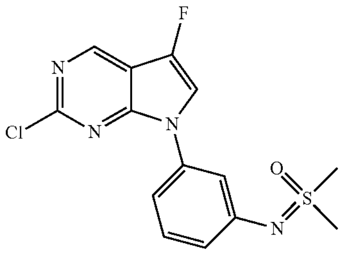 [SMILES: CS(C)(=O)=Nc1cccc(-n2cc(F)c3cnc(Cl)nc32)c1] | 339.1 | A3-19 | 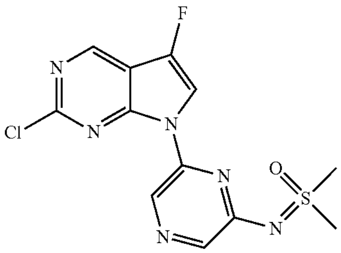 [SMILES: CS(C)(=O)=Nc1cncc(-n2cc(F)c3cnc(Cl)nc32)n1] | 341.0 |
| A3-20 | 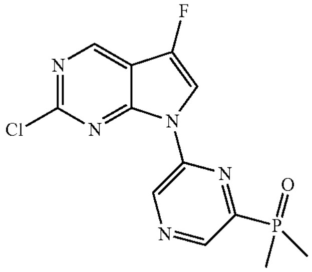 [SMILES: CP(C)(=O)c1cncc(-n2cc(F)c3cnc(Cl)nc32)n1] | 326.0 | A3-21 | 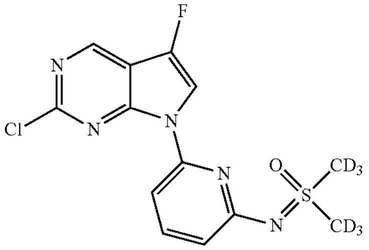 [SMILES: [2H]C([2H])([2H])S(=O)(=Nc1cccc(-n2cc(F)c3cnc(Cl)nc32)n1)C([2H])([2H])[2H]] | 346.1 |

TABLE 1-continued
Structural formulas of intermediates A3-2 to A3-27
| Inter-mediate | Structure | MS [M + H]+ | Inter-mediate | Structure | MS [M + H]+ |
|---|---|---|---|---|---|
| A3-22 | 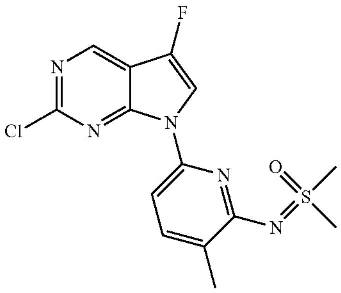 [SMILES: Cc1ccc(-n2cc(F)c3cnc(Cl)nc32)nc1N=S(C)(C)=O] | 354.1 | A3-23 | 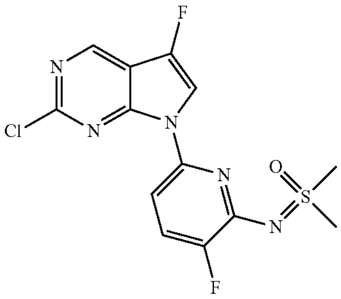 [SMILES: CS(C)(=O)=Nc1nc(-n2cc(F)c3cnc(Cl)nc32)ccc1F] | 358.1 |
| A3-24 | 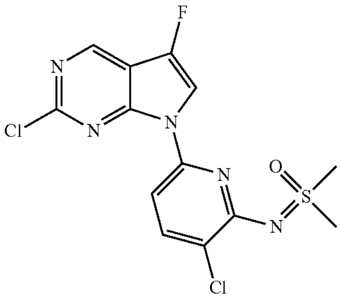 [SMILES: CS(C)(=O)=Nc1nc(-n2cc(F)c3cnc(Cl)nc32)ccc1Cl] | 374.0 | A3-25 | 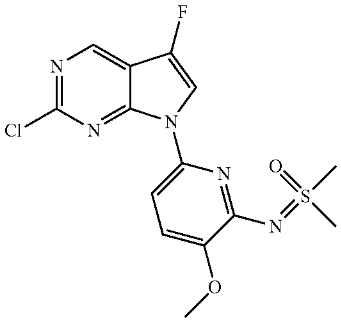 [SMILES: COc1ccc(-n2cc(F)c3cnc(Cl)nc32)nc1N=S(C)(C)=O] | 370.1 |
| A3-26 | 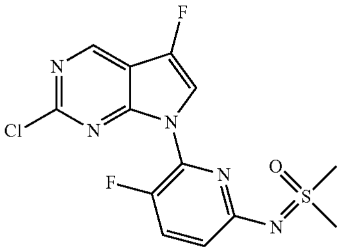 [SMILES: CS(C)(=O)=Nc1ccc(F)c(-n2cc(F)c3cnc(Cl)nc32)n1] | 358.0 | A3-27 | 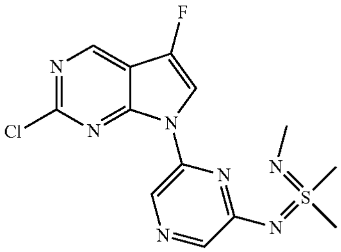 [SMILES: CN=S(C)(C)=Nc1cncc(-n2cc(F)c3cnc(Cl)nc32)n1] | 354.1 |
Preparation Example 2. Preparation of 2-methyl-2,3,7,8,9,9a-hexahydro-1H-phenylpropyl[de]isoquinoline-5-amine (intermediate B7-1)
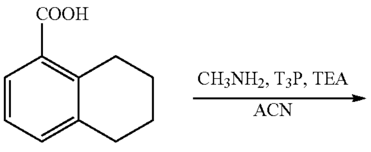
B1-1
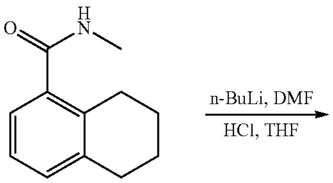
B2-1
-continued
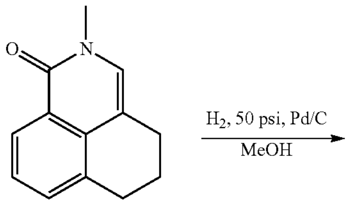
B3-1
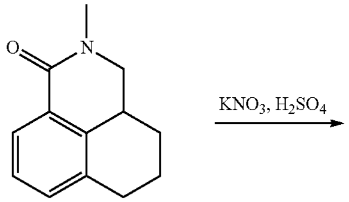
B4-1

-continued

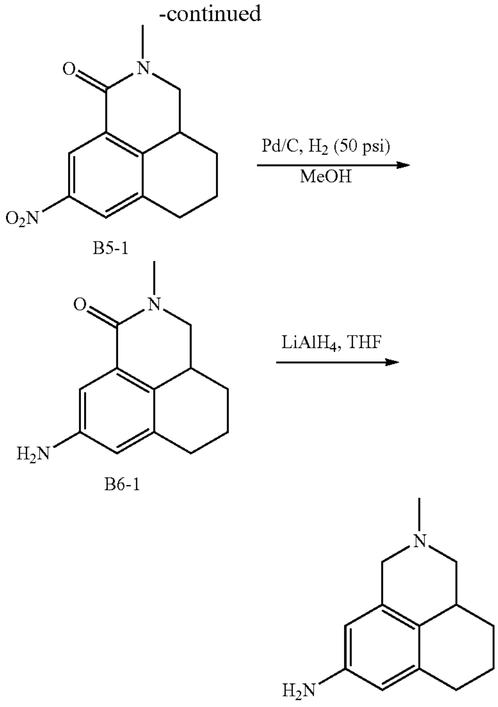

B5-1

B6-1

B7-1

Step 1: Synthesis of Compound B2-1

B1-1 (50 g, 284 mmol), methylamine hydrochloride (57.5 g, 851 mmol) and TEA (144 g, 1.42 mol, 197 mL) were dissolved in acetonitrile (600 mL), and $T_3P$ (217 g, 341 mmol, 203 mL, 50% purity) was added dropwise at room temperature. After the addition, the reaction was heated at 50° C. for 16 h. The reaction solution was diluted with 1500 mL of ethyl acetate and washed with an aqueous solution of $NaHCO_3$ (400 mL×3). The organic phase was dried over anhydrous sodium sulfate. The organic phase was filtered and distilled under reduced pressure to give a white solid (50 g, 264 mmol, 93.1% yield, crude). The crude product was directly used in the next step.

$^1$H NMR: (400 MHz, $CDCl_3$) δ: 7.12-7.01 (m, 3H), 6.10-5.71 (m, 1H), 2.93 (d, J=4.9 Hz, 3H), 2.83 (br s, 2H), 2.79-2.71 (m, 2H), 1.84-1.65 (m, 4H), MS (ESI): 190.1 [M+H]+.

Step 2: Synthesis of Compound B3-1

B2-1 (50 g, 264 mmol) was dissolved in THF (500 mL), and $^n$-BuLi (2.5 M, 275 mL) was slowly added dropwise at −23° C. under nitrogen atmosphere. Subsequently, DMF (48.3 g, 660 mmol, 50.8 mL) was slowly added dropwise at −23° C. Then a solution of HCl (6 M, 300 mL) was slowly added dropwise at 20° C. The reaction solution was diluted with water (100 mL) and extracted with ethyl acetate (500 mL×3). The organic phase was dried over anhydrous sodium sulfate. The organic phase was filtered and concentrated under reduced pressure to give a yellow solid (55 g, crude). The crude product was directly used in the next step.

$^1$H NMR: (400 MHz, $CDCl_3$) δ: 8.36-8.20 (m, 1H), 7.46-7.32 (m, 2H), 6.84 (s, 1H), 3.63-3.52 (m, 3H), 2.99-2.92 (m, 3H), 2.75-2.69 (m, 2H), 2.01-1.90 (m, 2H), MS (ESI): 200.1 [M+H]$^+$.

Step 3: Synthesis of Compound B4-1

B3-1 (55 g, 276 mmol) and 20 g of palladium on carbon were suspended in methanol (800 mL), and the suspension was stirred at 30° C. overnight under hydrogen atmosphere (50 psi). The palladium on carbon was removed by filtration, and the filtrate was concentrated under reduced pressure and purified by column chromatography ($SiO_2$, PE/EtOAc=I/O to 3/1) to give a yellow solid (38.5 g, 69.3% yield).

$^1$H NMR: (400 MHz, DMSO-$d_6$) δ: 7.71-7.62 (m, 1H), 7.28-7.20 (m, 2H), 3.42 (dd, J=5.6, 11.9 Hz, 1H), 3.25 (t, J=12.5 Hz, 1H), 3.13-2.99 (m, 4H), 2.87-2.69 (m, 2H), 2.06-1.90 (m, 2H), 1.75-1.61 (m, 1H), 1.41-1.22 (m, 1H), MS (ESI): 202.1 [M+H]$^+$.

Step 4: Synthesis of Compound B5-1

B4-1 (3.1 g, 19.2 mmol) was dissolved in $H_2SO_4$ (300 mL), and $KNO_3$ (17.9 g, 177 mmol) was slowly added at 0° C. over 3 h. After the addition, the mixture was warmed to room temperature and stirred for 2 h. TLC monitoring showed the reaction was complete. The reaction solution was diluted with 500 mL of water, and a large amount of solid precipitated. The precipitate was collected by filtration and dried to give a yellow solid (79 g, crude). The crude product could be directly used in the next step, MS (ESI): 247.1 [M+H]+.

Step 5: Synthesis of Compound B6-1

B5-1 (4.9, 19.9 mmol) and palladium on carbon (2 g, 19.9 mmol, 10% purity) were suspended in methanol (100 mL), and the suspension was left for the reaction at 25° C. under hydrogen (50 psi) for 16 h. The palladium on carbon was removed by filtration, and the filtrate was concentrated under reduced pressure and purified by column chromatography ($SiO_2$, PE/EA=1/0 to 1/2) to give a yellow solid B6-1 (1.44 g, 33.5% yield).

$^1$H NMR: (400 MHz, $CDCl_3$)) δ: 7.24 (d, J=2.3 Hz, 1H), 6.56 (d, J=2.0 Hz, 1H), 3.67 (br s, 2H), 3.32-3.25 (m, 2H), 3.19-3.13 (m, 3H), 3.09-2.97 (m, 1H), 2.81-2.65 (m, 2H), 2.07-1.90 (m, 2H), 1.78-1.62 (m, 1H), 1.37-1.23 (m, 1H), MS (ESI): 217.2 [M+H]$^+$.

Step 6: Synthesis of Compound B7-1

B6-1 (7 g, 32.4 mmol) was dissolved in anhydrous tetrahydrofuran (300 mL), and $LiAlH_4$ (6.14 g, 162 mmol) was added at 0° C. The mixture was warmed to 25° C. under nitrogen atmosphere and left for the reaction for 2 h. Water was slowly added to the reaction solution to quench the reaction; during the addition, the temperature of the reaction solution was kept at 0-10° C. The reaction solution was diluted with 800 mL of ethyl acetate and washed with water (100 mL×3). The organic phase was dried over anhydrous sodium sulfate. The organic phase was filtered and distilled under reduced pressure to give a crude product. The crude product was purified by column chromatography ($SiO_2$, DCM/(MeOH+1% $NH_4OH$)=10/0 to 10/1) to give a yellow oil (6.25 g, 95.5% yield).

$^1$H NMR: (400 MHz, $CDCl_3$) δ: 6.31 (s, 1H), 6.21 (s, 1H), 3.88 (d, J=15.1 Hz, 1H), 3.62-3.34 (br s, 2H), 3.26 (d, J=15.1 Hz, 1H), 2.98-2.69 (m, 4H), 2.42 (s, 3H), 2.03 (t, J=10.7 Hz, 1H), 1.92 (tdd, J=3.4, 6.5, 13.1 Hz, 1H), 1.88-1.75 (m, 2H), 1.34-1.17 (m, 1H), MS (ESI): 203.2 [M+H]$^+$.

Step 7: Preparation of Compounds B7-2 and B7-3

B7-2

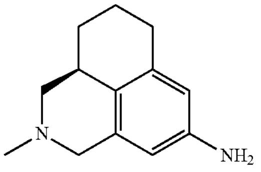

B7-3

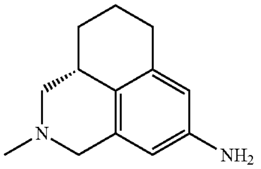

B7-1 (1.5 g, 7.41 mmol) was chirally resolved by preparative supercritical fluid chromatography (prep SFC) (SFC chiral resolution conditions: instrument: Waters SFC350; column: DAICEL CHIRALPAK AD (250 mm×50 mm, 10 μm); mobile phases: A: $CO_2$, B: IPA (0.1% $NH_3H_2O$); gradient: B %: 50%-50%; flow rate: 200 mL/min; column temperature: 40° C.). The stepwise eluates were concentrated under reduced pressure and lyophilized to give a yellow oil B7-2 (peak 1, 438 mg, 29.20% yield) and a yellow oil B7-3 (peak 2, 450 mg, 30.00% yield).

B7-2: $^1$H NMR: (400 MHz, $CDCl_3$) δ: 6.32 (s, 1H), 6.22 (s, 1H), 3.88 (d, J=15.1 Hz, 1H), 3.48 (br s, 2H), 3.26 (br d, J=15.1 Hz, 1H), 2.93 (dd, J=4.6, 10.5 Hz, 1H), 2.90-2.80 (m, 1H), 2.79-2.64 (m, 2H), 2.42 (s, 3H), 2.02 (t, J=10.7 Hz, 1H), 1.92 (dtd, J=3.6, 6.5, 9.8 Hz, 1H), 1.87-1.79 (m, 2H), 1.36-1.15 (m, 1H)

MS (ESI): 203.2 $[M+H]^+$.

B7-3: $^1$H NMR: (400 MHz, $CDCl_3$) δ: 6.32 (s, 1H), 6.22 (s, 1H), 3.87 (d, J=15.3 Hz, 1H), 3.47 (br s, 2H), 3.26 (d, J=15.1 Hz, 1H), 2.93 (dd, J=4.8, 10.6 Hz, 1H), 2.89-2.80 (m, 1H), 2.80-2.65 (m, 2H), 2.42 (s, 3H), 2.02 (t, J=10.7 Hz, 1H), 1.97-1.88 (m, 1H), 1.87-1.75 (m, 2H), 1.35-1.17 (m, 1H), MS (ESI): 203.2 $[M+H]^+$.

Intermediates B7-4 to B7-39 could be obtained by using different starting materials according to the synthesis for the intermediate B7-1.

TABLE 2

Structural formulas of intermediates B7-4 to B7-39

| Intermediate | Structure | MS $(M + H)^+$ | Intermediate | Structure | MS $(M + H)^+$ |
|---|---|---|---|---|---|
| B7-4 | 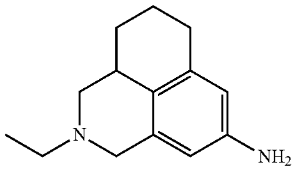 [SMILES: CCN1Cc2cc(N)cc3c2C(CCC3)C1] | 217.2 | B7-5 | 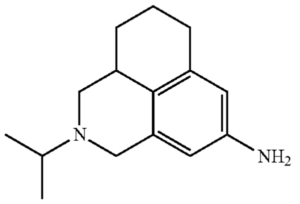 [SMILES: CC(C)N1Cc2cc(N)cc3c2C(CCC3)C1] | 231.1 |
| B7-6 | 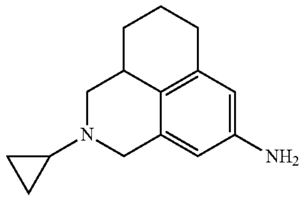 [SMILES: Nc1cc2c3c(c1)CN(C1CC1)CC3CCC2] | 229.2 | B7-7 | 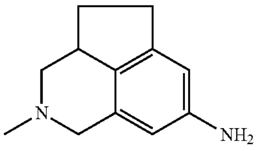 | 189.2 |
| B7-8 | 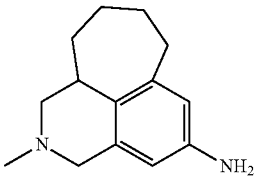 [SMILES: CN1Cc2cc(N)cc3c2C(CCCC3)C1] | 217.2 | B7-9 | 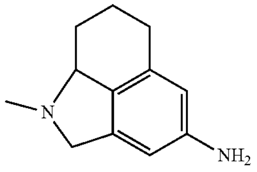 | 189.2 |
| B7-10 | 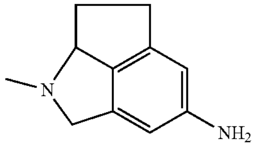 | 175.1 | B7-11 | 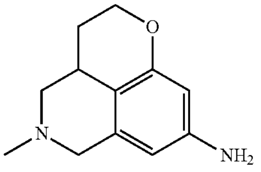 | 205.1 |

TABLE 2-continued
Structural formulas of intermediates B7-4 to B7-39
| Intermediate | Structure | MS (M + H)$^+$ | Intermediate | Structure | MS (M + H)$^+$ |
|---|---|---|---|---|---|
| B7-12 | 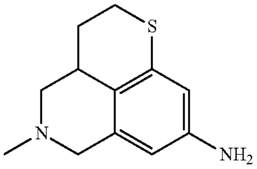 | 221.1 | B7-13 | 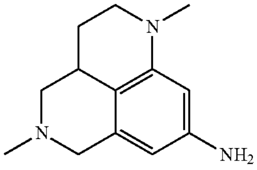 | 218.2 |
| B7-14 | 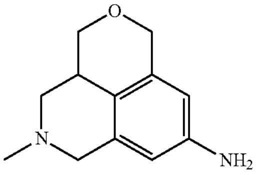 | 205.1 | B7-15 | 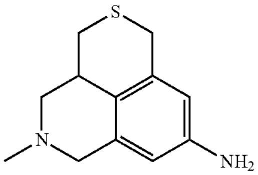 | 221.1 |
| B7-16 | 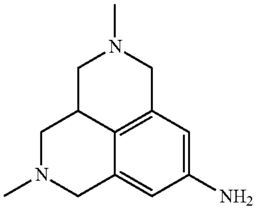 [SMILES: CN1Cc2cc(N)cc3c2C(C1)CN(C)C3] | 218.2 | B7-17 | 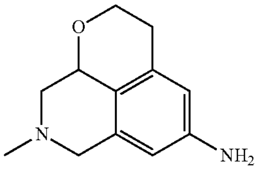 | 205.1 |
| B7-18 | 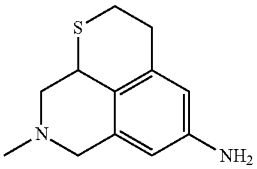 | 221.1 | B7-19 | 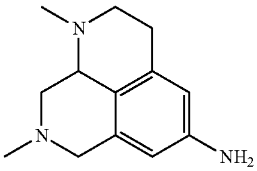 [SMILES: CN1Cc2cc(N)cc3c2C(C1)N(C)CC3] | 218.2 |
| B7-20 | 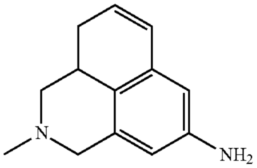 | 201.1 | B7-21 | 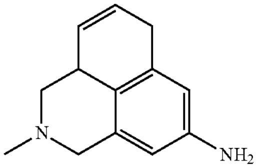 | 201.1 |
| B7-22 | 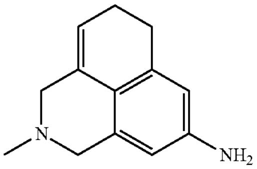 | 201.1 | B7-23 | 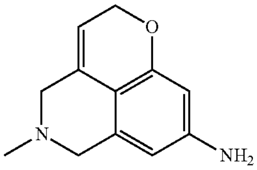 | 203.1 |
| B7-24 | 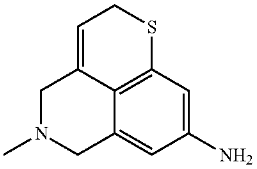 | 219.1 | B7-25 | 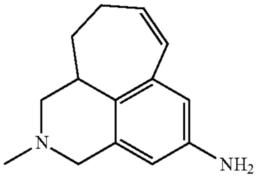 | 215.2 |
| B7-26 | 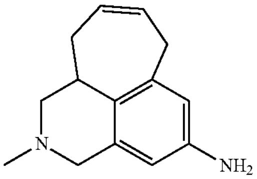 | 215.2 | B7-27 | 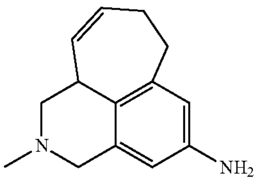 [SMILES: CN1Cc2cc(N)cc3c2C(C=CCC3)C1] | 215.2 |

TABLE 2-continued
Structural formulas of intermediates B7-4 to B7-39
| Intermediate | Structure | MS $(M + H)^+$ | Intermediate | Structure | MS $(M + H)^+$ |
|---|---|---|---|---|---|
| B7-28 | 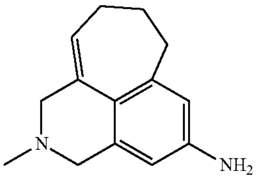 [SMILES: CN1CC2=CCCCc3cc(N)cc(c32)C1] | 215.2 | B7-29 | 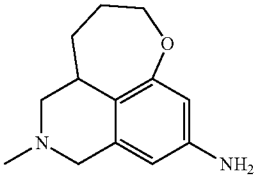 | 219.2 |
| B7-30 | 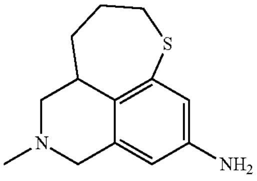 | 235.1 | B7-31 | 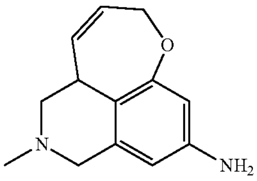 | 217.1 |
| B7-32 | 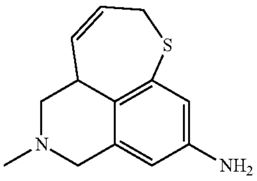 | 233.1 | B7-33 | 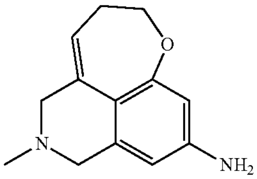 [SMILES: CN1CC2=CCCSc3cc(N)cc(c32)C1] | 217.1 |
| B7-34 | 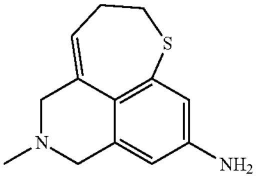 | 233.1 | B7-35 | 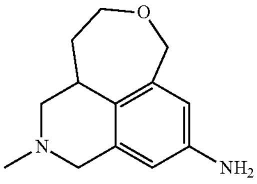 | 219.2 |
| B7-36 | 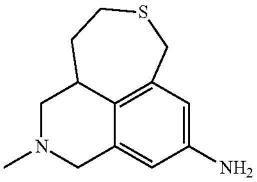 [SMILES: CN1Cc2cc(N)cc3c2C(CCSC3)C1] | 235.1 | B7-37 | 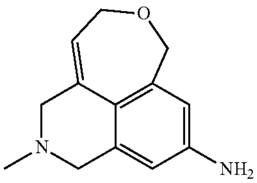 [SMILES: CN1CC2=CCOCc3cc(N)cc(c32)C1] | 217.1 |
| B7-38 | 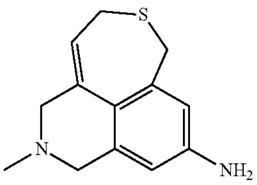 [SMILES: CN1CC2=CCSCc3cc(N)cc(c32)C1] | 233.1 | B7-39 | 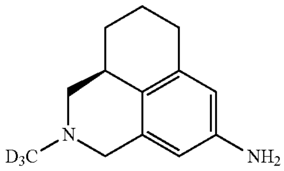 [SMILES: [2H]C([2H])([2H])N1Cc2cc(N)cc3c2[C@H](CCC3)C1] | 206.2 |

Example 1. Synthesis of (6-(5-fluoro-2-((2-methyl-2,3,7,8,9,9a-hexahydro-1H-benzo[de]isoquinolin-5-yl)amino)-7H-pyrrolo[2,3-d]pyrimidin-7-yl)pyridin-2-yl)imido)dimethyl-λ$^6$-sulfanone (Compound 1)

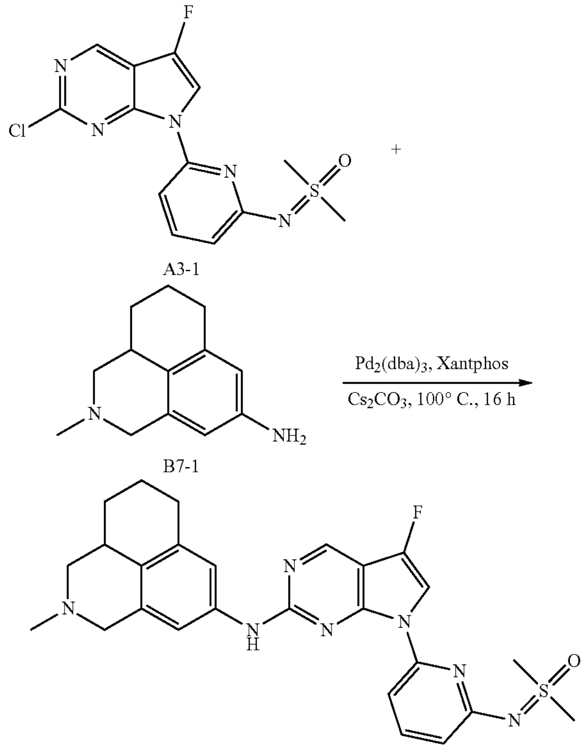

A3-1

B7-1

1

2-Methyl-2,3,7,8,9,9a-hexahydro-1H-benzo[de]isoquinoline-5-amine (119 mg, 0.59 mmol), ((6-(2-chloro-5-fluoro-7H-pyrrolo[2,3-d]pyrimidin-7-yl)pyridin-2-yl)imino)dimethyl-λ$^6$-sulfanone (200 mg, 0.59 mmol), and cesium carbonate (289 mg, 0.89 mmol) were weighed into a 100 mL single-neck flask, and 1,4-dioxane (15 mL) was added. After the reaction solution was purged three times with argon, $Pd_2(dba)_3$ (27 mg, 0.03 mmol) and Xantphos (41 mg, 0.07 mmol) were added thereto, and the mixture was heated to 100° C. and stirred for 5 h under argon atmosphere. LC-MS monitoring showed that the reaction was complete. The reaction solution was concentrated to dryness by rotary evaporation and purified through a reversed-phase column to give a pale yellow solid, ((6-(5-fluoro-2-((2-methyl-2,3,7,8,9,9a-hexahydro-1H-benzo[de]isoquinolin-5-yl)amino)-7H-pyrrolo[2,3-d]pyrimidin-7-yl)pyridin-2-yl)imido)dimethyl-λ$^6$-sulfanone (50 mg, 17%).

$^1$H NMR (400 MHz, $CDCl_3$) δ: 8.63 (s, 1H), 8.17 (s, 1H), 7.63 (d, J=27.8 Hz, 2H), 7.13 (s, 2H), 6.60 (s, 1H), 3.96-3.92 (m, 1H), 3.34 (s, 7H), 2.88-2.84 (m, 4H), 2.41 (s, 3H), 2.03-1.82 (m, 3H), 1.23-1.21 (m, 2H), LC-MS: 506.3 $[M+H]^+$.

Examples 2-70. Synthesis of Compounds 2-70

By the procedures similar to those in the synthesis of compound 1, the target compounds 2-70 in Table 3 could be obtained using intermediates A3-1 to A3-27 and B7-1 to B7-39 as starting materials.

TABLE 3
| Structures of compounds 2-70 | | | | | |
|---|---|---|---|---|---|
| Compound | Compound structure | MS (M + H)+ | Compound | Compound structure | MS (M + H)+ |
| 2 | 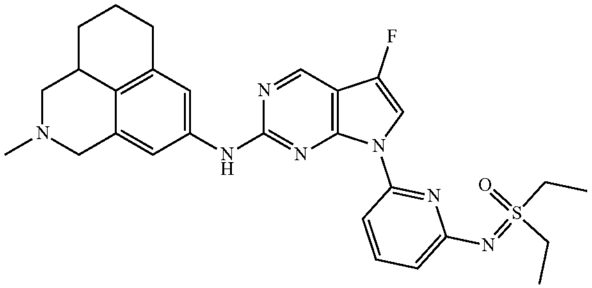 [SMILES: CCS(=O)(CC)=Nc1cccc(-n2cc(F)c3cnc(Nc4cc5c6c(c4)CN(C)CC6CCC5)nc32)n1] | 534.2 | 3 | 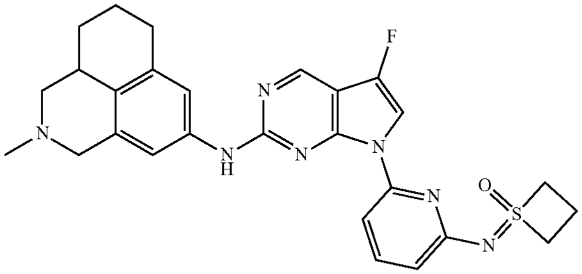 [SMILES: CN1Cc2cc(Nc3ncc4c(F)cn(-c5cccc(N=S6(=O)CCC6)n5)c4n3)cc3c2C(CCC3)C1] | 518.2 |
| 4 | 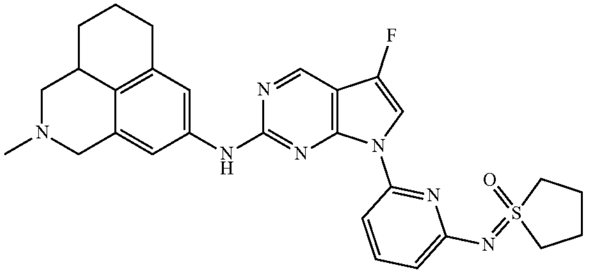 [SMILES: CN1Cc2cc(Nc3ncc4c(F)cn(-c5cccc(N=S6(=O)CCCC6)n5)c4n3)cc3c2C(CCC3)C1] | 532.2 | 5 | 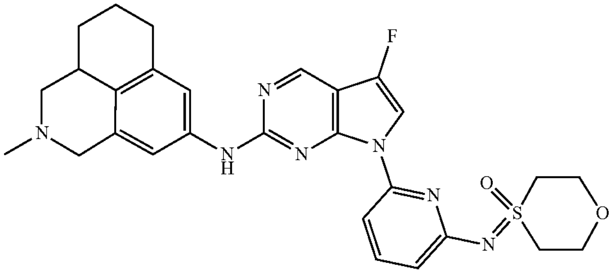 [SMILES: CN1Cc2cc(Nc3ncc4c(F)cn(-c5cccc(N=S6(=O)CCOCC6)n5)c4n3)cc3c2C(CCC3)C1] | 548.2 |
| 6 | 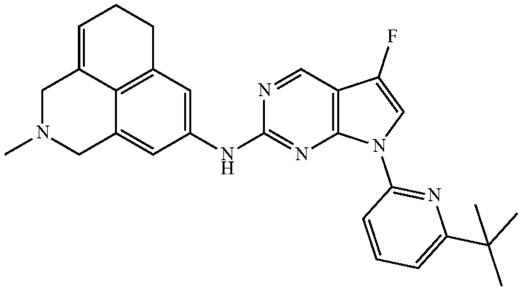 [SMILES: CN1CC2=CCCc3cc(Nc4ncc5c(F)cn(-c6cccc(C(C)(C)C)n6)c5n4)cc(c32)C1] | 471.3 | 7 | 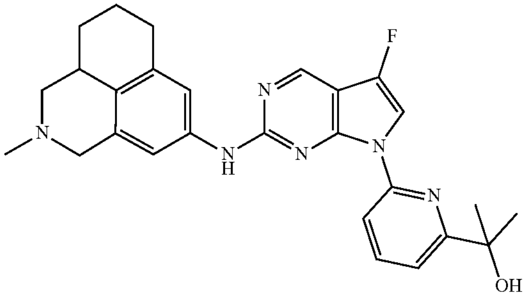 [SMILES: CN1Cc2cc(Nc3ncc4c(F)cn(-c5cccc(C(C)(C)O)n5)c4n3)cc3c2C(CCC3)C1] | 473.2 |

TABLE 3-continued
| Structures of compounds 2-70 | | | | | |
|---|---|---|---|---|---|
| Compound | Compound structure | MS (M + H)$^+$ | Compound | Compound structure | MS (M + H)$^+$ |
| 8 | 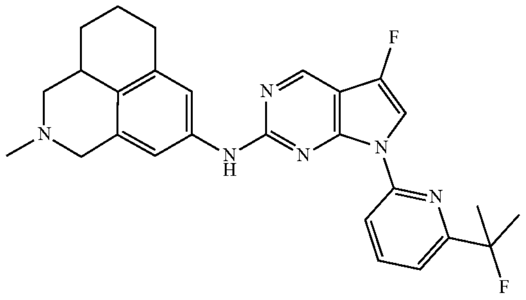 [SMILES: CN1Cc2cc(Nc3ncc4c(F)cn(-c5cccc(C(C)(C)F)n5)c4n3)cc3c2C(CCC3)C1] | 475.2 | 9 | 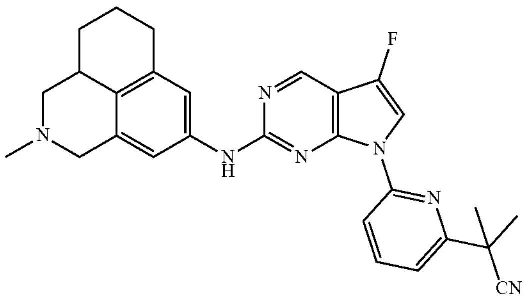 [SMILES: CN1Cc2cc(Nc3ncc4c(F)cn(-c5cccc(C(C)(C)C#N)n5)c4n3)cc3c2C(CCC3)C1] | 482.2 |
| 10 | 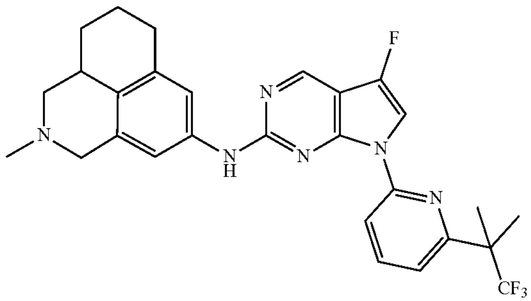 [SMILES: CN1Cc2cc(Nc3ncc4c(F)cn(-c5cccc(C(C)(C)C(F)(F)F)n5)c4n3)cc3c2C(CCC3)C1] | 525.2 | 11 | 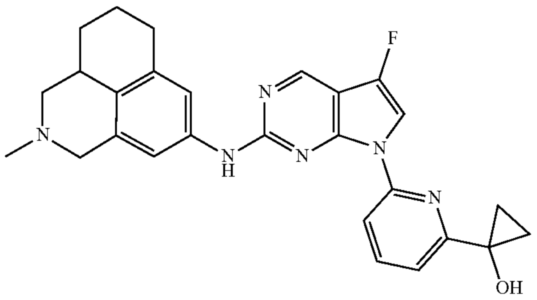 [SMILES: CN1Cc2cc(Nc3ncc4c(F)cn(-c5cccc(C6(O)CC6)n5)c4n3)cc3c2C(CCC3)C1] | 471.2 |
| 12 | 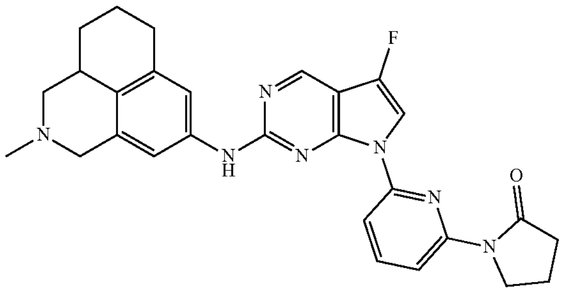 [SMILES: CN1Cc2cc(Nc3ncc4c(F)cn(-c5cccc(N6CCCC6=O)n5)c4n3)cc3c2C(CCC3)C1] | 498.2 | 13 | 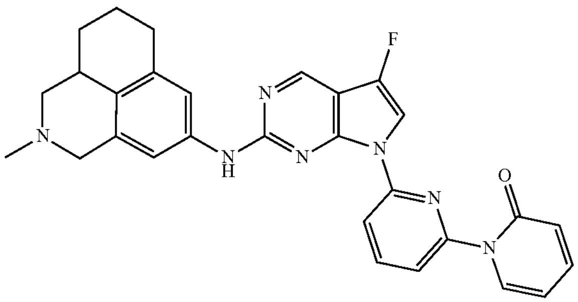 [SMILES: CN1Cc2cc(Nc3ncc4c(F)cn(-c5cccc(-n6ccccc6=O)n5)c4n3)cc3c2C(CCC3)C1] | 508.2 |

TABLE 3-continued
Structures of compounds 2-70
| Compound | Compound structure | MS (M + H)$^+$ | Compound | Compound structure | MS (M + H)$^+$ |
| --- | --- | --- | --- | --- | --- |
| 14 | 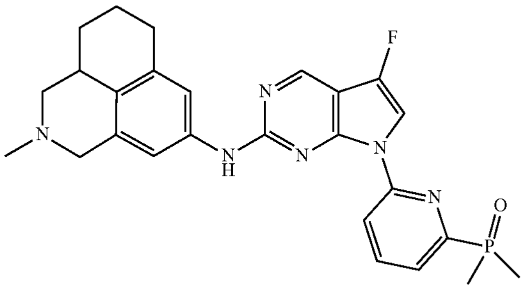 | 491.2 | 15 | 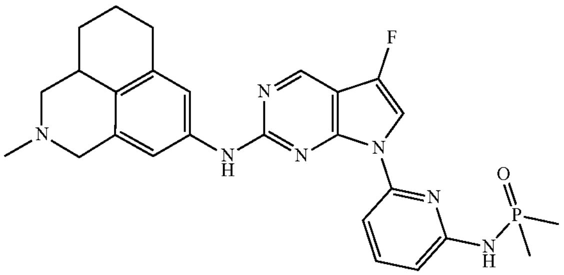 | 506.2 |
| 16 | 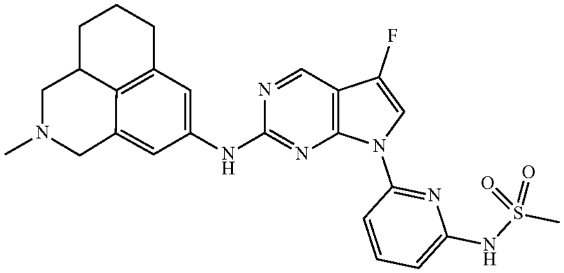 | 507.2 | 17 | 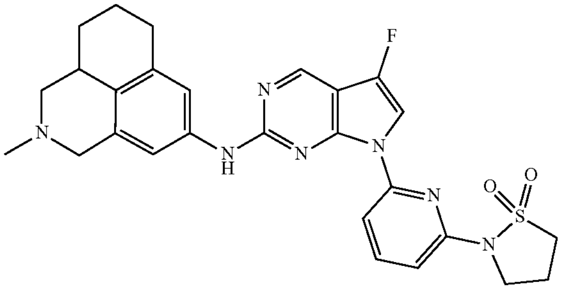 [SMILES: CN1Cc2cc(Nc3ncc4c(F)cn(-c5cccc(N6CCCS6(=O)=O)n5)c4n3)cc3c2C(CCC3)C1] | 534.2 |
| 18 | 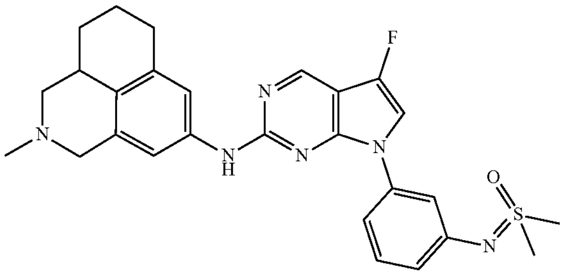 | 505.2 | 19 | 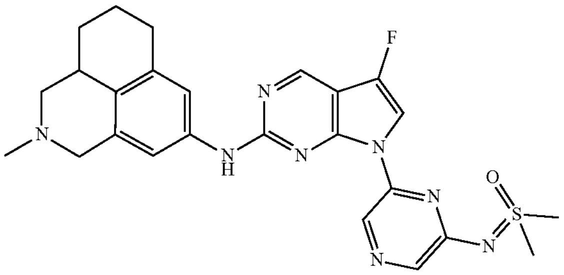 | 507.2 |

TABLE 3-continued
Structures of compounds 2-70
| Compound | Compound structure | MS (M + H)$^+$ | Compound | Compound structure | MS (M + H)$^+$ |
| --- | --- | --- | --- | --- | --- |
| 20 | 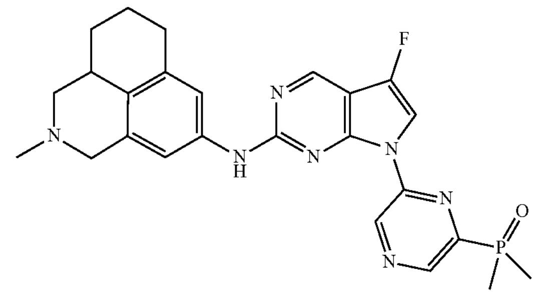 | 492.2 | 21 | 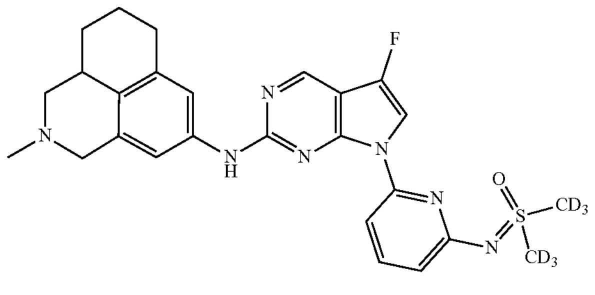 [SMILES: [2H]C([2H])([2H])S(=O)(=Nc1cccc(-n2cc(F)c3cnc(Nc4cc5c6c(c4)CN(C)CC6CCC5)nc32)n1)C([2H])([2H])[2H]] | 512.2 |
| 22 | 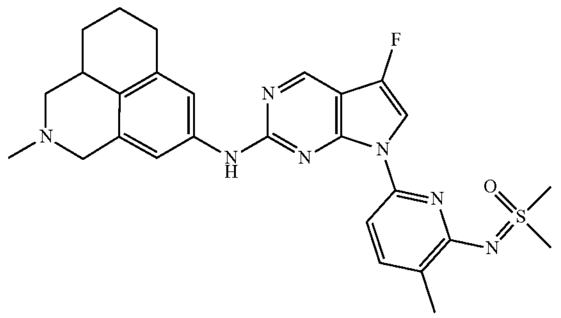 | 520.2 | 23 | 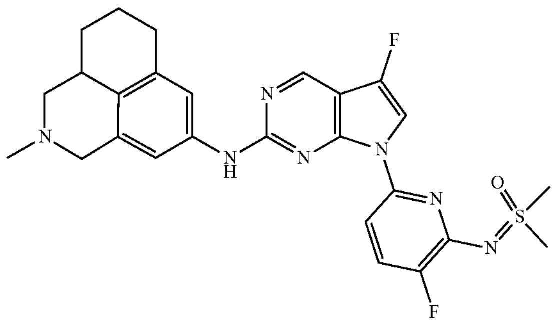 | 524.2 |
| 24 | 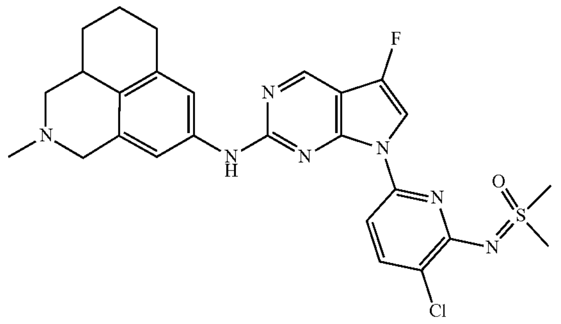 | 540.2 | 25 | 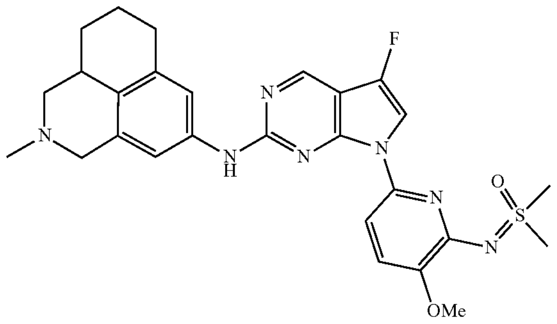 | 536.2 |

TABLE 3-continued
Structures of compounds 2-70
| Compound | Compound structure | MS (M + H)+ | Compound | Compound structure | MS (M + H)+ |
|---|---|---|---|---|---|
| 26 | 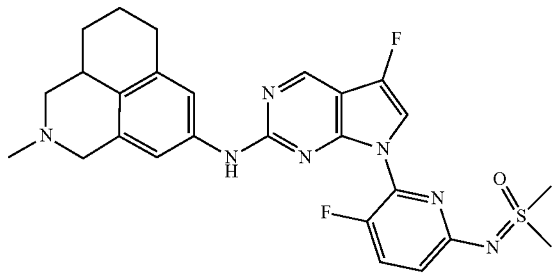 | 524.2 | 27 | 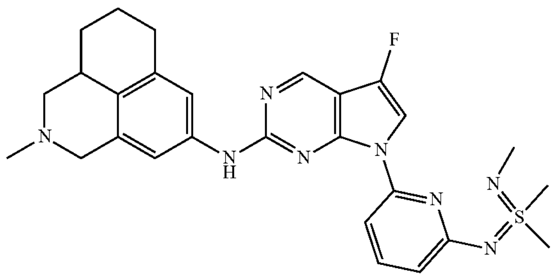 | 519.2 |
| 28 | 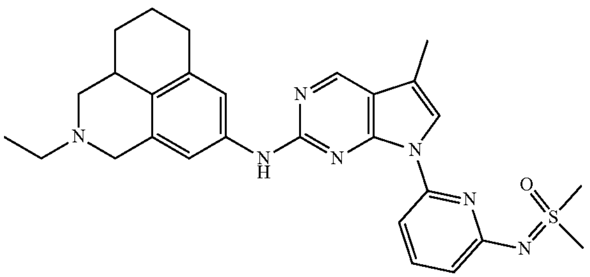 [SMILES: CCN1Cc2cc(Nc3ncc4c(C)cn(-c5cccc(N=S(C)(C)=O)n5)c4n3)cc3c2C(CCC3)C1] | 516.3 | 29 | 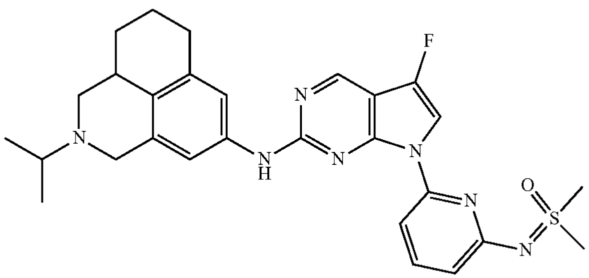 [SMILES: CC(C)N1Cc2cc(Nc3ncc4c(F)cn(-c5cccc(N=S(C)(C)=O)n5)c4n3)cc3c2C(CCC3)C1] | 534.2 |
| 30 | 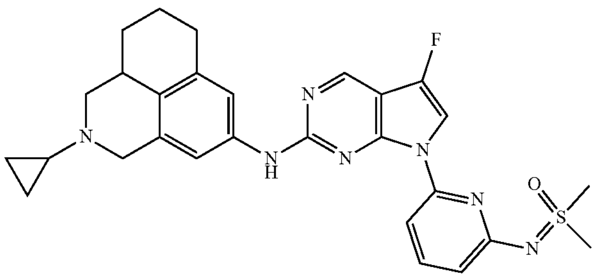 [SMILES: CS(C)(=O)=Nc1cccc(-n2cc(F)c3cnc(Nc4cc5c6c(c4)CN(C4CC4)CC6CCC5)nc32)n1] | 532.2 | 31 | 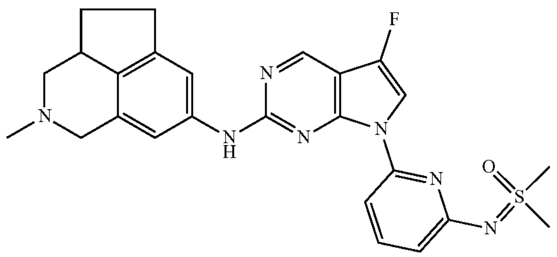 | 492.2 |

TABLE 3-continued
| Structures of compounds 2-70 | | | | | |
|---|---|---|---|---|---|
| Compound | Compound structure | MS (M + H)$^+$ | Compound | Compound structure | MS (M + H)$^+$ |
| 32 | 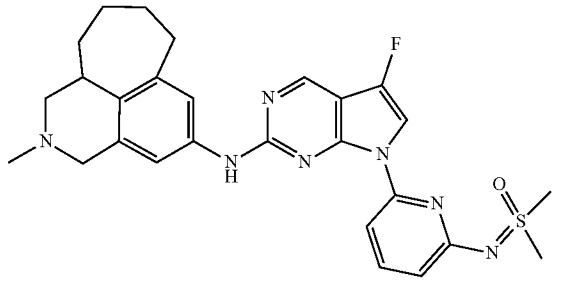 | 520.2 | 33 | 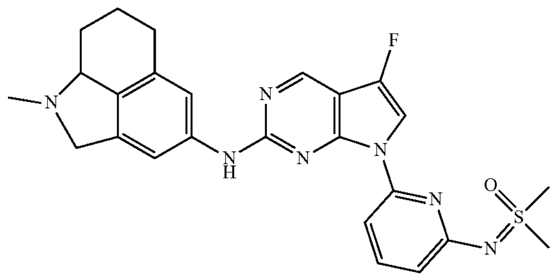 | 492.2 |
| 34 | 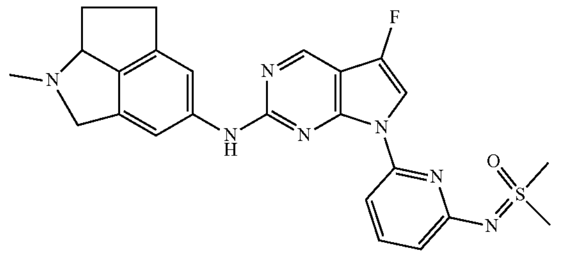 | 478.2 | 35 | 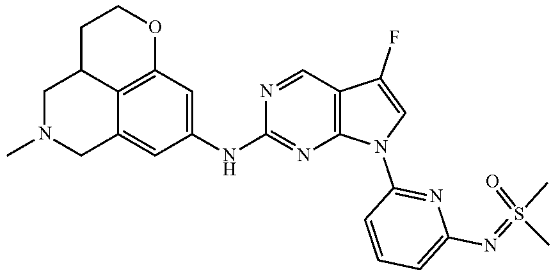 | 508.2 |
| 36 | 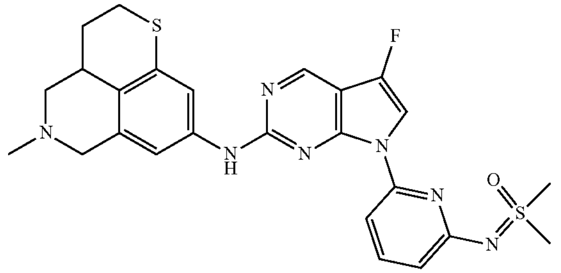 | 524.2 | 37 | 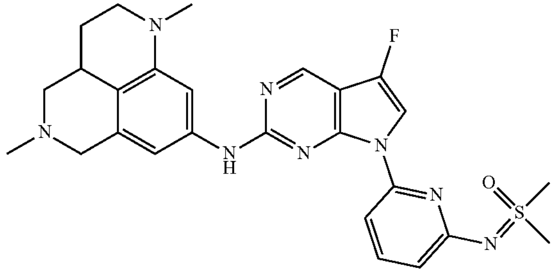 | 521.2 |

TABLE 3-continued
| Structures of compounds 2-70 | | | | | |
|---|---|---|---|---|---|
| Compound | Compound structure | MS (M + H)+ | Compound | Compound structure | MS (M + H)+ |
| 38 | 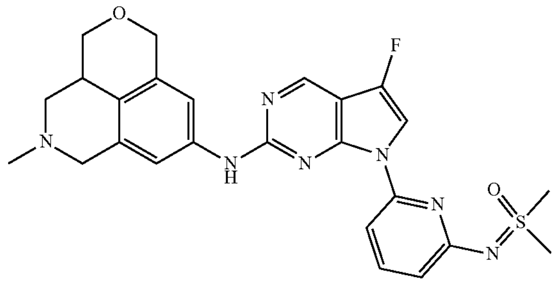 | 508.2 | 39 | 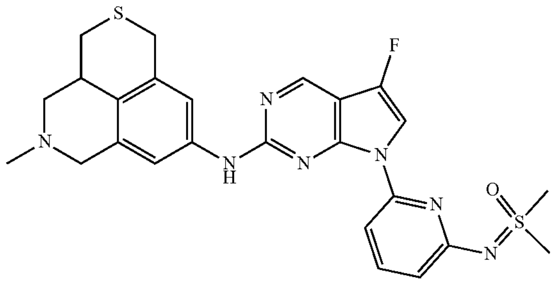 | 524.2 |
| 40 | 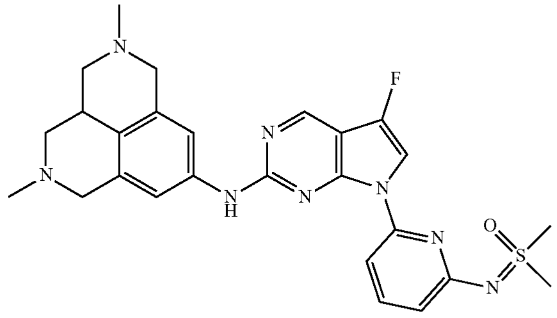 | 521.2 | 41 | 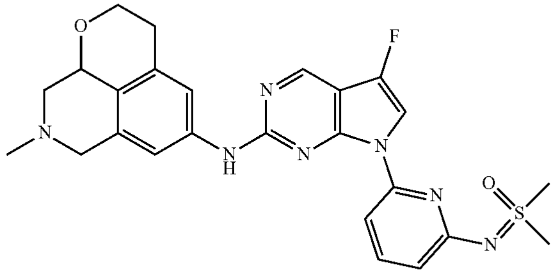 | 508.2 |
| 42 | 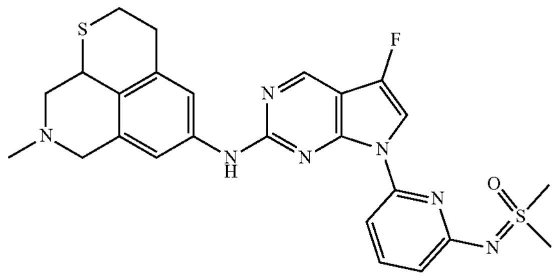 | 524.2 | 43 | 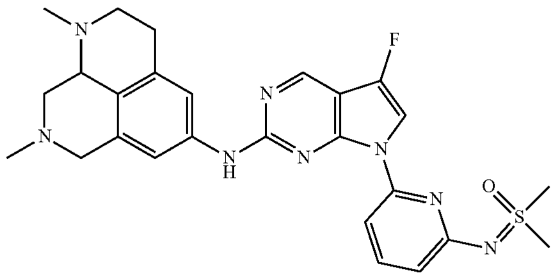 | 521.2 |

TABLE 3-continued
Structures of compounds 2-70
| Compound | Compound structure | MS (M + H)+ | Compound | Compound structure | MS (M + H)+ |
|---|---|---|---|---|---|
| 44 | 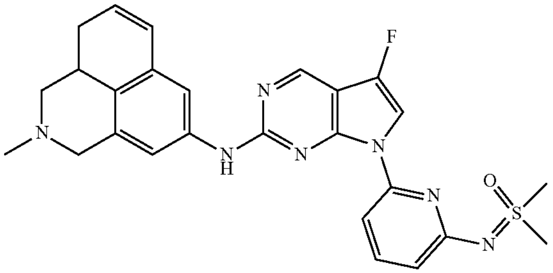 | 504.2 | 45 | 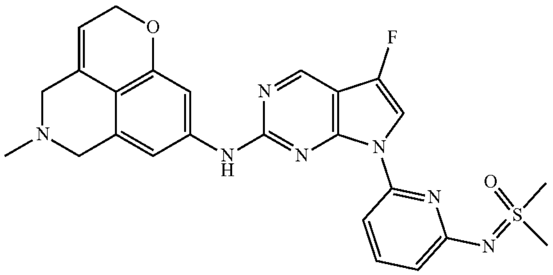 | 504.2 |
| 46 | 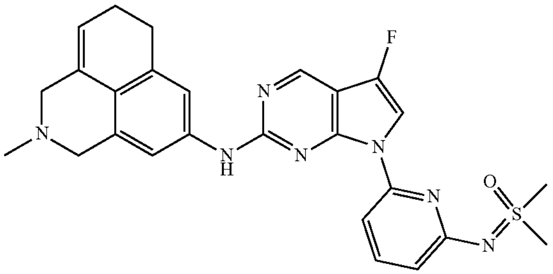 | 504.2 | 47 | 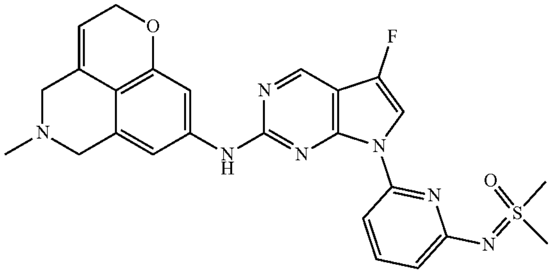 | 506.2 |
| 48 | 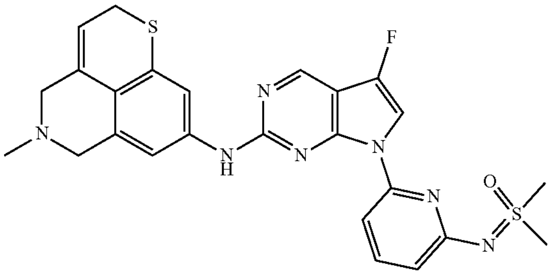 | 522.2 | 49 | 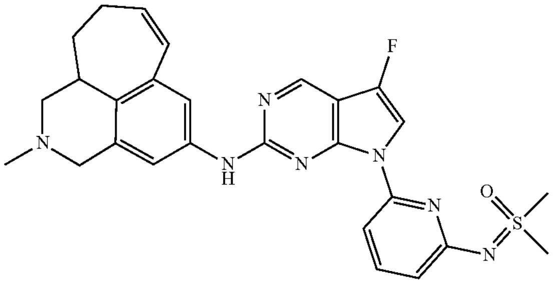 | 518.2 |

TABLE 3-continued
Structures of compounds 2-70
| Compound | Compound structure | MS (M + H)+ | Compound | Compound structure | MS (M + H)+ |
|---|---|---|---|---|---|
| 50 | 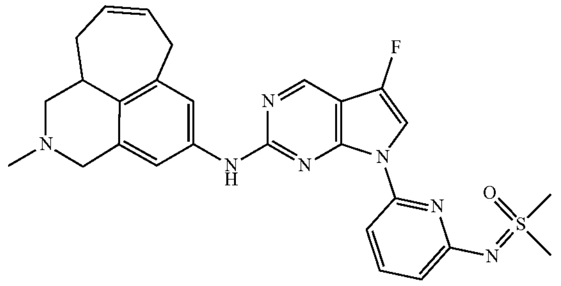 | 518.2 | 51 | 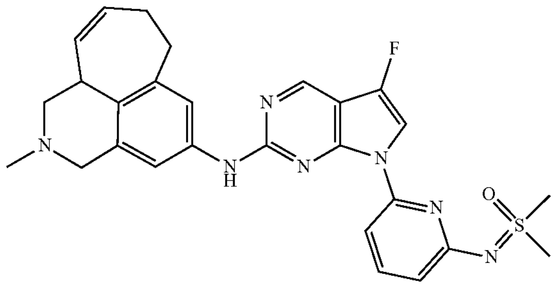 | 518.2 |
| 52 | 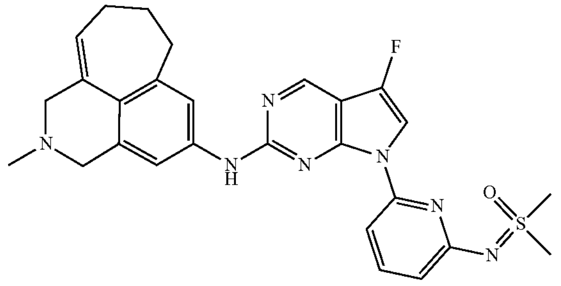 | 518.2 | 53 | 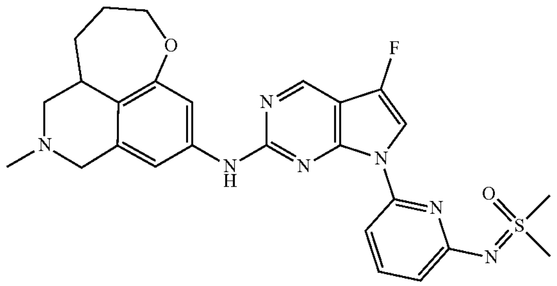 | 522.2 |
| 54 | 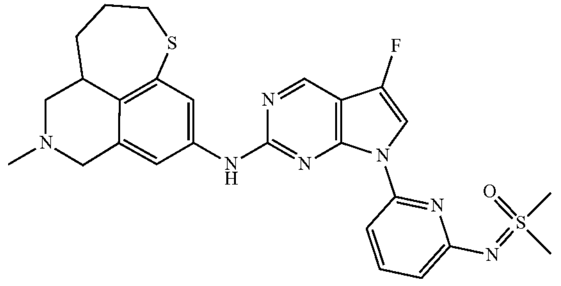 | 538.2 | 55 | 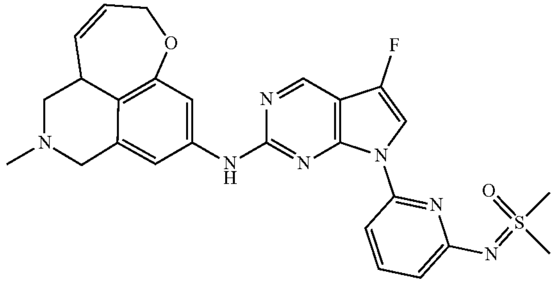 | 520.2 |

TABLE 3-continued
| Structures of compounds 2-70 | | | | | |
|---|---|---|---|---|---|
| Compound | Compound structure | MS (M + H)$^+$ | Compound | Compound structure | MS (M + H)$^+$ |
| 56 | 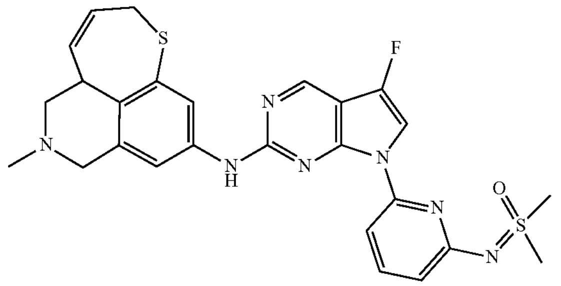 | 536.2 | 57 | 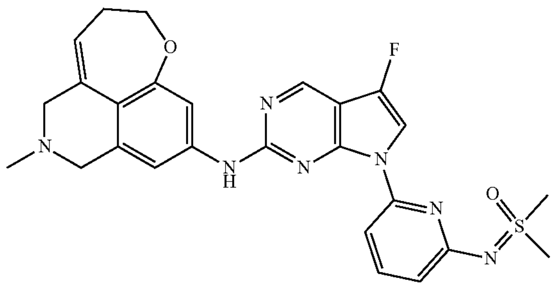 | 520.2 |
| 58 | 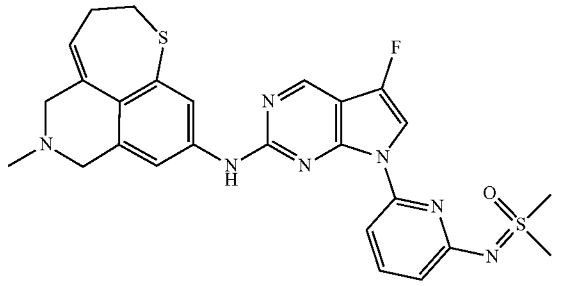 | 538.2 | 59 | 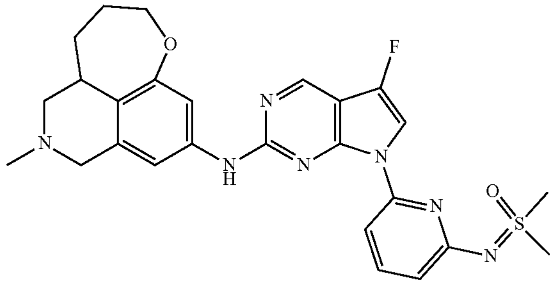 | 522.2 |
| 60 | 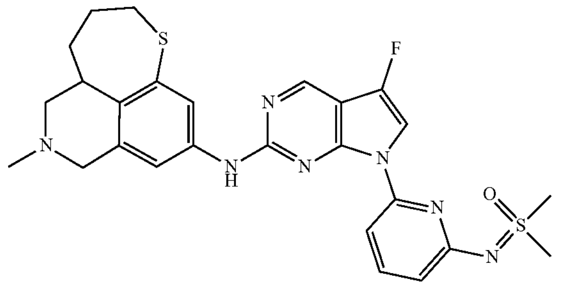 | 538.2 | 61 | 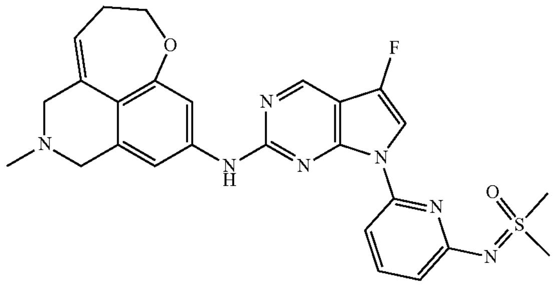 | 520.2 |

TABLE 3-continued
| Compound | Compound structure | MS (M + H)+ | Compound | Compound structure | MS (M + H)+ |
|---|---|---|---|---|---|
| Structures of compounds 2-70 | | | | | |
| 62 | 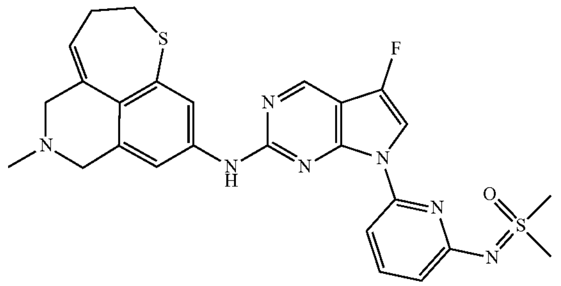 | 536.2 | 63 | 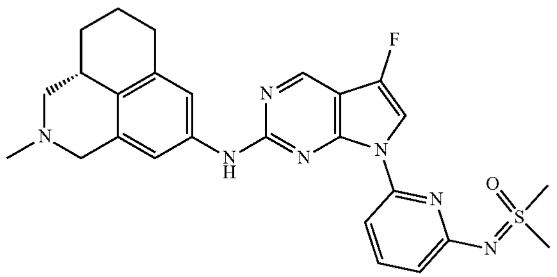 | 506.2 |
| 64 | 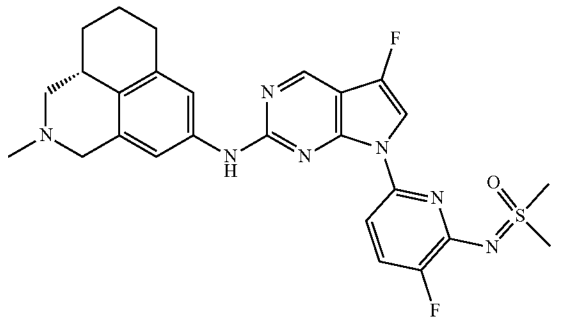 | 524.2 | 65 | 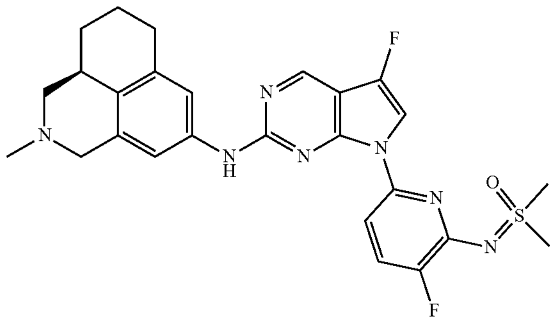 | 524.2 |
| 66 | 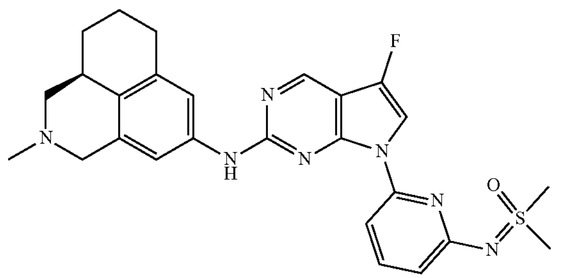 | 506.2 | 67 | 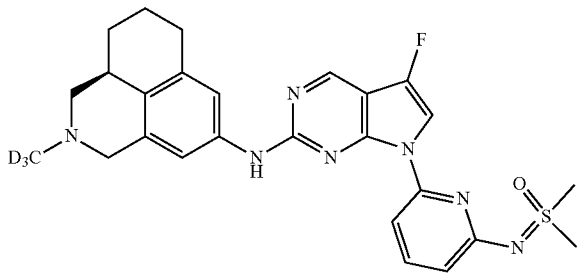 [SMILES: [2H]C([2H])([2H])N1Cc2cc(Nc3ncc4c(F)cn(-c5cccc(N=S(C)(C)=O)n5)c4n3)cc3c2[C@H](CCC3)C1] | 509.2 |

TABLE 3-continued
| Structures of compounds 2-70 | | | | | |
|---|---|---|---|---|---|
| Compound | Compound structure | MS $(M + H)^+$ | Compound | Compound structure | MS $(M + H)^+$ |
| 68 | 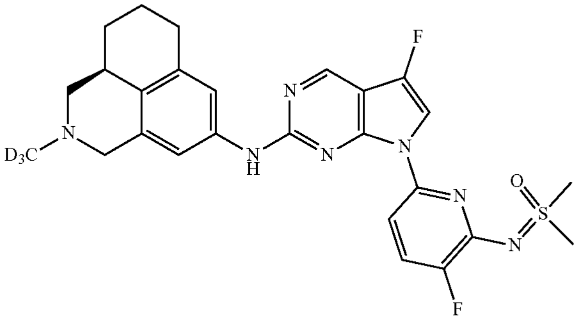 [SMILES: [2H]C([2H])([2H])N1Cc2cc(Nc3ncc4c(F)cn(-c5ccc(F)c(N=S(C)(C)=O)n5)c4n3)cc3c2[C@H](CCC3)C1] | 527.2 | 69 | 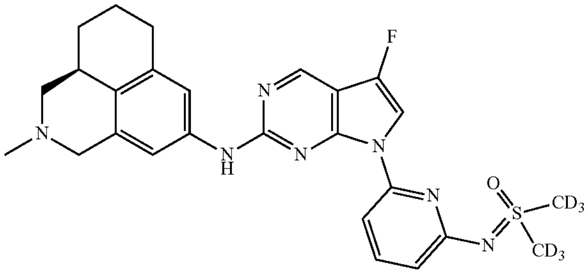 [SMILES: [2H]C([2H])([2H])S(=O)(=Nc1cccc(-n2cc(F)c3cnc(Nc4cc5c6c(c4)CN(C)C[C@H]6CCC5)nc32)n1)C([2H])([2H])[2H]] | 512.2 |
| 70 | 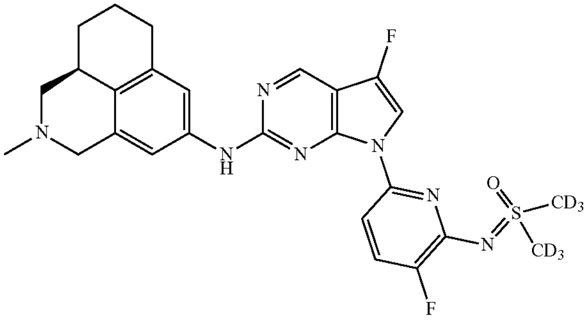 [SMILES: [2H]C([2H])([2H])S(=O)(=Nc1nc(-n2cc(F)c3cnc(Nc4cc5c6c(c4)CN(C)C[C@H]6CCC5)nc32)ccc1F)C([2H])([2H])[2H]] | 530.2 | | | |

Example 71. Assay of Inhibitory Activity of Compounds of the Present Invention Against Wee-1 Kinase After the serially diluted compound and an enzyme were mixed, the mixture was incubated at room temperature (25° C.) for 15 min, and then centrifuged at 1000 rpm for 1 min for mixing. 5 L of substrate was added to start the reaction. After the mixture was reacted at room temperature for 60 min, 5 μL of ADP-GLO reagent was added and the mixture was centrifuged at 1000 rpm for 1 min for mixing. The mixture was subsequently incubated at room temperature for 60 min, and then 10 μL of kinase detection reagent was added. The mixture was incubated for 60 min, and the chemiluminescence was determined. The inhibition percentage of the enzyme activity by the compounds was calculated compared with the DMSO group, and the $IC_{50}$ values were also calculated.

TABLE 4

$IC_{50}$ for the inhibitory activity of the compounds of the present invention against Wee-1 kinase (nM)

| Compound | $IC_{50}$ (nM) | Compound | $IC_{50}$ (nM) | Compound | $IC_{50}$ (nM) |
|---|---|---|---|---|---|
| 1 | 1.52 | 2 | 1.96 | 3 | 2.48 |
| 4 | 2.47 | 5 | 2.79 | 14 | 2.71 |
| 19 | 2.08 | 21 | 1.67 | 23 | 2.05 |
| 24 | 2.49 | 28 | 2.33 | 63 | 3.47 |
| 64 | 3.36 | 65 | 1.56 | 66 | 1.19 |
| 67 | 1.86 | 68 | 1.97 | 69 | 1.54 |
| 70 | 1.84 | MK-1775 | 4.38 | | |

As can be seen from the data in Table 4, the compounds of the present invention have a strong inhibitory effect on Wee-1 kinase. For example, the $IC_{50}$ values of compounds 1, 2, 21, 65, 66, 67, 68, 69 and 70 on Wee-1 kinase are all less than 2.0 nM, which are about 2 times higher than that of the control drug MK-1775.

Example 72. In-Vitro Anti-Proliferative Activity of the Compounds of the Present Invention on MIA PaCa-2 Cells MIA PaCa-2 cells were seeded on a 384-well plate at 3000 cells/well. After overnight adherence culture, DMSO or the compounds serially diluted 1:5 from 5 M were added. The viability was assessed 72 h after dosing by measuring the intracellular ATP content. The inhibition percentage of viable cells by the compounds was calculated by comparing with the DMSO group, and the $IC_{50}$ value was calculated. The results are shown in Table 5 below.

Example 73. In-Vitro Anti-Proliferative Activity of the Compounds of the Present Invention in Combination with Gemcitabine (GMC) on MIA PaCa-2 Cells MIA PaCa-2 cells were seeded on a 384-well plate at 3000 cells/well, and 20 nM gemcitabine was added. After overnight adherence culture, DMSO or the compounds serially diluted 1:5 from 100 nM were added. The viability was assessed 72 h after dosing by measuring the intracellular ATP content. The inhibition percentage of viable cells by the compounds was calculated by comparing with the DMSO group, and the $IC_{50}$ value was calculated. The results are shown in Table 5 below.

TABLE 5

Anti-proliferative activity of the compound of the present invention used alone or in combination with GMC on MIA PaCa-2 cells

| | $IC_{50}$ (nM) | | | $IC_{50}$ (nM) | |
|---|---|---|---|---|---|
| Compound | Without GMC | GMC (20 nM) | Compound | Without GMC | GMC (20 nM) |
| 1 | 37 | 1.7 | 2 | 106 | 2.4 |
| 3 | 128 | 2.3 | 4 | 115 | 2.1 |
| 5 | 139 | 2.4 | 14 | 331 | 1.3 |
| 19 | 73 | 1.6 | 21 | 85 | 1.7 |
| 23 | 155 | 1.2 | 24 | 184 | 1.6 |
| 28 | 172 | 1.3 | 63 | 173 | 2.3 |
| 64 | 179 | 2.5 | 65 | 78 | 1.4 |
| 66 | 28 | 0.9 | 67 | 49 | 0.8 |
| 68 | 76 | 0.9 | 70 | 89 | 1.1 |
| MK-1775 | 904 | 24.2 | | | |

As can be seen from the data in Table 5, the compounds of the present invention have stronger anti-proliferative activity on MIA PaCa-2 cells compared with the control drug MK-1775; at the same time, the compounds of the present invention have stronger activity in combination with GMC, for example, compounds 66, 67 and 68 have $IC_{50}$ less than 1 nM. The compounds of the present invention have stronger activity in combination with GMC, which indicates that the compounds may have a better effect when being in combination with chemotherapeutic drugs clinically.

Although specific embodiments of the present invention have been described above, it will be appreciated by those skilled in the art that these embodiments are merely illustrative and that many changes or modifications can be made to these embodiments without departing from the principles and spirit of the present invention. The protection scope of the present invention is therefore defined by the appended claims.

The invention claimed is:

1. A compound of general formula (1) or an optical isomer, a crystalline form, a pharmaceutically acceptable salt, a hydrate or a solvate thereof:

(1)

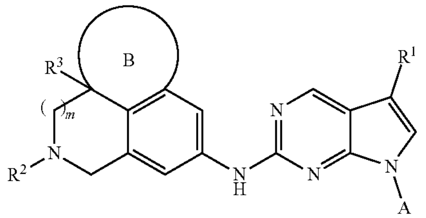

wherein in general formula (1):

m is 0 or 1;

$R^1$ is H or halogen;

$R^2$ is H, C1-C6 alkyl, C3-C6 cycloalkyl, deuterated C1-C6 alkyl, halogenated C1-C6 alkyl, C1-C6 alkyl substituted with CN, C1-C6 alkyl substituted with OH, C1-C6 alkyl substituted with C1-C3 alkoxy, C1-C6 alkyl substituted with C3-C6 cycloalkyl or 4- to 7-membered heterocycloalkyl;

$R^3$ is H or C1-C3 alkyl;

A is aryl or heteroaryl, wherein the aryl and heteroaryl are optionally substituted with 1 to 3 $R^6$, each $R^6$ is independently H, halogen, CN, C1-C6 alkyl, C1-C6 alkoxy, C3-C6 cycloalkyl, halogenated C1-C6 alkyl, halogenated C1-C6 alkoxy, C1-C6 alkyl substituted with OH, C1-C6 alkyl substituted with cyano, halogenated C3-C6 cycloalkyl, C3-C6 cycloalkyl substituted with hydroxy, C3-C6 cycloalkyl substituted with cyano, C3-C6 cycloalkyl substituted with $CF_3$, $—NR^{7a}R^{7b}$, $—N{=}S(O)R^{7a}R^{7b}$, $—P(O)R^{7a}R^{7b}$, $—S(O)_2R^{7a}$, $—S(O)_2NR^{7a}R^{7b}$, $—NR^8P(O)R^{7a}R^{7b}$, $—NR^8S(O)_2R^{7a}$, $—NR^8C(O)R^{7a}$, $—N{=}S({=}NR^8)R^{7a}R^{7b}$ or pyridonyl;

$R^{7a}$ and $R^{7b}$ are independently C1-C3 alkyl, deuterated C1-C3 alkyl, C2-C6 alkenyl, C2-C6 alkynyl or C3-C6 cycloalkyl, or $R^{7a}$ and $R^{7b}$ together with the nitrogen, sulfur or phosphorus atom attached thereto, form 3- to 10-membered heterocycloalkyl;

$R^8$ is H or C1-C3 alkyl, or $R^8$ and $R^{7a}$, together with the nitrogen and sulfur atoms or nitrogen and carbon atoms attached thereto, form 3- to 10-membered heterocycloalkyl;

B is partially unsaturated C5-C7 cycloalkyl or partially unsaturated 5- to 7-membered heterocycloalkyl.

2. The compound or the optical isomer, the crystalline form, the pharmaceutically acceptable salt, the hydrate or the solvate thereof according to claim 1, wherein in general formula (1),

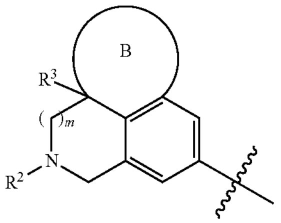

is

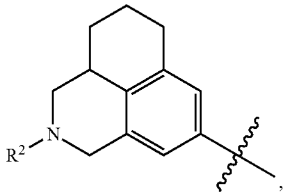

,

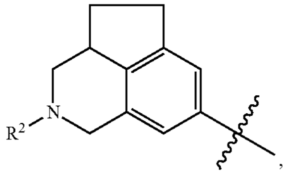

,

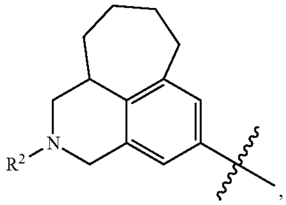

,

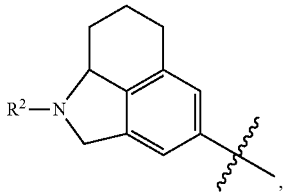

,

-continued

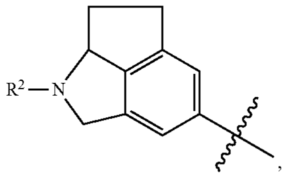

,

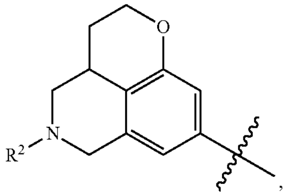

,

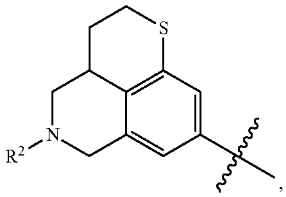

,

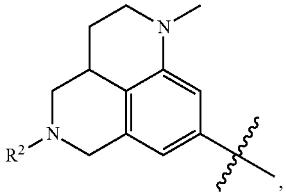

,

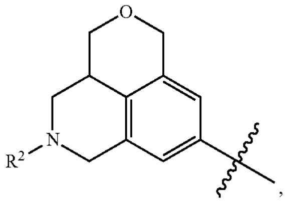

,

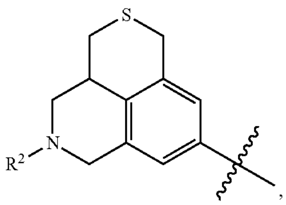

,

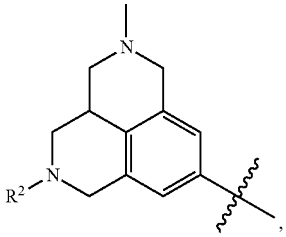

,

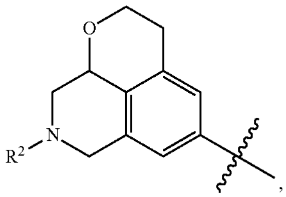

,

-continued
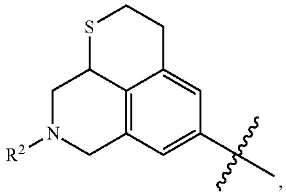
,
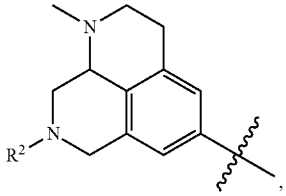
,
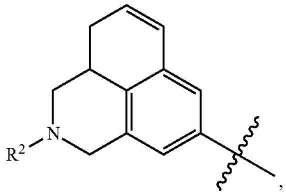
,
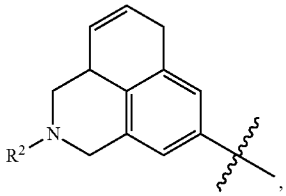
,
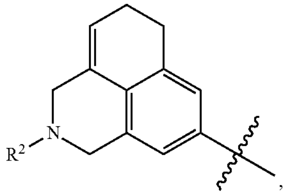
,
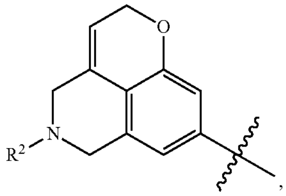
,
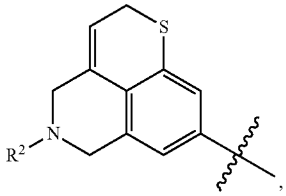
,
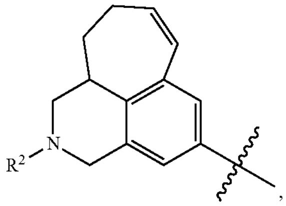
,
-continued
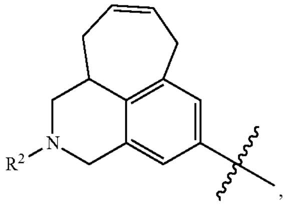
,
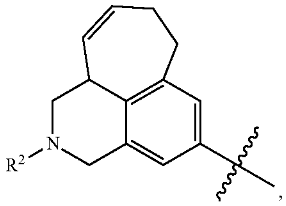
,
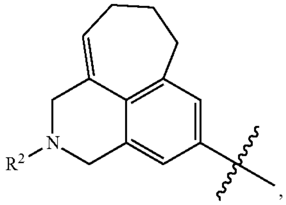
,
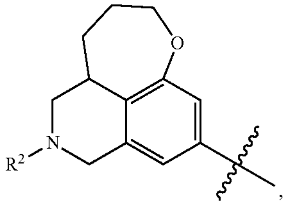
,
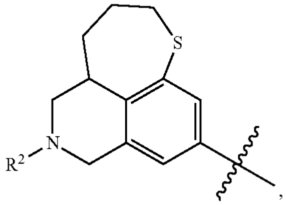
,
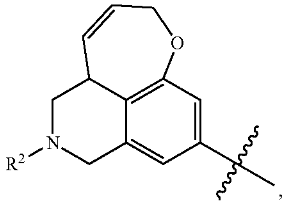
,
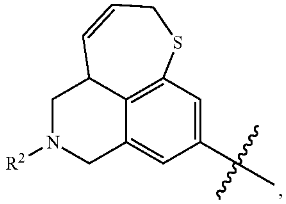
,
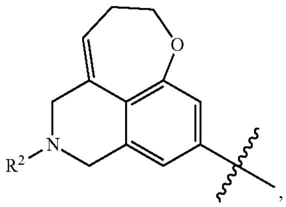
, -continued
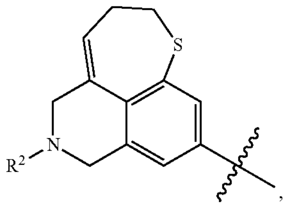
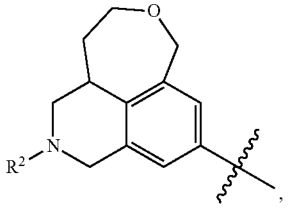
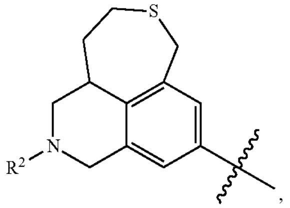
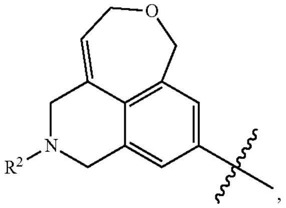
or
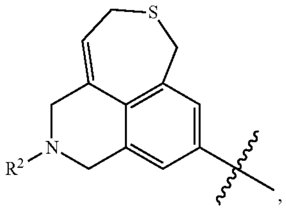
wherein $R^2$ is H, Me, Et, $CD_3$,
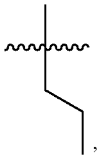
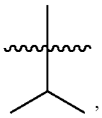
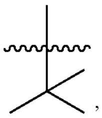
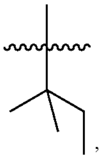
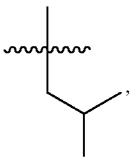
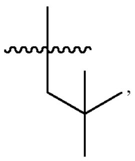
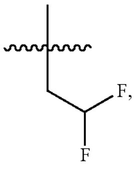
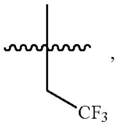
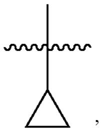
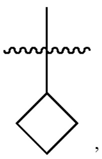
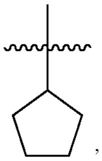
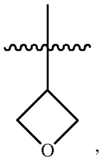
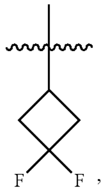
-continued
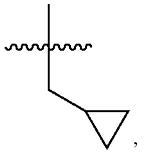
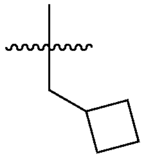
or
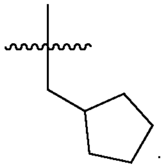
3. The compound or the optical isomer, the crystalline form, the pharmaceutically acceptable salt, the hydrate or the solvate thereof according to claim 2, wherein in general formula (1),
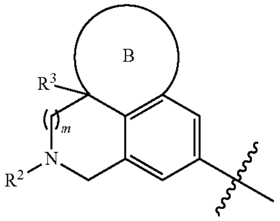
is
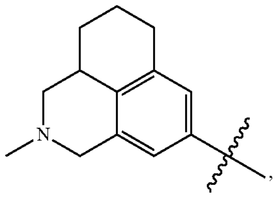
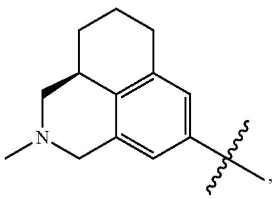
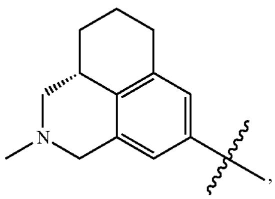
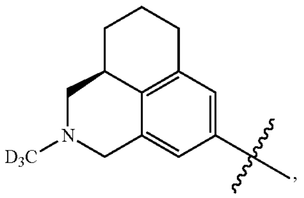
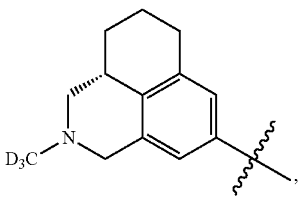
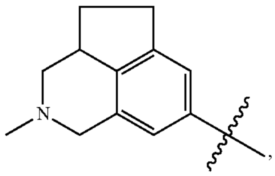
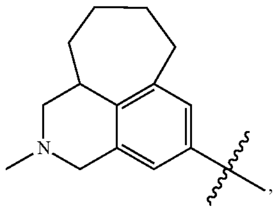
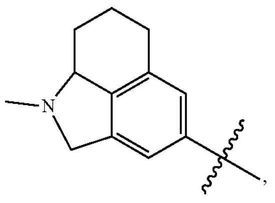
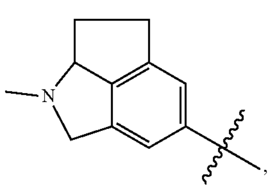
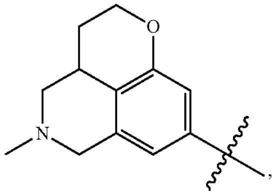

-continued
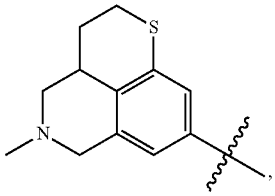,
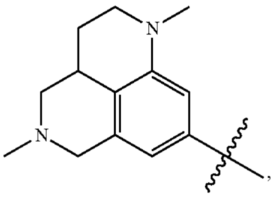,
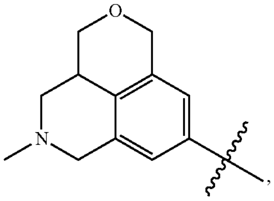,
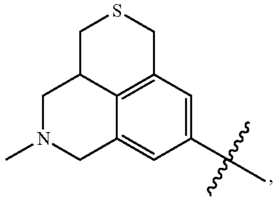,
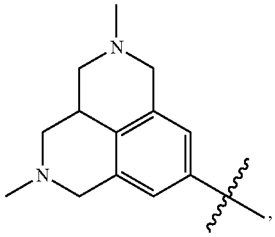,
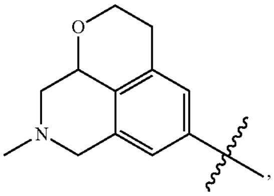,
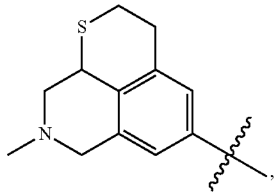,
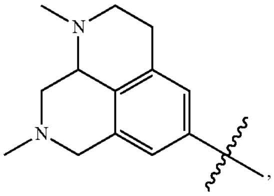,
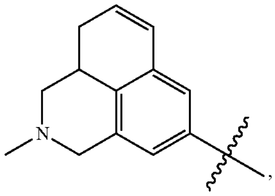,
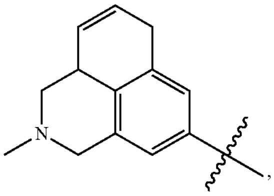,
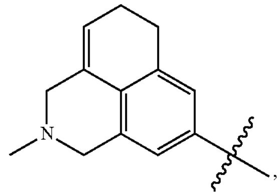,
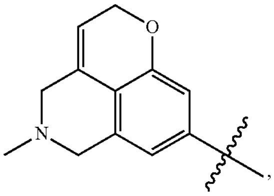,
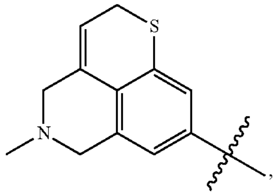,
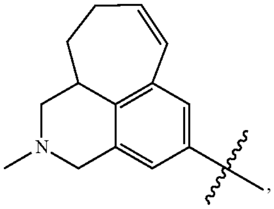,
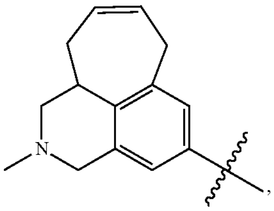,
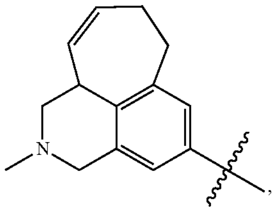,
-continued
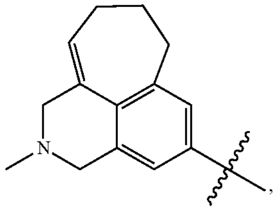,
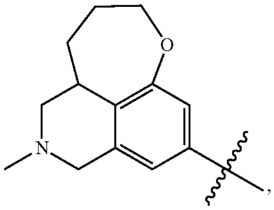,
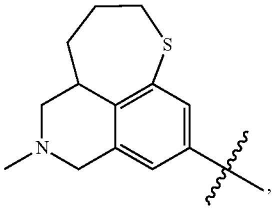,
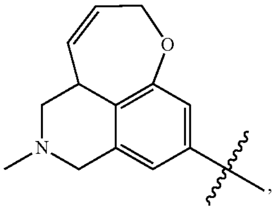,
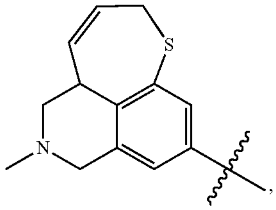,
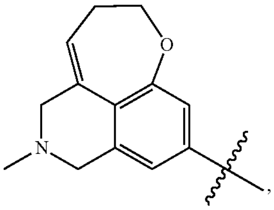,
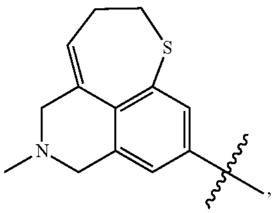,
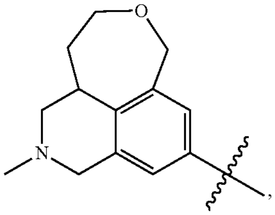,
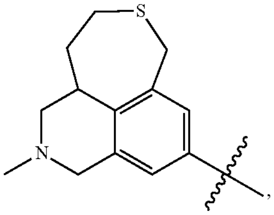,
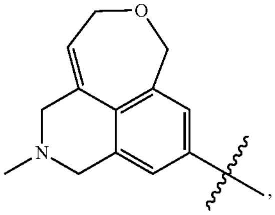, or
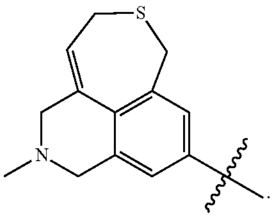.
4. The compound or the optical isomer, the crystalline form, the pharmaceutically acceptable salt, the hydrate or the solvate thereof according to claim 1, wherein the compound has a structure of general formula (1A):

(1A)

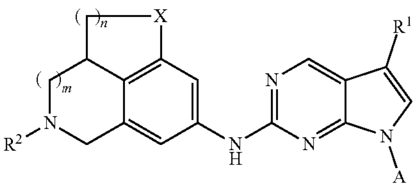

wherein in general formula (1A):

n is 1, 2 or 3;

X is $CH_2$, O or S;

m, A, $R^1$ and $R^2$ are as defined in claim 1.

5. The compound or the optical isomer, the crystalline form, the pharmaceutically acceptable salt, the hydrate or the solvate thereof according to claim 4, wherein in general formula (1A), A is phenyl, pyridinyl, pyrimidinyl or pyrazinyl, wherein the phenyl, pyridinyl, pyrimidinyl and pyrazinyl may be optionally substituted with 1 to 3 $R^6$, each $R^6$ is independently H, halogen, CN, C1-C6 alkyl, C1-C6 alkoxy, C3-C6 cycloalkyl, halogenated C1-C6 alkyl, halogenated C1-C6 alkoxy, C1-C6 alkyl substituted with hydroxy, C1-C6 alkyl substituted with cyano, halogenated C3-C6 cycloalkyl, C3-C6 cycloalkyl substituted with OH, C3-C6 cycloalkyl substituted with cyano, C3-C6 cycloalkyl substituted with $CF_3$, $—NR^{7a}R^{7b}$, $—N{=}S(O)R^{7a}R^{7b}$, $—P(O)R^{7a}R^{7b}$, $—S(O)_2R^{7a}$, $—S(O)_2NR^{7a}R^{7b}$, $—NR^8P(O)R^{7a}R^{7b}$, —NR'S$(O)_2R^{7a}$, $—NR^8C(O)R^{7a}$, $—N{=}S({=}NR^8)R^{7a}R^{7b}$ or pyridonyl, wherein $R^{7a}$ and $R^{7b}$ are independently C1-C3 alkyl, deuterated C1-C3 alkyl, C2-C6 alkenyl, C2-C6 alkynyl or C3-C6 cycloalkyl, or $R^{7a}$ and $R^{7b}$, together with the nitrogen, sulfur or phosphorus atom attached thereto, form 3- to 10-membered heterocycloalkyl; $R^8$ is H or C1-C3 alkyl, or $R^8$ and $R^{7a}$, together with the nitrogen and sulfur atoms or nitrogen and carbon atoms attached thereto, form 3- to 10-membered heterocycloalkyl.

6. The compound or the optical isomer, the crystalline form, the pharmaceutically acceptable salt, the hydrate or the solvate thereof according to claim 4, wherein in general formula (1A), A is

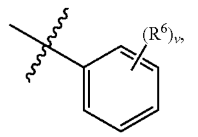

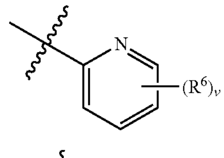

,

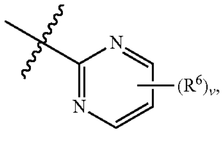

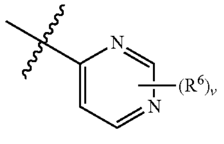

or

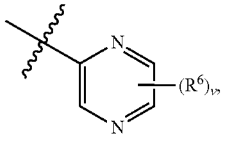

wherein v is 1, 2 or 3, and each $R^6$ is independently H, halogen, Me, Et,

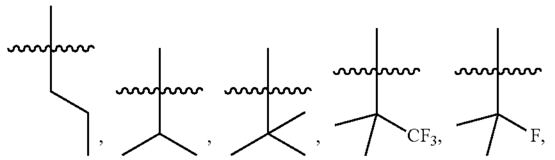

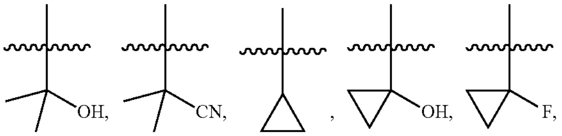

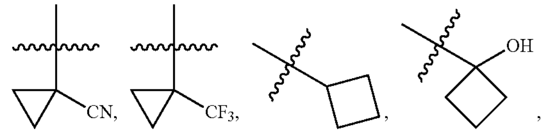

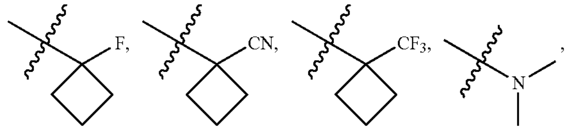

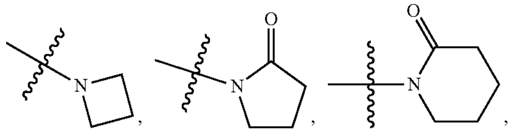

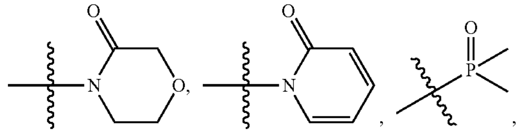

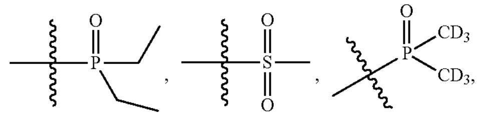

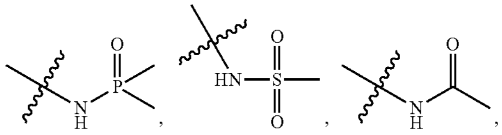

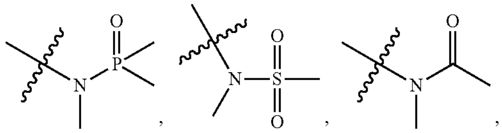

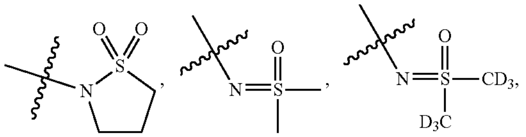

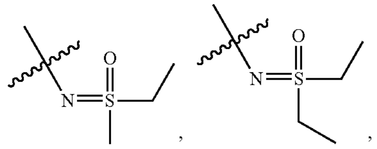

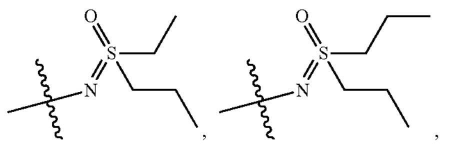

-continued
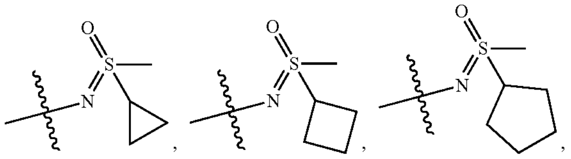
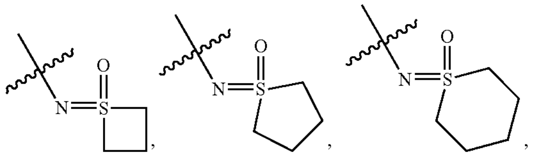
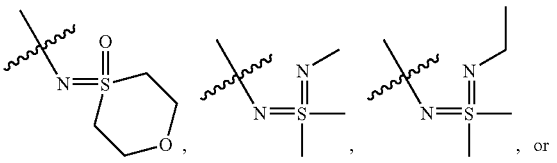
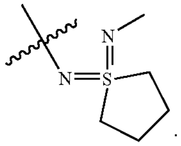
7. The compound or the optical isomer, the crystalline form, the pharmaceutically acceptable salt, the hydrate or the solvate thereof according to claim 6, wherein in general formula (1A), A is
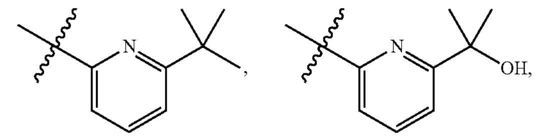
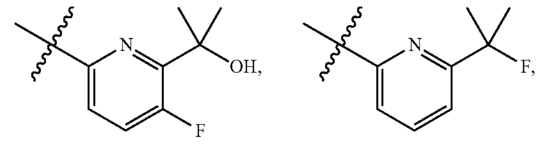
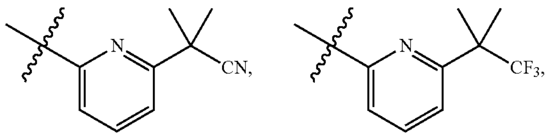
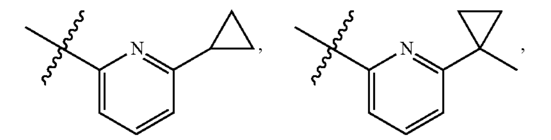
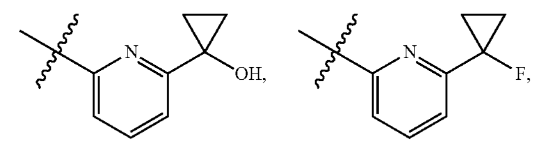
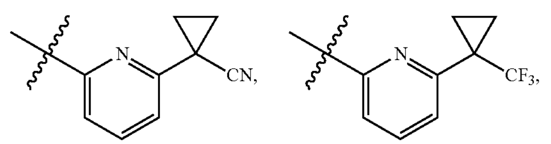
-continued
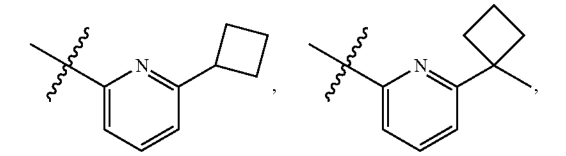
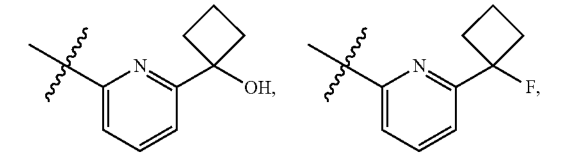
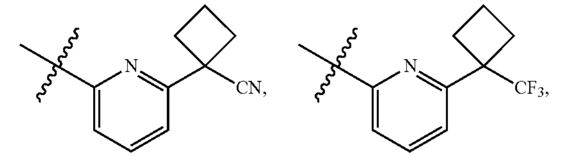
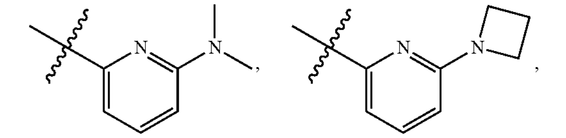
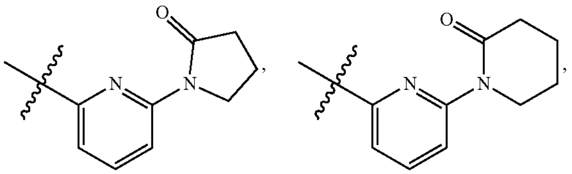
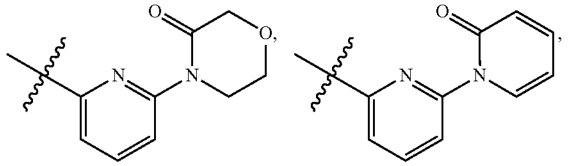
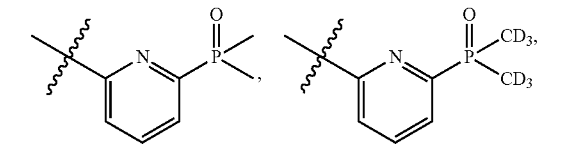
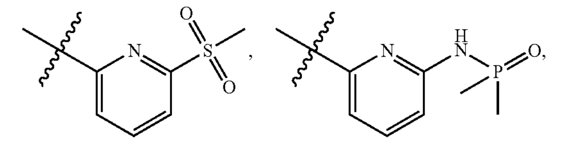
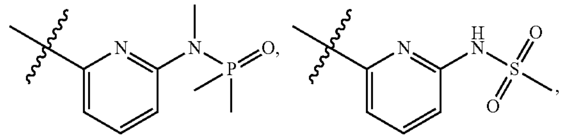
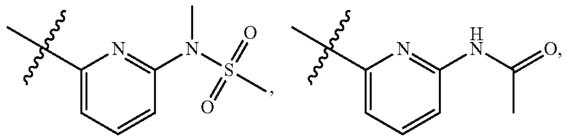
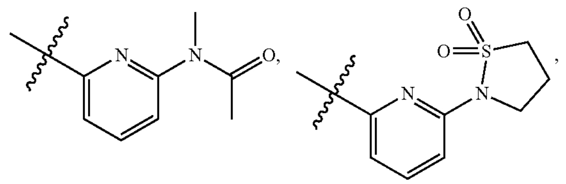

-continued

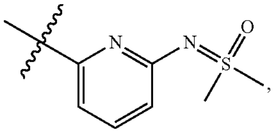

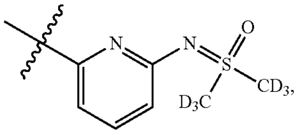

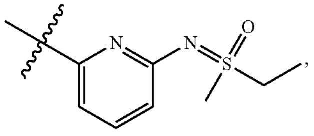

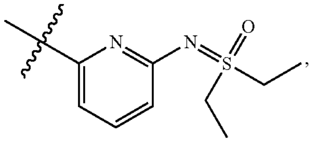

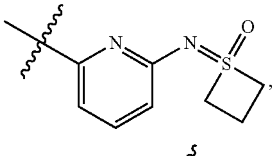 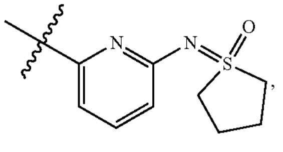

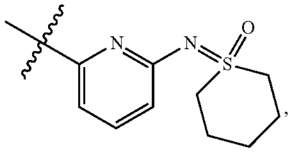

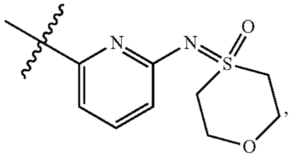

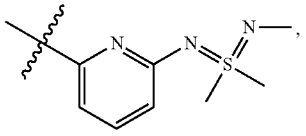

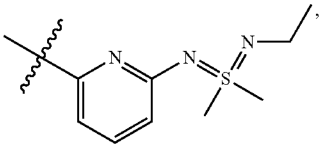

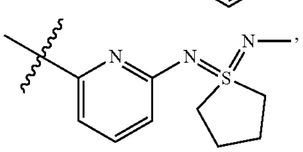 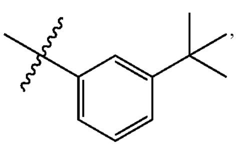

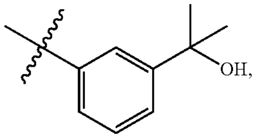 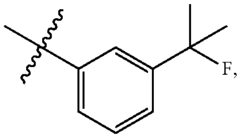

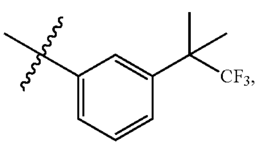 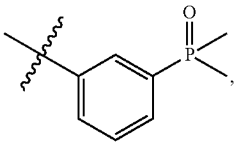

-continued

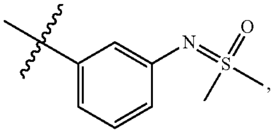 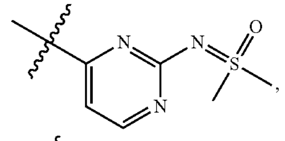

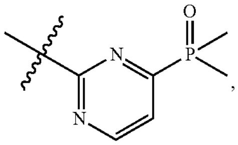 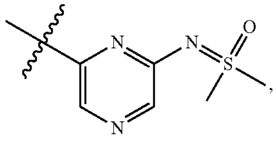

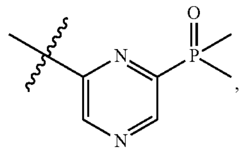 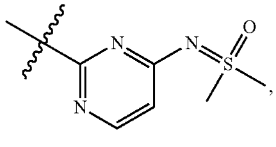

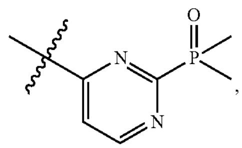 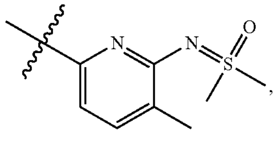

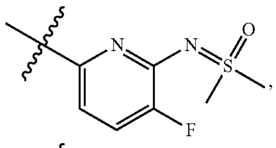 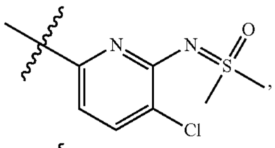

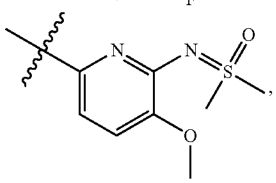 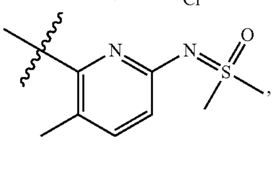

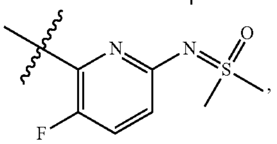 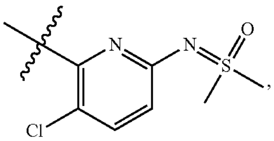

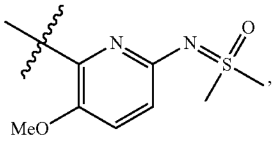 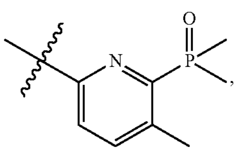

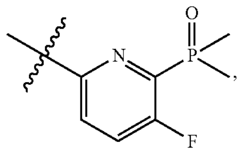 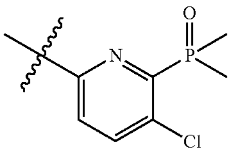 or

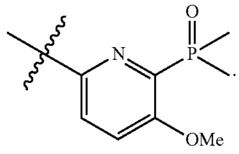

8. The compound or the optical isomer, the crystalline form, the pharmaceutically acceptable salt, the hydrate or the solvate thereof according to claim 1, wherein in general formula (1), A is phenyl, pyridinyl, pyrimidinyl or pyrazinyl, wherein the phenyl, pyridinyl, pyrimidinyl and pyrazinyl may be optionally substituted with 1 to 3 $R^6$, each $R^6$ is independently H, halogen, CN, C1-C6 alkyl, C1-C6 alkoxy, C3-C6 cycloalkyl, halogenated C1-C6 alkyl, halogenated C1-C6 alkoxy, C1-C6 alkyl substituted with hydroxy, C1-C6 alkyl substituted with cyano, halogenated C3-C6 cycloalkyl, C3-C6 cycloalkyl substituted with OH, C3-C6 cycloalkyl substituted with cyano, C3-C6 cycloalkyl substituted with $CF_3$, $—NR^{7a}R^{7b}$, $—N{=}S(O)R^{7a}R^{7b}$, $—P(O)R^{7a}R^{7b}$, $—S(O)_2R^{7a}$, $—S(O)_2NR^{7a}R^{7b}$, $—NR^8P(O)R^{7a}R^{7b}$, $—NR'S(O)_2R^{7a}$, $—NR^8C(O)R^{7a}$, $—N{=}S({=}NR^8)R^{7a}R^{7b}$ or pyridonyl, wherein $R^{7a}$ and $R^{7b}$ are independently C1-C3 alkyl, deuterated C1-C3 alkyl, C2-C6 alkenyl, C2-C6 alkynyl or C3-C6 cycloalkyl, or $R^{7a}$ and $R^{7b}$, together with the nitrogen, sulfur or phosphorus atom attached thereto, form 3- to 10-membered heterocycloalkyl; $R^8$ is H or C1-C3 alkyl, or $R^8$ and $R^{7a}$, together with the nitrogen and sulfur atoms or nitrogen and carbon atoms attached thereto, form 3- to 10-membered heterocycloalkyl.

9. The compound or the optical isomer, the crystalline form, the pharmaceutically acceptable salt, the hydrate or the solvate thereof according to claim 1, wherein in general formula (1), A is

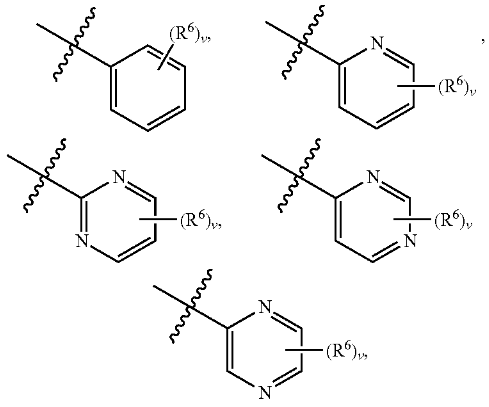

or wherein v is 1, 2 or 3, and each $R^6$ is independently H, halogen, Me, Et,

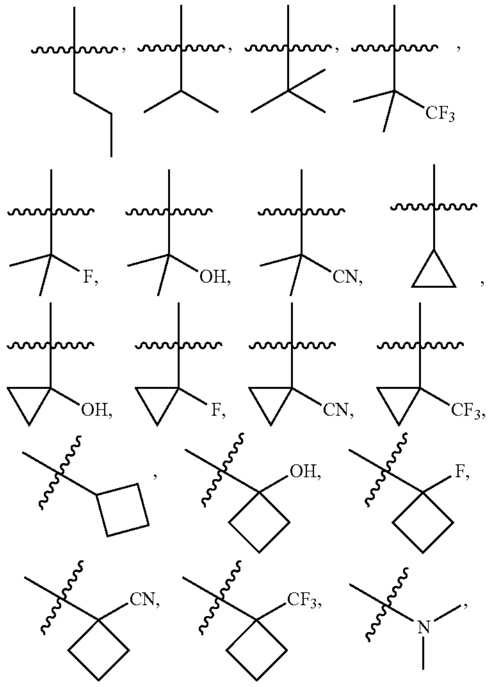

-continued

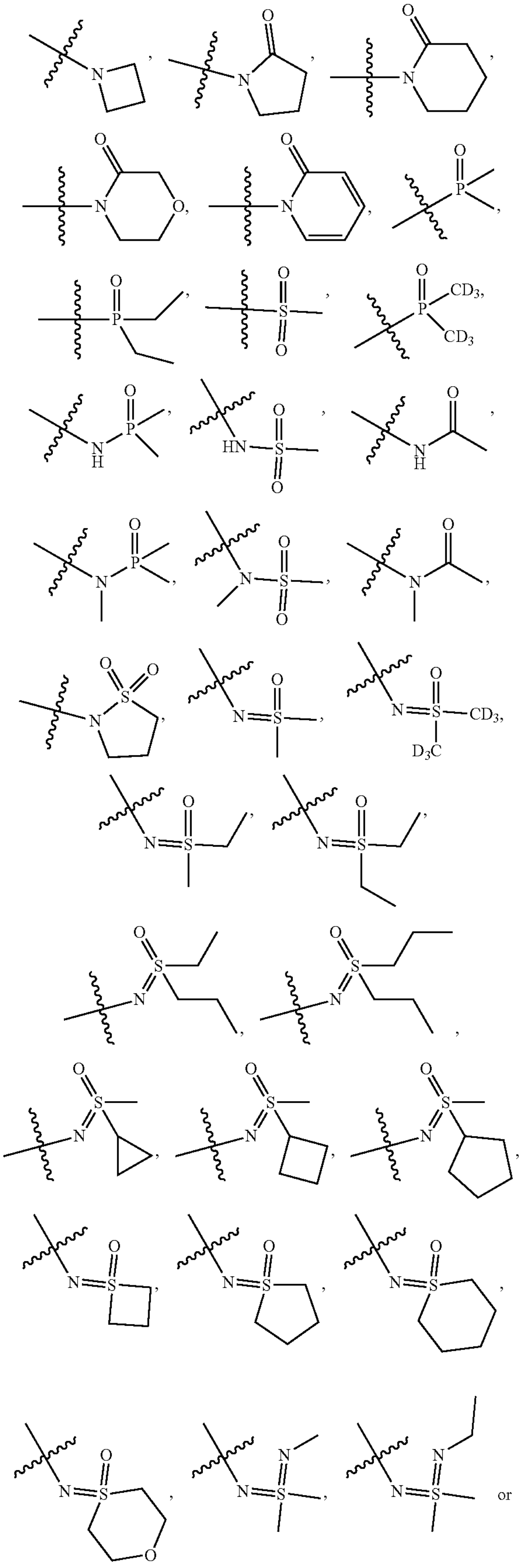

or

-continued
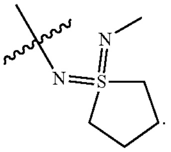
10. The compound or the optical isomer, the crystalline form, the pharmaceutically acceptable salt, the hydrate or the solvate thereof according to claim 9, wherein in general formula (1), A is
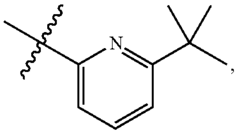
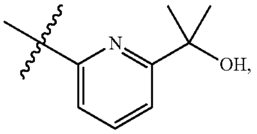
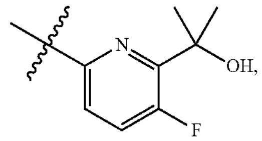
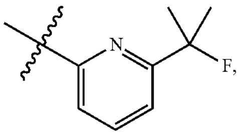
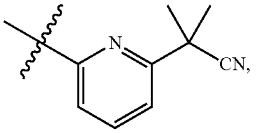
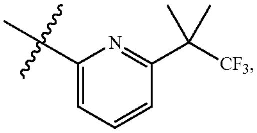
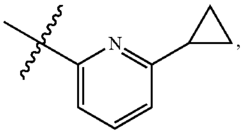
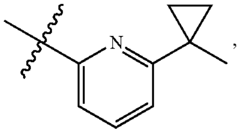
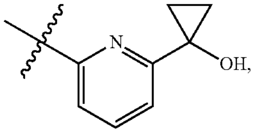
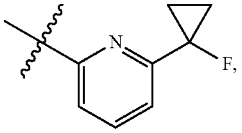
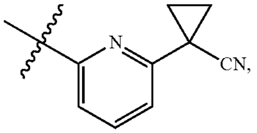
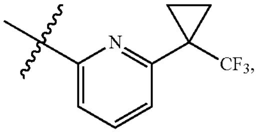
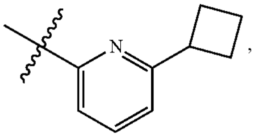
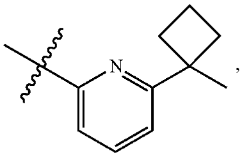
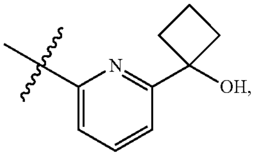
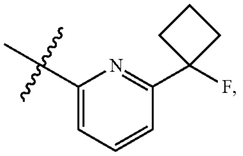
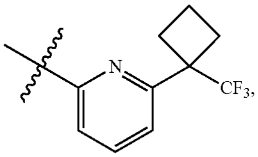
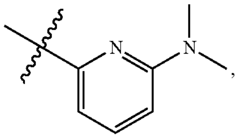
-continued
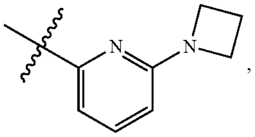
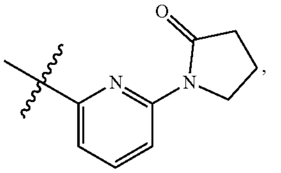
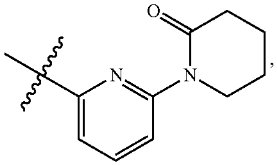
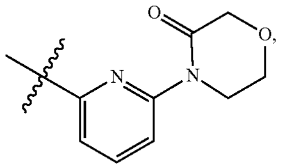
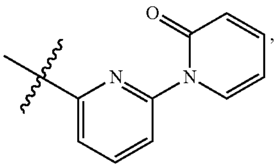
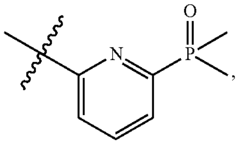
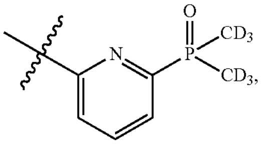
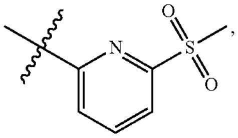
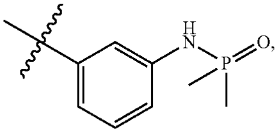
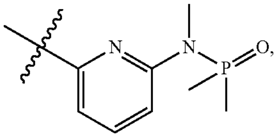
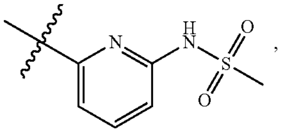
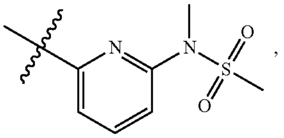
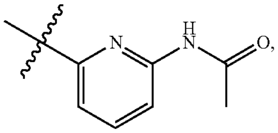
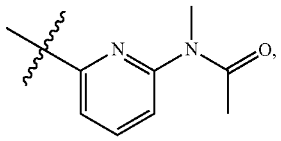
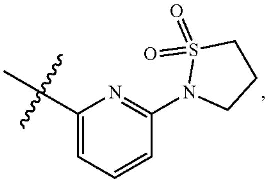
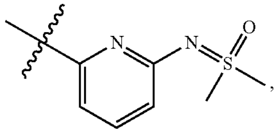
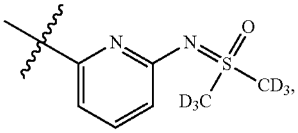
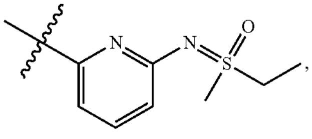

-continued
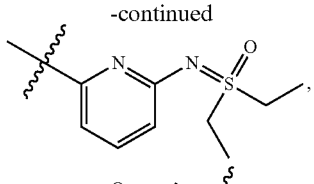,
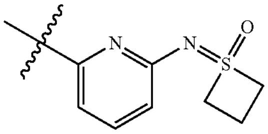, 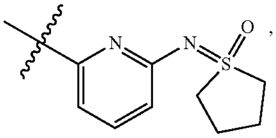,
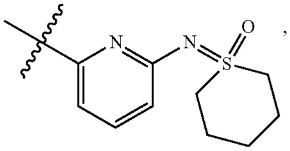,
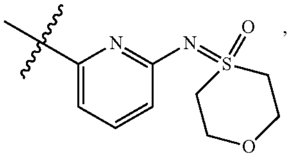 [SMILES: *c1cccc(N=S2(=O)CCOCC2)n1],
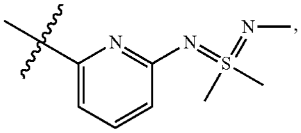,
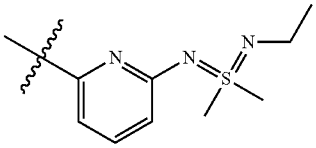,
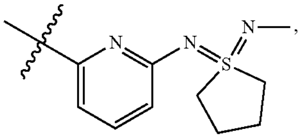, 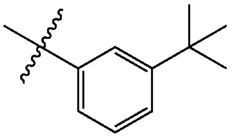,
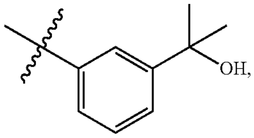, 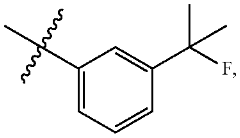,
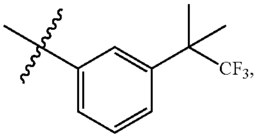, 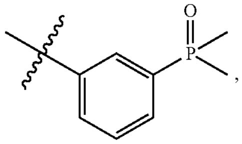,
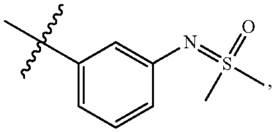, 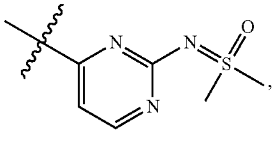,
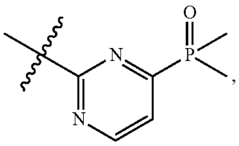, 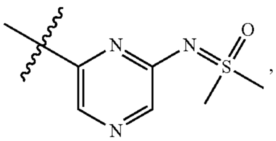,
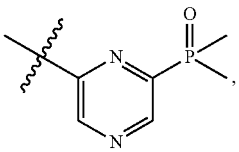, 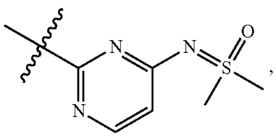,
-continued
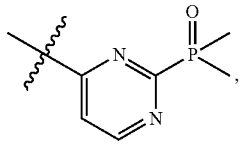, 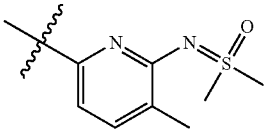,
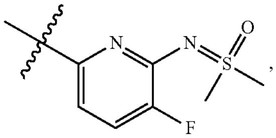, 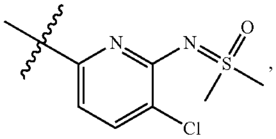,
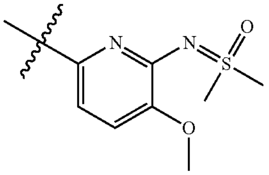, 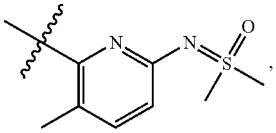,
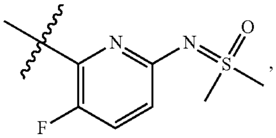, 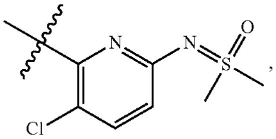,
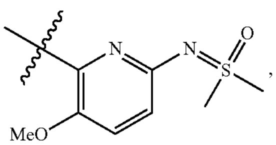, 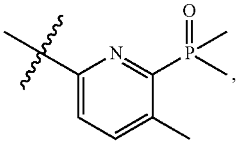,
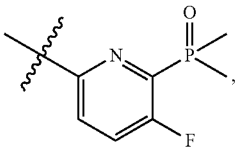, 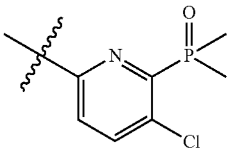 or
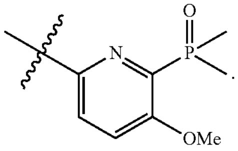.
11. The compound or the optical isomer, the crystalline form, the pharmaceutically acceptable salt, the hydrate or the solvate thereof according to claim 1, wherein the compound has one of the following structures:
1
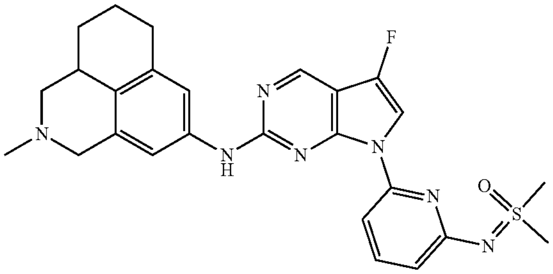

-continued
2
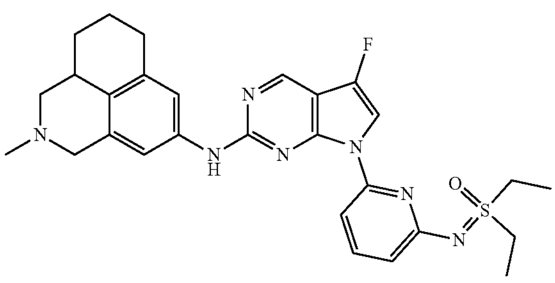
3
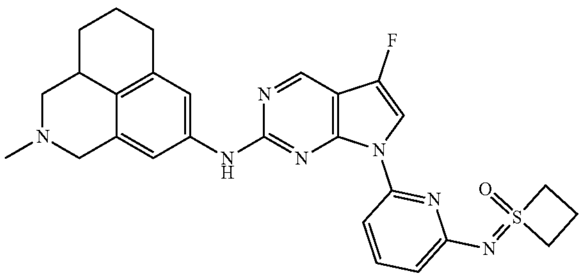
4
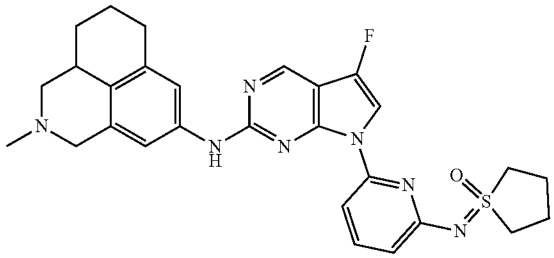
5
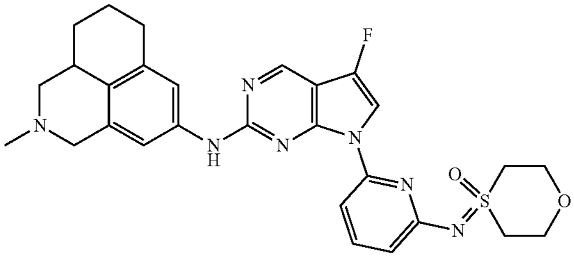
6
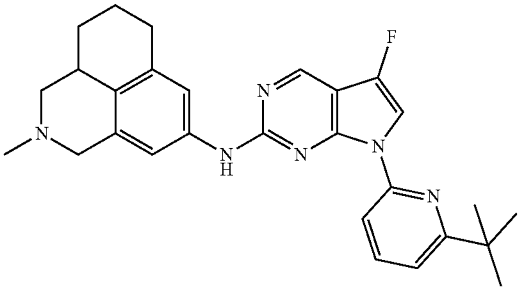
-continued
7
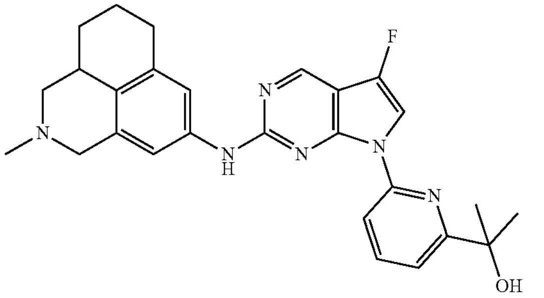
8
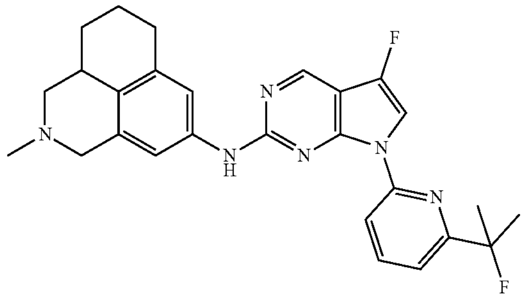
9
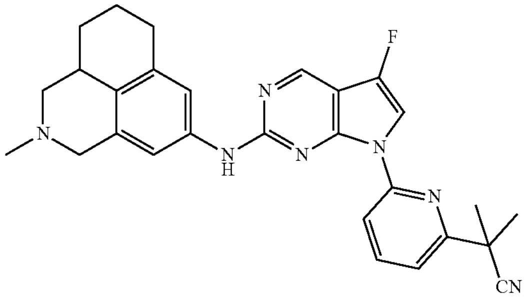
10
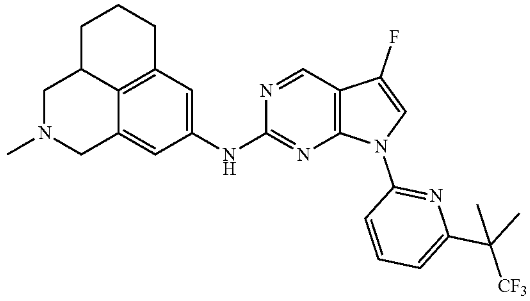
11
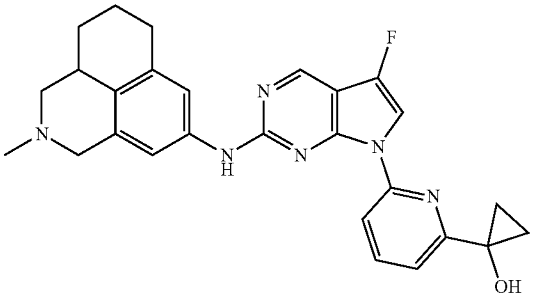

-continued
12
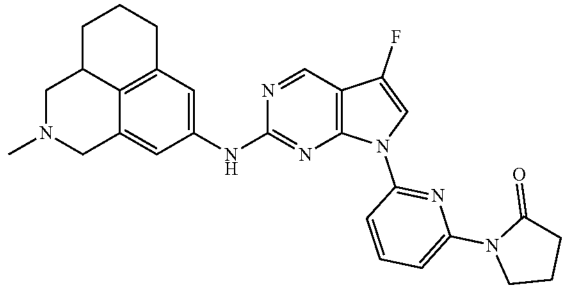
13
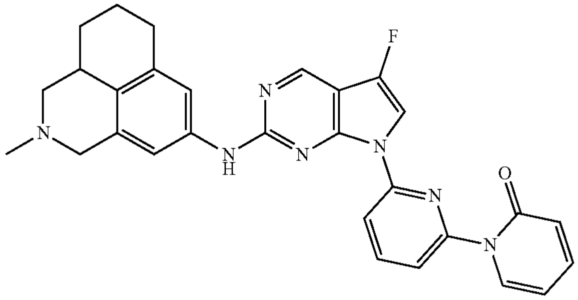
14
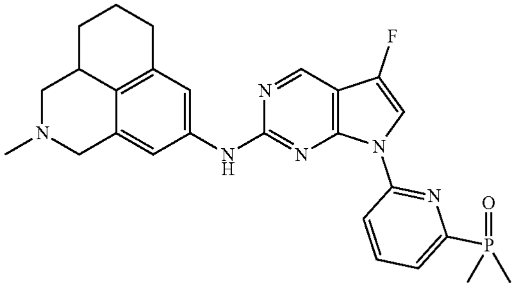
15
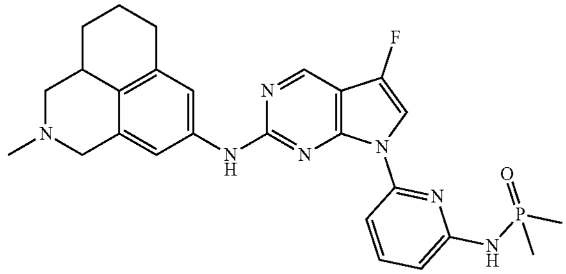
16
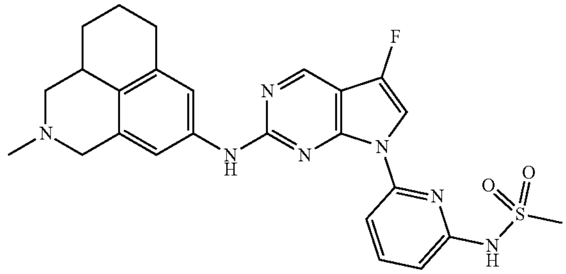
-continued
17
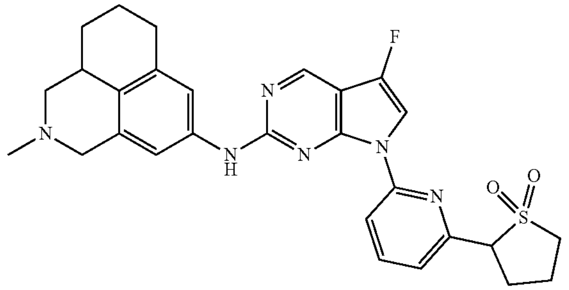
18
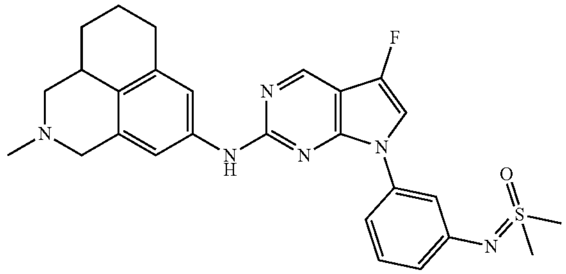
19
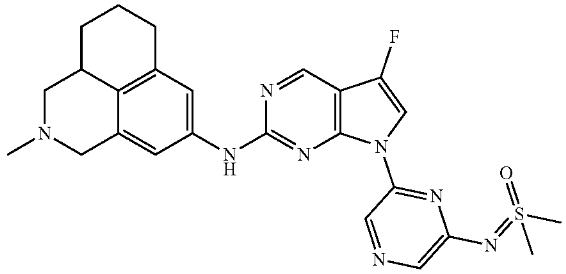
20
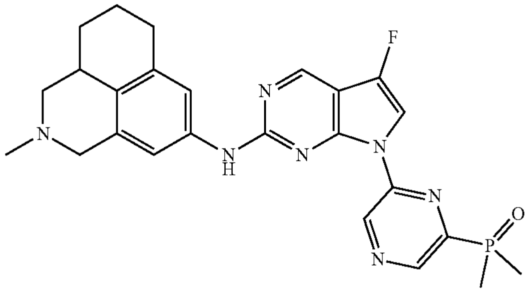
21
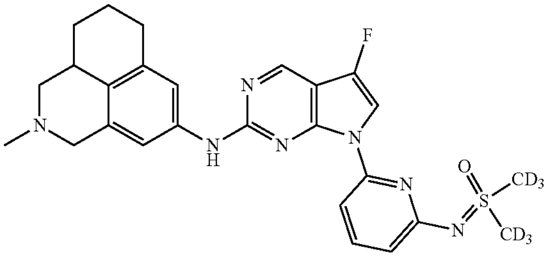

-continued
22
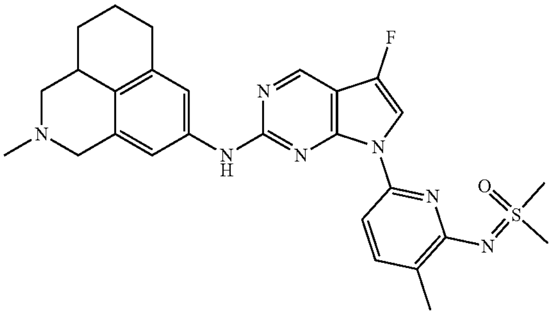
23
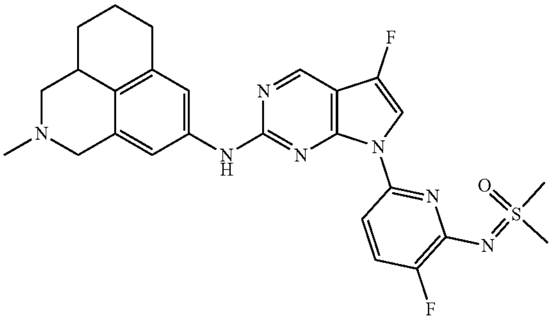
24
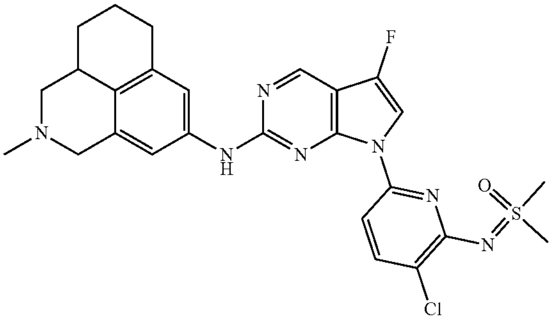
25
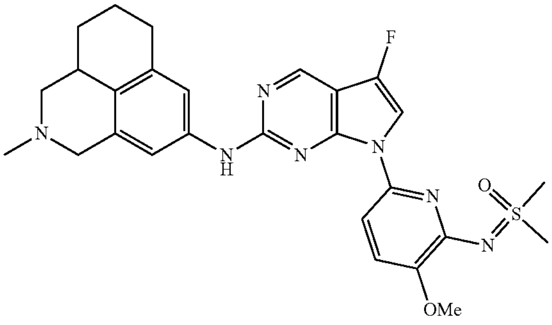
-continued
26
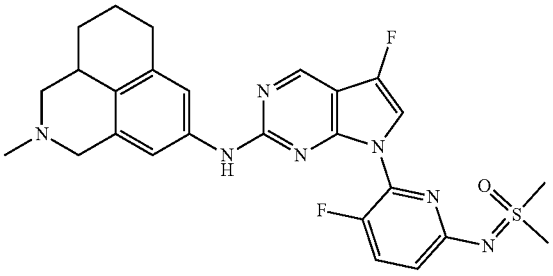
27
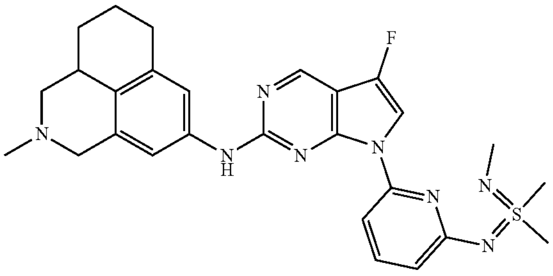
28
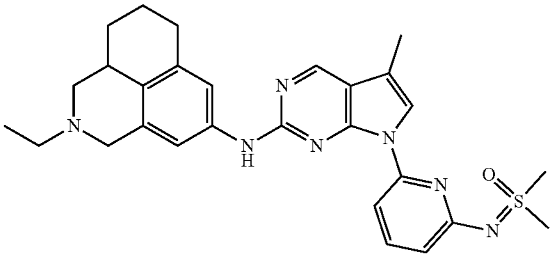
29
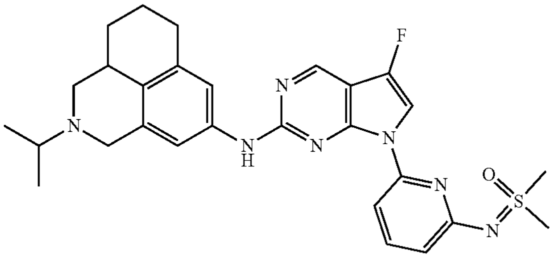
30
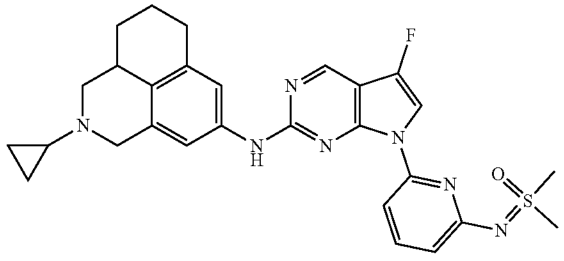

-continued
31
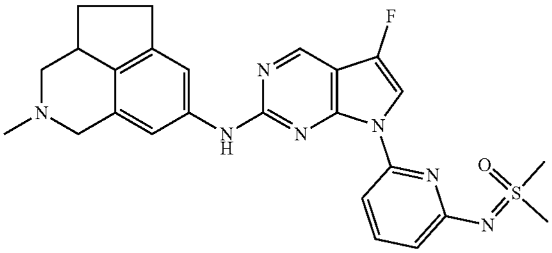
32
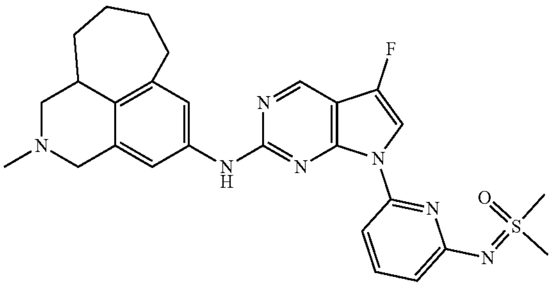
33
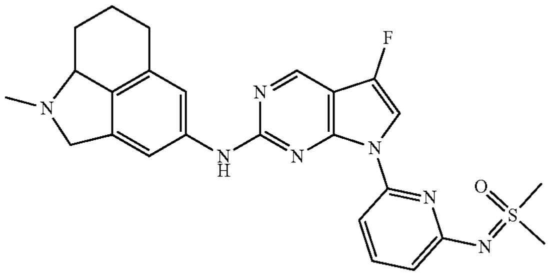
34
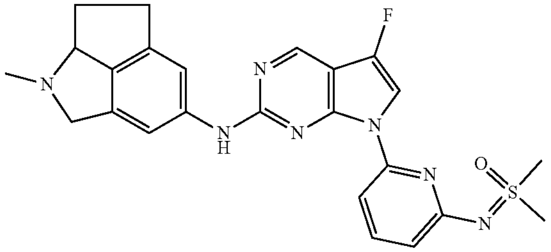
35
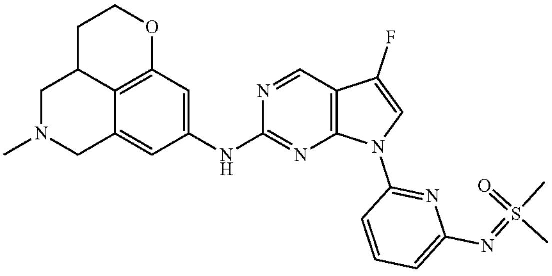
-continued
36
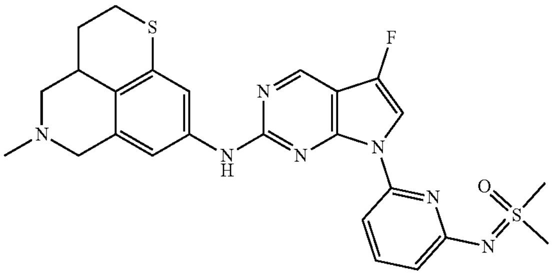
37
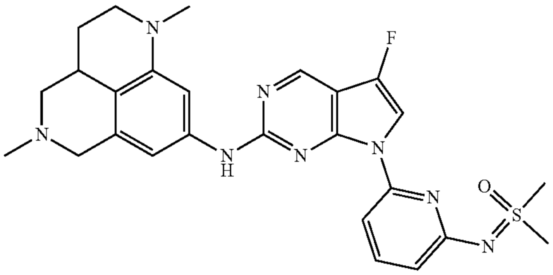
38
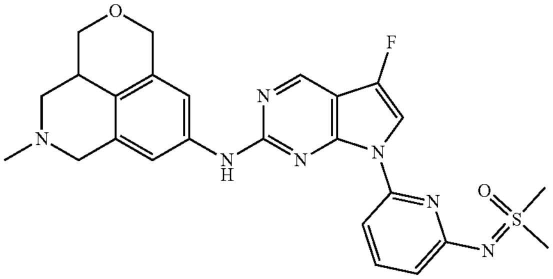
39
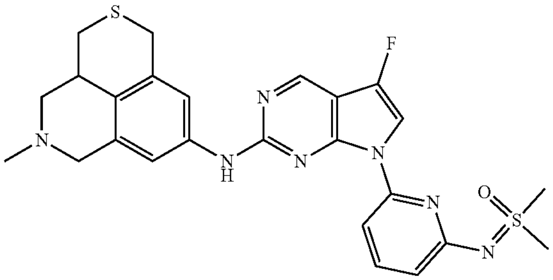
40
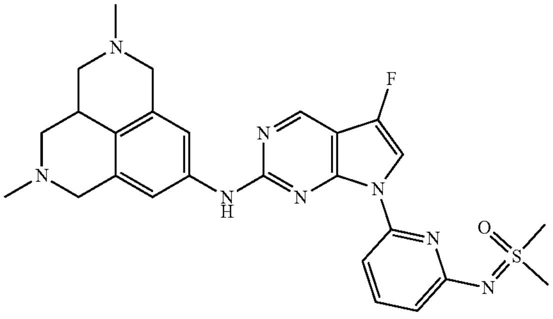

-continued
41
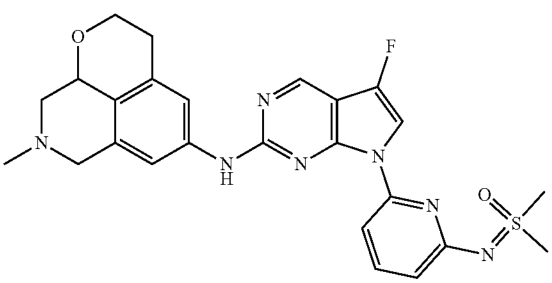
42
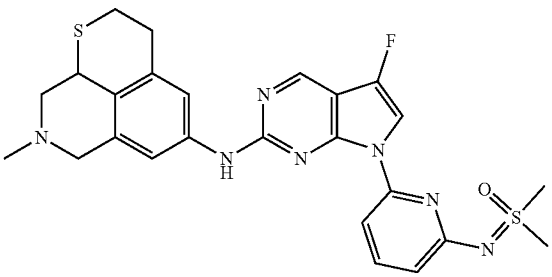
43
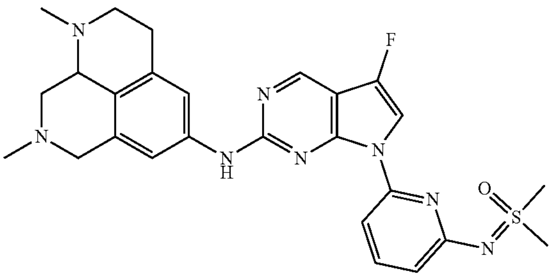
44
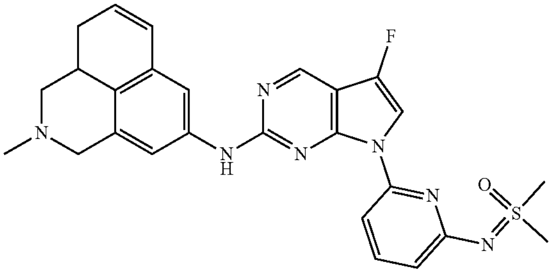
45
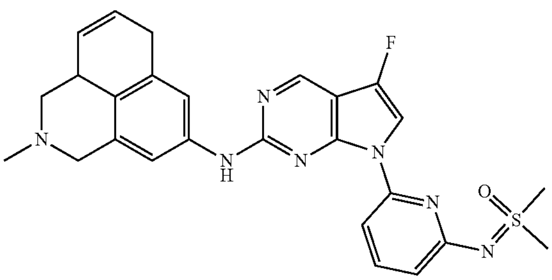
-continued
46
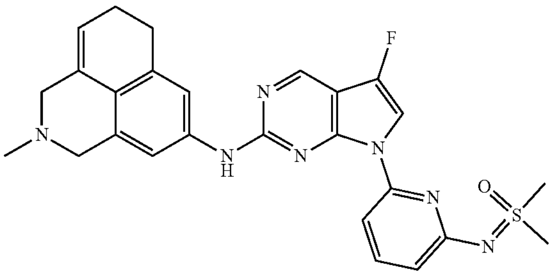
47
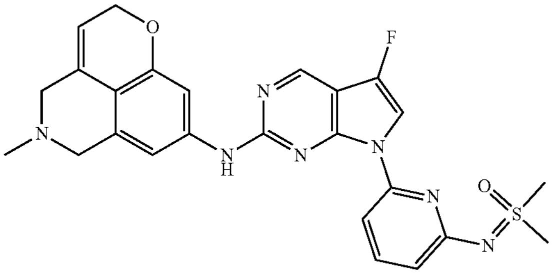
48
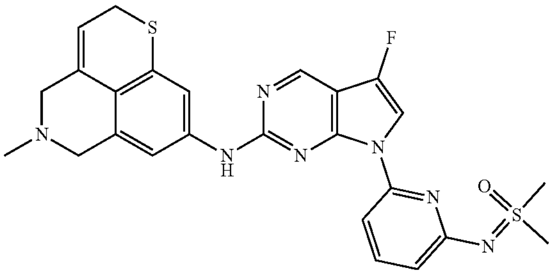
49
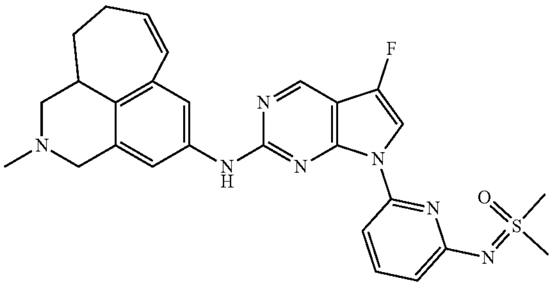
50
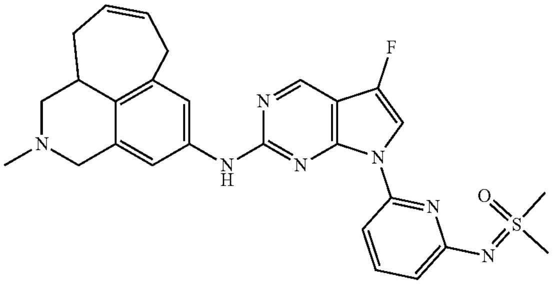

-continued
51
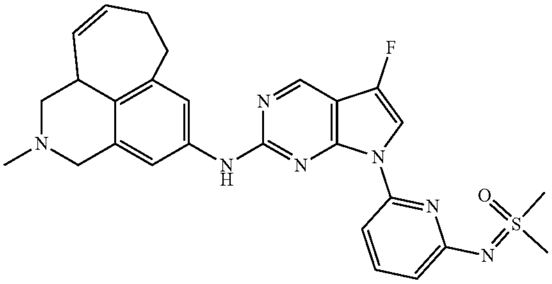
52
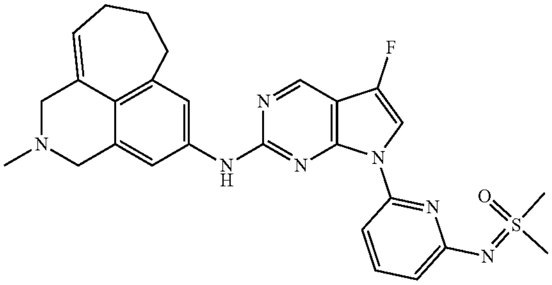
53
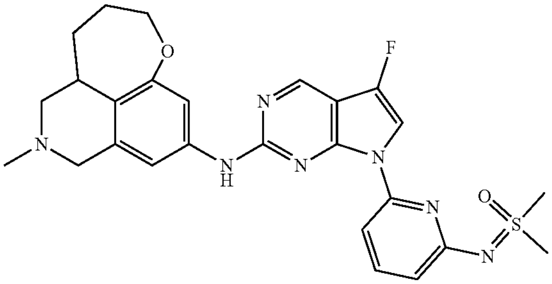
54
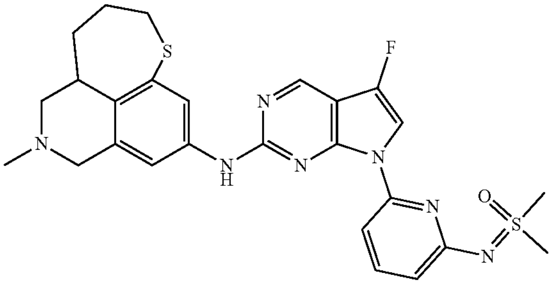
-continued
55
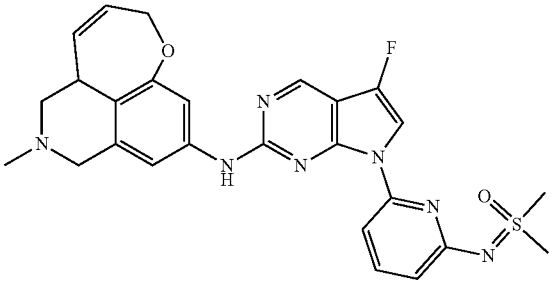
56
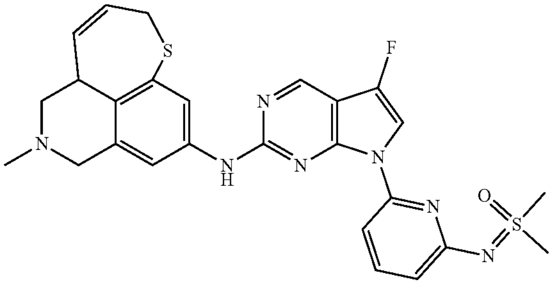
57
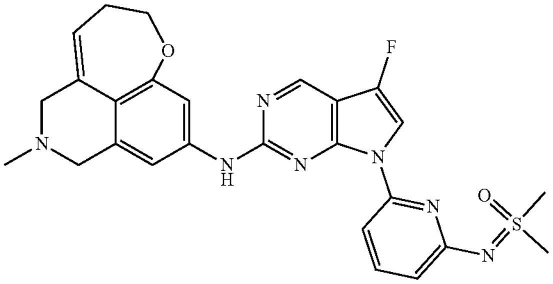
12. A pharmaceutical composition, comprising a pharmaceutically acceptable excipient or carrier, and the compound or the optical isomer, the crystalline form, the pharmaceutically acceptable salt, the hydrate or the solvate thereof according to claim 1 as an active ingredient.
* * * * *